US010900039B2

(12) United States Patent
Cauwenbergh

(10) Patent No.: US 10,900,039 B2
(45) Date of Patent: Jan. 26, 2021

(54) METHODS FOR TREATING AGING AND SKIN DISORDERS USING NUCLEIC ACIDS TARGETING TYR OR MMP1

(71) Applicant: Phio Pharmaceuticals Corp., Marlborough, MA (US)

(72) Inventor: Gerard Cauwenbergh, Plainsboro, NJ (US)

(73) Assignee: Phio Pharmaceuticals Corp., Marlborough, MA (US)

( * ) Notice: Subject to any disclaimer, the term of this patent is extended or adjusted under 35 U.S.C. 154(b) by 372 days.

(21) Appl. No.: 15/508,768

(22) PCT Filed: Sep. 4, 2015

(86) PCT No.: PCT/US2015/048565
§ 371 (c)(1),
(2) Date: Mar. 3, 2017

(87) PCT Pub. No.: WO2016/037071
PCT Pub. Date: Mar. 10, 2016

(65) Prior Publication Data
US 2018/0030451 A1  Feb. 1, 2018

Related U.S. Application Data

(60) Provisional application No. 62/102,287, filed on Jan. 12, 2015, provisional application No. 62/047,972, filed on Sep. 9, 2014, provisional application No. 62/046,523, filed on Sep. 5, 2014.

(51) Int. Cl.
C12N 15/113 (2010.01)
A61K 31/713 (2006.01)
C12Q 1/68 (2018.01)

(52) U.S. Cl.
CPC ........ *C12N 15/1137* (2013.01); *A61K 31/713* (2013.01); *C12Y 114/18001* (2013.01); *C12Y 114/99001* (2013.01); *C12Y 304/24007* (2013.01); *C12N 2310/14* (2013.01); *C12N 2310/315* (2013.01); *C12N 2310/321* (2013.01); *C12N 2310/322* (2013.01); *C12N 2310/3515* (2013.01); *C12N 2320/31* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,201,860 A | 5/1980 | Naito et al. |
| 4,235,871 A | 11/1980 | Papahadjopoulos et al. |
| 4,415,732 A | 11/1983 | Caruthers et al. |
| 4,426,330 A | 1/1984 | Sears |
| 4,737,323 A | 4/1988 | Martin et al. |
| 4,810,646 A | 3/1989 | Jamas et al. |
| 4,837,028 A | 6/1989 | Allen |
| 4,897,355 A | 1/1990 | Eppstein et al. |
| 4,904,582 A | 2/1990 | Tullis |
| 4,958,013 A | 9/1990 | Letsinger |
| 4,992,540 A | 2/1991 | Jamas et al. |
| 5,023,243 A | 6/1991 | Tullis |
| 5,028,703 A | 7/1991 | Jamas et al. |
| 5,032,401 A | 7/1991 | Jamas et al. |
| 5,051,257 A | 9/1991 | Pietronigro |
| 5,082,936 A | 1/1992 | Jamas et al. |
| 5,112,963 A | 5/1992 | Pieles et al. |
| 5,151,510 A | 9/1992 | Stec et al. |
| 5,162,115 A | 11/1992 | Pietronigro |
| 5,188,897 A | 2/1993 | Suhadolnik et al. |
| 5,264,423 A | 11/1993 | Cohen et al. |
| 5,264,562 A | 11/1993 | Matteucci |
| 5,322,841 A | 6/1994 | Jamas et al. |
| 5,401,727 A | 3/1995 | Rorstad et al. |
| 5,405,939 A | 4/1995 | Suhadolnik |
| 5,416,203 A | 5/1995 | Letsinger |
| 5,417,978 A | 5/1995 | Tari et al. |
| 5,432,272 A | 7/1995 | Benner |
| 5,453,496 A | 9/1995 | Caruthers et al. |
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,504,079 A | 4/1996 | Jamas et al. |
| 5,512,667 A | 4/1996 | Reed et al. |
| 5,514,786 A | 5/1996 | Cook et al. |

(Continued)

FOREIGN PATENT DOCUMENTS

| | | |
|---|---|---|
| AU | 2004206255 B2 | 8/2004 |
| CN | 1 568 373 A | 1/2005 |

(Continued)

OTHER PUBLICATIONS

[No Author Listed] Rxi Pharmaceutical Corporation. Ex 99.1. OTC: RXII. Mar. 2013. 38 pages.

(Continued)

*Primary Examiner* — Sean McGarry
(74) *Attorney, Agent, or Firm* — Wolf, Greenfield & Sacks, P.C.

(57) ABSTRACT

The present invention relates to RNAi constructs with improved tissue and cellular uptake characteristics and methods of use of these compounds in dermal applications.

4 Claims, 9 Drawing Sheets

Specification includes a Sequence Listing.

(56) References Cited

U.S. PATENT DOCUMENTS

| | | |
|---|---|---|
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,677 A | 3/1997 | Jamas et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,466,786 B1 | 4/1998 | Buhr et al. |
| 5,736,392 A | 4/1998 | Hawley-Nelson et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,789,416 A | 8/1998 | Lum et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,830,653 A | 11/1998 | Froehler et al. |
| 5,849,902 A | 12/1998 | Arrow et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,968,811 A | 10/1999 | Greenshields |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev |
| 6,153,737 A | 11/2000 | Manoharan et al. |
| 6,207,819 B1 | 3/2001 | Manoharan et al. |
| 6,221,911 B1 | 4/2001 | Lavin et al. |
| 6,242,594 B1 | 6/2001 | Kelly |
| 6,248,878 B1 | 6/2001 | Matulic-Adamic et al. |
| 6,271,358 B1 | 8/2001 | Manoharan et al. |
| 6,326,358 B1 | 12/2001 | Manoharan |
| 6,331,617 B1 | 12/2001 | Weeks et al. |
| 6,335,434 B1 | 1/2002 | Guzaev et al. |
| 6,355,787 B1 | 3/2002 | Beckvermit et al. |
| 6,358,931 B1 | 3/2002 | Cook et al. |
| 6,395,492 B1 | 5/2002 | Manoharan et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,440,943 B1 | 8/2002 | Cook et al. |
| 6,444,448 B1 | 9/2002 | Wheatcroft et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,003 B1 | 11/2002 | Jordan et al. |
| 6,476,205 B1 | 11/2002 | Buhr et al. |
| 6,506,559 B1 | 1/2003 | Fire et al. |
| 6,528,631 B1 | 3/2003 | Cook et al. |
| 6,531,584 B1 | 3/2003 | Cook et al. |
| 6,673,611 B2 | 1/2004 | Thompson et al. |
| 6,683,167 B2 | 1/2004 | Meteley et al. |
| 6,794,137 B2 | 9/2004 | Blumenberg |
| 6,815,432 B2 | 11/2004 | Wheeler et al. |
| 6,849,726 B2 | 2/2005 | Usman et al. |
| 6,858,225 B2 | 2/2005 | Semple et al. |
| 7,041,824 B2 | 5/2006 | Bordon-Pallier et al. |
| 7,044,945 B2 | 5/2006 | Sand |
| 7,056,704 B2 | 6/2006 | Tuschl et al. |
| 7,078,196 B2 | 7/2006 | Tuschl et al. |
| 7,087,743 B2 | 8/2006 | Kurfurst et al. |
| 7,098,190 B1 | 8/2006 | Becker et al. |
| 7,108,721 B2 | 9/2006 | Huckle et al. |
| 7,205,297 B2 | 4/2007 | Beauchamp et al. |
| 7,405,274 B2 | 7/2008 | Lin et al. |
| 7,432,250 B2 | 10/2008 | Crooke |
| 7,538,095 B2 | 5/2009 | Fire et al. |
| 7,560,438 B2 | 7/2009 | Fire et al. |
| 7,579,186 B1 | 8/2009 | Sakamoto et al. |
| 7,595,387 B2 | 9/2009 | Leake et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,829,693 B2 | 11/2010 | Kreutzer et al. |
| 8,110,674 B2 | 2/2012 | Manoharan et al. |
| 8,168,600 B2 | 5/2012 | Dokka et al. |
| 8,263,569 B2 | 9/2012 | Baulcombe et al. |
| 8,329,671 B2 | 12/2012 | Gu et al. |
| 8,410,260 B2 * | 4/2013 | Collin-Djangone ... A61K 8/606 536/24.5 |
| 8,486,909 B2 | 7/2013 | Rennard et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 8,822,428 B2 * | 9/2014 | Collin-Djangone ... A61K 8/606 514/44 A |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |
| 10,138,485 B2 | 11/2018 | Khvorova et al. |
| 10,167,471 B2 | 1/2019 | Kamens et al. |
| 10,184,124 B2 | 1/2019 | Libertine et al. |
| 10,240,149 B2 | 3/2019 | Khvorova et al. |
| 10,300,027 B2 | 5/2019 | Levis et al. |
| 10,479,992 B2 | 11/2019 | Woolf et al. |
| 10,633,654 B2 | 4/2020 | Pavco et al. |
| 10,662,430 B2 | 5/2020 | Libertine et al. |

(56) References Cited

U.S. PATENT DOCUMENTS

| | | |
|---|---|---|
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0216346 A1 | 11/2003 | Sakurai et al. |
| 2004/0009938 A1 | 1/2004 | Manoharan et al. |
| 2004/0014715 A1 | 1/2004 | Ostroff |
| 2004/0014956 A1 | 1/2004 | Woolf et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0087526 A1 | 5/2004 | Lin et al. |
| 2004/0137471 A1 | 7/2004 | Vickers et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0229266 A1 | 11/2004 | Tuschl et al. |
| 2004/0235031 A1 | 11/2004 | Schultz et al. |
| 2004/0241845 A1 | 12/2004 | Desgroseillers et al. |
| 2004/0259247 A1 | 12/2004 | Tuschl et al. |
| 2005/0032733 A1 | 2/2005 | McSwiggen et al. |
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0181382 A1 | 8/2005 | Zamore et al. |
| 2005/0222071 A1 | 10/2005 | Duranton et al. |
| 2005/0233997 A1 | 10/2005 | Richards et al. |
| 2005/0245474 A1 | 11/2005 | Baker et al. |
| 2005/0246794 A1 | 11/2005 | Khvorova et al. |
| 2005/0255487 A1* | 11/2005 | Khvorova ............ A61K 31/713 435/6.11 |
| 2005/0281781 A1 | 12/2005 | Ostroff |
| 2006/0009409 A1 | 1/2006 | Woolf |
| 2006/0025363 A1 | 2/2006 | Breitenbach et al. |
| 2006/0069050 A1 | 3/2006 | Rana |
| 2006/0142228 A1 | 6/2006 | Ford et al. |
| 2006/0178324 A1 | 8/2006 | Hadwiger et al. |
| 2006/0178327 A1 | 8/2006 | Yeung |
| 2007/0020623 A1 | 1/2007 | Petersohn et al. |
| 2007/0032441 A1 | 2/2007 | McSwiggen et al. |
| 2007/0166734 A1 | 7/2007 | Bhat et al. |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0071068 A1 | 3/2008 | Oba et al. |
| 2008/0085869 A1 | 4/2008 | Yamada et al. |
| 2008/0182808 A1 | 7/2008 | Breitenbach et al. |
| 2008/0311040 A1 | 12/2008 | Berry et al. |
| 2009/0023216 A1 | 1/2009 | Woolf |
| 2009/0202458 A1* | 8/2009 | Binetti ................. C12N 15/111 424/60 |
| 2009/0202520 A1 | 8/2009 | Lupher, Jr. et al. |
| 2009/0208564 A1 | 8/2009 | Li et al. |
| 2009/0239934 A1 | 9/2009 | Schmitt-Milas |
| 2009/0247608 A1 | 10/2009 | Manoharan et al. |
| 2010/0040656 A1 | 2/2010 | Franklin et al. |
| 2010/0136695 A1 | 6/2010 | Woolf |
| 2011/0039914 A1 | 2/2011 | Pavco et al. |
| 2011/0054004 A1 | 3/2011 | Mustoe et al. |
| 2011/0237522 A1 | 9/2011 | Khvorova et al. |
| 2011/0263680 A1 | 10/2011 | Khvorova et al. |
| 2011/0268761 A1 | 11/2011 | Levis et al. |
| 2011/0294869 A1 | 12/2011 | Petersen |
| 2012/0040459 A1 | 2/2012 | Khvorova et al. |
| 2013/0195966 A1* | 8/2013 | Collin-Djangone ... A61K 8/606 424/450 |
| 2014/0072613 A1 | 3/2014 | Lander et al. |
| 2015/0057362 A1 | 2/2015 | Levis et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304873 A1 | 10/2016 | Wolfson et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0022501 A1 | 1/2017 | Dean et al. |
| 2017/0051288 A1 | 2/2017 | Byrne et al. |
| 2017/0051290 A1 | 2/2017 | Byrne et al. |
| 2017/0067056 A1 | 3/2017 | Khvorova et al. |
| 2017/0137823 A1 | 5/2017 | Kamens et al. |
| 2018/0155718 A1 | 6/2018 | Woolf et al. |
| 2018/0195066 A1 | 7/2018 | Byrne et al. |
| 2018/0195072 A1 | 7/2018 | Cardia et al. |
| 2018/0263925 A1 | 9/2018 | Cauwenbergh et al. |
| 2018/0327748 A1 | 11/2018 | Khvorova et al. |
| 2018/0371464 A1 | 12/2018 | Khvorova et al. |
| 2019/0029974 A1 | 1/2019 | Cauwenbergh et al. |
| 2019/0048341 A1 | 2/2019 | Cardia et al. |
| 2019/0161757 A1 | 5/2019 | Khvorova et al. |
| 2019/0169608 A1 | 6/2019 | Pavco et al. |
| 2019/0211337 A1 | 7/2019 | Khvorova et al. |
| 2019/0218557 A1 | 7/2019 | Kamens et al. |
| 2019/0233826 A1 | 8/2019 | Libertine et al. |
| 2020/0085764 A1 | 3/2020 | Maxwell et al. |
| 2020/0101028 A1 | 4/2020 | Levis et al. |
| 2020/0215113 A1 | 7/2020 | Eliseev |

FOREIGN PATENT DOCUMENTS

| | | |
|---|---|---|
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| EP | 2 719 762 A1 | 4/2014 |
| JP | 4 095 895 B2 | 9/2004 |
| JP | 2007-512377 A | 5/2007 |
| JP | 2007-525169 A | 9/2007 |
| JP | 2007-531520 A | 11/2007 |
| JP | 2009-519033 | 5/2009 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/08003 A1 | 4/1994 |
| WO | WO 94/23028 A2 | 10/1994 |
| WO | WO 95/11910 A1 | 5/1995 |
| WO | WO 95/22553 A1 | 8/1995 |
| WO | WO 95/23162 A1 | 8/1995 |
| WO | WO 96/40964 A2 | 12/1996 |
| WO | WO 99/13915 A1 | 3/1999 |
| WO | WO 02/12348 A2 | 2/2002 |
| WO | WO 03/012052 A2 | 2/2003 |
| WO | WO 2003/064626 A2 | 8/2003 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/051971 A1 | 6/2005 |
| WO | WO 2005/079533 A2 | 9/2005 |
| WO | WO 2005/097992 A2 | 10/2005 |
| WO | WO 2006/007372 A2 | 1/2006 |
| WO | WO 2006/019430 A2 | 2/2006 |
| WO | WO 2006/039656 A2 | 4/2006 |
| WO | WO 2006/065601 A2 | 6/2006 |
| WO | WO 2006/128141 A2 | 11/2006 |
| WO | WO 2007/030167 A1 | 3/2007 |
| WO | WO 2007/050643 A2 | 5/2007 |
| WO | WO 2007/069068 A2 | 6/2007 |
| WO | WO 2007/089607 A2 | 8/2007 |
| WO | WO 2008/021157 A1 | 2/2008 |
| WO | WO 2008/036825 A2 | 3/2008 |

(56) References Cited

FOREIGN PATENT DOCUMENTS

| WO | WO 2008/109353 A1 | 9/2008 |
|----|-------------------|--------|
| WO | WO 2009/020344 A2 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/126933 A2 | 10/2009 |
| WO | WO 2009/134487 A2 | 11/2009 |
| WO | WO 2010/006237 A2 | 1/2010 |
| WO | WO 2010/011346 A2 | 1/2010 |
| WO | WO 2010/027830 A2 | 3/2010 |
| WO | WO 2010/027831 A1 | 3/2010 |
| WO | WO 2010/027832 A1 | 3/2010 |
| WO | WO 2010/042281 A2 | 4/2010 |
| WO | WO 2012/106508 A1 | 8/2012 |
| WO | WO 2015/085113 A1 | 6/2015 |
| WO | WO 2017/017523 A1 | 2/2017 |

OTHER PUBLICATIONS

Augustyns et al., Incorporation of hexose nucleoside analogues into oligonucleotides: synthesis, base-pairing properties and enzymatic stability. Nucleic Acids Res. Sep. 25, 1992;20(18):4711-6.

Bergan et al., Electroporation enhances c-myc antisense oligodeoxynucleotide efficacy. Nucleic Acids Res. Jul. 25, 1993;21(15):3567-73.

Caruthers et al., Chemical and biochemical studies with dithioate DNA. Nucleosides & Nucleotides. 1991;10(1-3):47-59.

Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.

Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.

Chiang et al., Antisense oligonucleotides inhibit intercellular adhesion molecule 1 expression by two distinct mechanisms. J Biol Chem. Sep. 25, 1991;266(27):18162-71.

Collins et al., Diagnosis and treatment of venous ulcers. Am Fam Physician. Apr. 15, 2010;81(8):989-96.

Dye et al., The population dynamics and control of tuberculosis. Science. May 14, 2010;328(5980):856-61. doi: 10.1126/science. 1185449.

Eichelbaum et al., Influence of pharmacogenetics on drug disposition and response. Clin Exp Pharmacol Physiol. Oct.-Nov. 1996;23(10-11):983-5. Review.

Elkington et al., MMP-1 drives immunopathology in human tuberculosis and transgenic mice. J Clin Invest. May 2011;121(5):1827-33. doi: 10.1172/JCI45666. Epub Apr. 25, 2011.

Fabbrocini et al., Acne Scars: Pathogenesis, Classification and Treatment. Dermatology Research and Practice, vol. 2010, Article ID 893080, 13 pages, 2010. doi: 10.1155/2010/893080. 13 pages.

Glaser, Oligonucleotide therapies move toward efficacy trials to treat HIV CMV, cancer. Genetic Engineering News. Feb. 1, 2016;16:1-21.

Hartong et al., Retinitis pigmentosa. Lancet. Nov. 18, 2006;368(9549):1795-809.

Hope et al., Cationic lipids, phosphatidylethanolamine and the intracellular delivery of polymeric, nucleic acid-based drugs (review). Mol Membr Biol. Jan.-Mar. 1998;15(1):1-14.

Hudelist et al., Interleukin 1alpha and tissue-lytic matrix metalloproteinase-1 are elevated in ectopic endometrium of patients with endometriosis. Hum Reprod. Jun. 2005;20(6):1695-701. Epub Mar. 3, 2005.

Iannone et al., The pathophysiology of osteoarthritis. Aging Clin Exp Res. Oct. 2003;15(5):364-72.

Kamata et al., Amphiphilic peptides enhance the efficiency of liposome-mediated DNA transfection. Nucleic Acids Res. Feb. 11, 1994;22(3):536-7.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Li et al., Yeast glucan particles activate murine resident macrophages to secrete proinflammatory cytokines via MyD88- and Syk kinase-dependent pathways. Clin Immunol. Aug. 2007;124(2):170-81. Epub Jun. 14, 2007.

Linder et al., Pharmacogenetics: a laboratory tool for optimizing therapeutic efficiency. Clin Chem. Feb. 1997;43(2):254-66. Review.

Nishioka et al., A single nucleotide polymorphism in the matrix metalloproteinase-1 promoter in endometrial carcinomas. Jpn J Cancer Res. Jun. 2000;91(6):612-5.

Ortigão et al., Antisense effect of oligodeoxynucleotides with inverted terminal internucleotidic linkages: a minimal modification protecting against nucleolytic degradation. Antisense Res Dev. 1992 Summer;2(2):129-46.

Ramamurthi et al., Pathogenesis, clinical features and management of recurrent corneal erosions. Eye (Lond). Jun. 2006;20(6):635-44. Epub Jul. 15, 2005.

Reichhart et al., Splice-activated UAS hairpin vector gives complete RNAi knockout of single or double target transcripts in *Drosophila melanogaster*. Genesis. Sep.-Oct. 2002;34(1-2):160-4.

Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.

Snead et al., RNA interference trigger variants: getting the most out of RNA for RNA interference-based therapeutics. Nucleic Acid Ther. Jun. 2012;22(3):139-46. doi: 10.1089/nat.2012.0361. Review.

Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.

Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.

Sriram et al., Reduction of corneal scarring in rabbits by targeting the TGFB1 pathway with a triple siRNA combination. Adv Biosci Biotechnol. Jan. 1, 2013;4(10):47-55.

Sriram et al., Triple combination of siRNAs targeting TGFβ1, TGFβR2, and CTGF enhances reduction of collagen I and smooth muscle actin in corneal fibroblasts. Invest Ophthalmol Vis Sci. Dec. 17, 2013;54(13):8214-23. doi: 10.1167/iovs.13-12758.

Stein et al., A specificity comparison of four antisense types: morpholino, 2'-O-methyl RNA, DNA, and phosphorothioate DNA. Antisense Nucleic Acid Drug Dev. Jun. 1997;7(3):151-7.

Sui et al., A DNA vector-based RNAi technology to suppress gene expression in mammalian cells. Proc Natl Acad Sci U S A. Apr. 16, 2002;99(8):5515-20.

Summerton et al., Morpholino and phosphorothioate antisense oligomers compared in cell-free and in-cell systems. Antisense Nucleic Acid Drug Dev. Apr. 1997;7(2):63-70.

Vashi et al., Facial hyperpigmentation: causes and treatment. Br J Dermatol. Oct. 2013;169 Suppl 3:41-56. doi: 10.1111/bjd.12536.

Vlassov et al., Transport of oligonucleotides across natural and model membranes. Biochim Biophys Acta. Jun. 29, 1994;1197(2):95-108.

Wagner et al., Transferrin-polycation-DNA complexes: the effect of polycations on the structure of the complex and DNA delivery to cells. Proc Natl Acad Sci U S A. May 15, 1991;88(10):4255-9.

Wolfrum et al., Mechanisms and optimization of in vivo delivery of lipophilic siRNAs. Nat Biotechnol. Oct. 2007;25(10):1149-57. Epub Sep. 16, 2007.

Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.

Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.

(56) References Cited

OTHER PUBLICATIONS

U.S. Appl. No. 15/638,586, filed Jun. 30, 2017, Woolf et al.
U.S. Appl. No. 15/532,804, filed Jun. 2, 2017, Cauwenbergh et al.
PCT/US15/48565, Nov. 18, 2015, Invitation to Pay Additional Fees.
PCT/US15/48565, Feb. 8, 2016, International Search Report and Written Opinion.
[No Author Listed] RedChip Small-Cap Investor Conference. RXI Pharmaceuticals (Nasdaq RXII). Jun. 16, 2009 Presentation. 22 pages.
[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].
Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Aleckovic et al., J RNAi Gene Silencing. May 27, 2008;4(1):266-8.
Aouadi et al., Orally delivered siRNA targeting macrophage Map4k4 suppresses systemic inflammation. Nature. Apr. 30, 2009;458(7242):1180-4. doi: 10.1038/nature07774.
Baigude et al., Design and creation of new nanomaterials for therapeutic RNAi. ACS Chem Biol. Apr. 24, 2007;2(4):237-41.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA interference in mammalian cells by chemically-modified RNA. Biochemistry. Jul. 8, 2003;42(26):7967-75.
Brown et al., RNAi off-targeting: Light at the end of the tunnel. J RNAi Gene Silencing. Jul. 28, 2006;2(2):175-7.
Cardia et al., Novel self-delivering RNAi compounds with enhanced cellular updatake and distribution properties. Keystone RNAi Silencing Conference. Jan. 14-19, 2010. Poster. 1 Page.
Choi et al., Control of scarring in adult wounds using antisense transforming growth factor-beta 1 oligodeoxynucleotides. Immunol Cell Biol. Apr. 1996;74(2):144-50.
Choung et al., Chemical modification of siRNAs to improve serum stability without loss of efficacy. Biochem Biophys Res Commun. Apr. 14, 2006;342(3):919-27.
Chu et al., Potent RNAi by short RNA triggers. RNA. 2008;14:1714-9.
Cordeiro et al., Novel antisense oligonucleotides targeting TGF-beta inhibit in vivo scarring and improve surgical outcome. Gene Ther. Jan. 2003;10(1):59-71.
Czauderna et al., ., Structural variations and stabilising modifications of synthetic siRNAs in mammalian cells. Nucleic Acids Res. Jun. 1, 2003;31(11):2705-16.
De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Distler et al., Imatinib mesylate reduces production of extracellular matrix and prevents development of experimental dermal fibrosis. Arthritis Rheum. Jan. 2007;56(1):311-22.
Dykxhoorn et al., The silent treatment: siRNAs as small molecule drugs. Gene Ther. Mar. 2006;13(6):541-52. Review.
Dziadzio et al., N-terminal connective tissue growth factor is a marker of the fibrotic phenotype in scleroderma. QJM. Jul. 2005;98(7):485-92. Epub Jun. 13, 2005.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in *Drosophila melanogaster* embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Ferguson et al., Scar-free healing: from embryonic mechanisms to adult therapeutic intervention. Philos Trans R Soc Lond B Biol Sci. May 29, 2004;359(1445):839-50.
Fisher et al., Intracellular disposition and metabolism of fluorescently-labeled unmodified and modified oligonucleotides microinjected into mammalian cells. Nucleic Acids Res. Aug. 11, 1993;21(16):3857-65.
Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.
Ito et al., Expression of connective tissue growth factor in human renal fibrosis. Kidney Int. Apr. 1998;53(4):853-61.
Jackson et al., Position-specific chemical modification of siRNAs reduces "off-target" transcript silencing. RNA. Jul. 2006;12(7):1197-1205. Epub May 8, 2006.
Kamens et al., Novel, chemically modified RNAi compounds with improved potency, stability and specificity. Keystone RNAi Silencing: Mechanism, Biology and Application Conference. Jan. 14-19, 2010. Poster. 1 Page.
Kim et al., Systemic and specific delivery of small interfering RNAs to the liver mediated by apolipoprotein A-I. Mol Ther. Jun. 2007;15(6):1145-52. Epub Apr. 17, 2007.
Koitabashi et al., Plasma connective tissue growth factor is a novel potential biomarker of cardiac dysfunction in patients with chronic heart failure. Eur J Heart Fail. Apr. 2008;10(4):373-9. doi: 10.1016/j.ejheart.2008.02.011.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and longterm RNAi activity. Oligonucleotides. 2007 Winter;17(4):445-64.
Layzer et al., In vivo activity of nuclease-resistant siRNAs. RNA. May 2004;10(5):766-71.
Leask et al., Insights into the molecular mechanism of chronic fibrosis: the role of connective tissue growth factor in scleroderma. J Invest Dermatol. Jan. 2004;122(1):1-6.
Lee et al.,., Contributions of 3'-overhang to the dissociation of small interfering RNAs from the PAZ domain: molecular dynamics simulation study. J Mol Graph Model. Mar. 2007;25(6):784-93. Epub Jul. 11, 2006.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Reports 2006;7(3):314-20.
Li et al., Surface-modified LPD nanoparticles for tumor targeting. Ann N Y Acad Sci. Oct. 2006;1082:1-8.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.

(56) References Cited

OTHER PUBLICATIONS

Niessen et al., Keratinocyte-derived growth factors play a role in the formation of hypertrophic scars. J Pathol. Jun. 2001;194(2):207-16.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Overhoff et al., Phosphorothioate-stimulated uptake of short interfering RNA by human cells. EMBO Rep. Dec. 2005;6(12):1176-81.
Parrish et al., Functional anatomy of a dsRNA trigger: differential requirement for the two trigger strands in RNA interference. Mol Cell. Nov. 2000;6(5):1077-87.
Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.
Rajeev et al., 2'-modified-2-thiothymidine oligonucleotides. Org Lett. Aug. 21, 2003;5(17):3005-8.
Rozners et al., Expanding functionality of RNA: synthesis and properties of RNA containing imidazole modified tandem G-U wobble base pairs. Chem Commun (Camb). Dec. 14, 2005;(46):5778-80.
Rump et al., Preparation of conjugates of oligodeoxynucleotides and lipid structures and their interaction with low-density lipoprotein. Bioconjug Chem. May-Jun. 1998;9(3):341-9.
Sadick et al., TGF-beta1 antisense therapy modulates expression of matrix metalloproteinases in keloid-derived fibroblasts. Int J Mol Med. Jul. 2008;22(1):55-60.
Salomon et al., Modified dsRNAs that are not processed by Dicer maintain potency and are incorporated into the Risc. Nucleic Acids Res. Jun. 2010;38(11):3771-9. doi: 10.1093/nar/gkq055. Epub Feb. 18, 2010.
Sato et al., Serum levels of connective tissue growth factor are elevated in patients with systemic sclerosis: association with extent of skin sclerosis and severity of pulmonary fibrosis. J Rheumatol. Jan. 2000;27(1):149-54.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Shah et al., Neutralisation of TGF-beta 1 and TGF-beta 2 or exogenous addition of TGF-beta 3 to cutaneous rat wounds reduces scarring. J Cell Sci. Mar. 1995;108 ( Pt 3):985-1002.
Shi, Mammalian RNAi for the masses. Trends Genet. Jan. 2003;19(1):9-12.
Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytogfr.2008.01.002.
Sisco et al., Antisense inhibition of connective tissue growth factor (CTGF/CCN2) mRNA limits hypertrophic scarring without affecting wound healing in vivo. Wound Repair Regen. Sep.-Oct. 2008;16(5):661-73. doi: 10.1111/j.1524-475X.2008.00416.x.
Soutschek et al., Therapeutic silencing of an endogenous gene by systemic administration of modified siRNAs. Nature. Nov. 11, 2004;432(7014):173-8.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.
Takanashi et al., Therapeutic silencing of an endogenous gene by siRNA cream in an arthritis model mouse. Gene Ther. Aug. 2009;16(8):982-9. doi: 10.1038/gt.2009.66. Epub May 28, 2009.
Uhlmann et al., Antisense oligonucleotides: a new therapeutic principle. Chem Rev. 1990;90(4):543-84.
Vaught et al., Expanding the chemistry of DNA for in vitro selection. J Am Chem Soc. Mar. 31, 2010;132(12):4141-51. doi: 10.1021/ja908035g.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.
Zhang et al., Mechanisms of hypoxic regulation of plasminogen activator inhibitor-1 gene expression in keloid fibroblasts. J Invest Dermatol. Nov. 2003;121(5):1005-12.
U.S. Appl. No. 16/153,424, filed Oct. 5, 2018, Pavco et al.
U.S. Appl. No. 16/191,396, filed Nov. 14, 2018, Kamens et al.
U.S. Appl. No. 16/159,590, filed Oct. 12, 2018, Khvorova et al.
U.S. Appl. No. 16/270,524, filed Feb. 7, 2019, Khvorova et al.
U.S. Appl. No. 16/206,064, filed Nov. 30, 2018, Libertine et al.
U.S. Appl. No. 16/377,617, filed Apr. 8, 2019, Levis et al.
EP 15837293.8, Apr. 6, 2018, Partial Supplementary European Search Report.
EP 15837293.8, Jul. 25, 2018, Extended European Search Report.
PCT/US2015/048565, Mar. 16, 2017, International Preliminary Report on Patentability.
Cardia et al., Self-Delivering RNAi Compounds. Drug Delivery Technology. Sep. 2010;10(7):1-4.
Chiu et al., siRNA function in RNAi: a chemical modification analysis. RNA. Sep. 2003;9(9):1034-48.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
U.S. Appl. No. 16/680,101, filed Nov. 11, 2019, Woolf et al.
U.S. Appl. No. 16/637,514, filed Feb. 7, 2020, Eliseev.
Chernikov et al., Current Development of siRNA Bioconjugates: From Research to the Clinic. Front Pharmacol. Apr. 26, 2019; 10:444. doi: 10.3389/fphar.2019.00444.
Holton et al., Self-delivering RNAi Compounds Targeting Collagenase I. RXI Pharmaceuticals. Society for Investigative Dermatology (SID) 74th Annual Meeting. May 9, 2015. Poster. 1 page.
Maxwell et al., Tyrosinase Targeting Self-delivering RNAi Compounds. RXI Pharmaceuticals. Society for Investigative Dermatology (SID) 74th Annual Meeting. May 9, 2015. Poster. 1 page.
Opalinska et al., Nucleic-acid therapeutics: basic principles and recent applications. Nat Rev Drug Discov. Jul. 2002; 1(7):503-14.
Slowminski et al., Inhibitors of melanogenesis increase toxicity of cyclophosphamide and lymphocytes against melanoma cells. Int J Cancer. Mar. 15, 2009; 124(6):1470-7. doi: 10.1002/ijc.24005.

\* cited by examiner

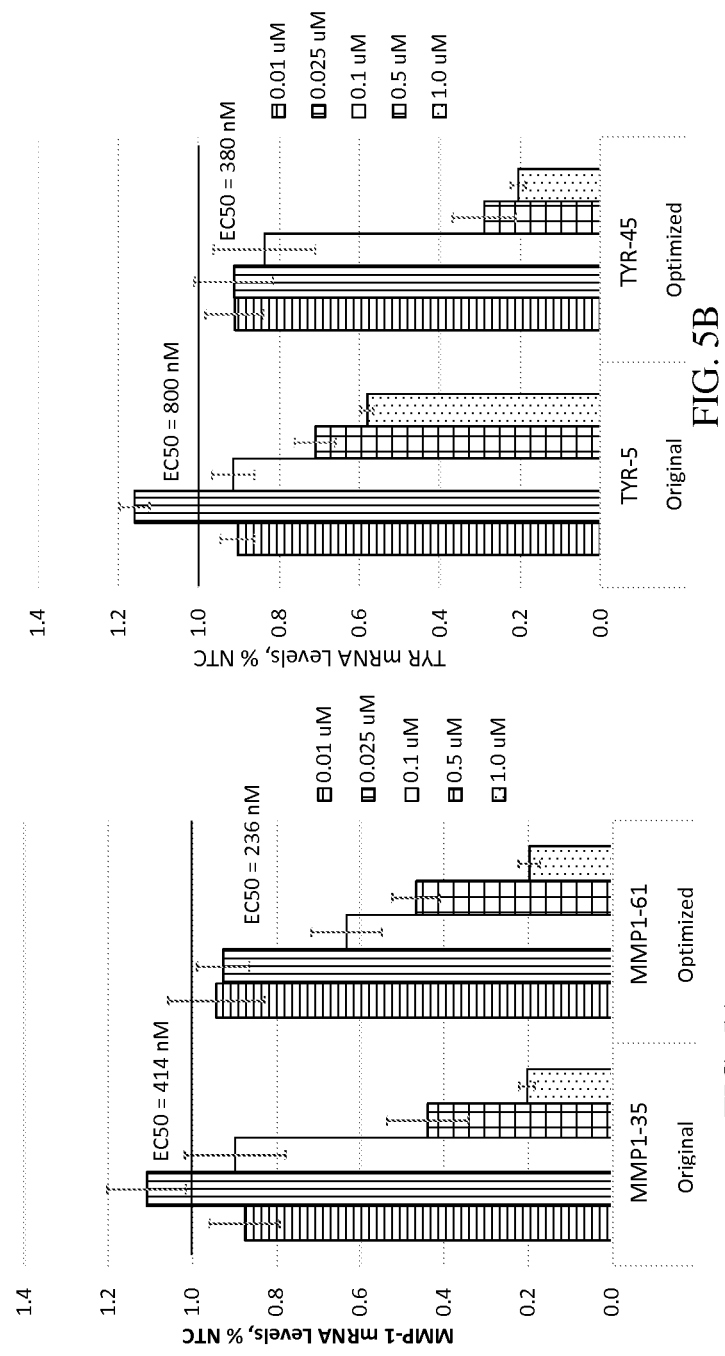

Reduction of MMP1 mRNA Results in Dose Dependent Reduction of MMP1 Enzyme Activity

SEQUENCE LISTING

<160> NUMBER OF SEQ ID NOS: 302

<210> SEQ ID NO 1
<211> LENGTH: 2081
<212> TYPE: DNA
<213> ORGANISM: Homo sapiens

<400> SEQUENCE: 1

```
agcatgagtc agacagcctc tggctttctg gaagggcaag gactctatat atacagaggg      60
agcttcctag ctgggatatt ggagcagcaa gaggctggga agccatcact taccttgcac     120
tgagaaagaa gacaaaggcc agtatgcaca gctttcctcc actgctgctg ctgctgttct     180
ggggtgtggt gtctcacagc ttcccagcga ctctagaaac acaagagcaa gatgtggact     240
tagtccagaa atacctggaa aaatactaca acctgaagaa tgatgggagg caagttgaaa     300
agcggagaaa tagtggccca gtggttgaaa aattgaagca aatgcaggaa ttctttgggc     360
tgaaagtgac tgggaaacca gatgctgaaa ccctgaaggt gatgaagcag cccagatgtg     420
gagtgcctga tgtggctcag tttgtcctca ctgaggggaa cctcgctgg gagcaaacac      480
atctgaccta caggattgaa aattacacgc cagatttgcc aagagcagat gtggaccatg     540
ccattgaaaa agccttccaa ctctggagta atgtcacacc tctgacattc accaaggtct     600
ctgagggtca agcagacatc atgatatctt ttgtcagggg agatcatcgg gacaactctc     660
cttttgatgg acctggagga aatcttgctc atgcttttca accaggccca ggtattggag     720
gggatgctca ttttgatgaa gatgaaaggt ggaccaacaa tttcagagag tacaacttac     780
atcgtgttgc agctcatgaa ctcggccatt ctcttggact ctcccattct actgatatcg     840
gggctttgat gtaccctagc tacaccttca gtggtgatgt tcagctagct caggatgaca     900
ttgatggcat ccaagccata tatggacgtt cccaaaatcc tgtccagccc atcggcccac     960
aaacccccaa agcgtgtgac agtaagctaa cctttgatgc tataactacg attcggggag    1020
aagtgatgtt ctttaaagac agattctaca tgcgcacaaa tccttctac ccggaagttg    1080
agctcaattt catttctgtt ttctggccac aactgccaaa tgggcttgaa gctgcttacg    1140
aatttgccga cagagatgaa gtccggtttt tcaaagggaa taagtactgg gctgttcagg    1200
gacagaatgt gctacacgga taccccaagg acatctcag ctcctttggc ttccctagaa     1260
ctgtgaagca tatcgatgct gctctttctg aggaaaacac tggaaaaacc tacttctttg    1320
ttgctaacaa atactggagg tatgatgaat ataaacgatc tatggatcca ggttatccca    1380
aaatgatagc acatgacttt cctggaattg ccacaaagt tgatgcagtt ttcatgaaag    1440
atggatttt ctatttcttt catggaacaa gacaatacaa atttgatcct aaaacgaaga    1500
gaattttgac tctccagaaa gctaatagct ggttcaactg caggaaaaat tgaacattac    1560
taatttgaat ggaaaacaca tggtgtgagt ccaaagaagg tgttttcctg aagaactgtc    1620
tattttctca gtcatttta acctctagag tcactgatac acagaatata atcttattta    1680
tacctcagtt tgcatatttt tttactattt agaatgtagc ccttttgta ctgatataat    1740
ttagttccac aaatggtggg tacaaaaagt caagtttgtg gcttatggat tcatataggc    1800
```

-continued

```
cagagttgca aagatctttt ccagagtatg caactctgac gttgatccca gagagcagct    1860
tcagtgacaa acatatcctt tcaagacaga aagagacagg agacatgagt ctttgccgga    1920
ggaaaagcag ctcaagaaca catgtgcagt cactggtgtc accctggata ggcaagggat    1980
aactcttcta acacaaaata agtgttttat gtttggaata aagtcaacct tgtttctact    2040
gttttataca ctttcaaaaa aaaaaaaaaa aaaaaaaaaa a                         2081

<210> SEQ ID NO 2
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 2
ccuacaggau uga                                                         13

<210> SEQ ID NO 3
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 3
uacaggauug aaa                                                         13

<210> SEQ ID NO 4
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 4
aggauugaaa aua                                                         13

<210> SEQ ID NO 5
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 5
ugaaaauuac aca                                                         13

<210> SEQ ID NO 6
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 6
gaaaggugga cca                                                         13

<210> SEQ ID NO 7
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 7
```

-continued

```
aaagguggac caa                                                          13

<210> SEQ ID NO 8
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 8
ugauguucag cua                                                          13

<210> SEQ ID NO 9
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 9 accuugaug cua                                                           13

<210> SEQ ID NO 10
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 10
uuugaugcua uaa                                                          13

<210> SEQ ID NO 11
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 11
uugaugcuau aaa                                                          13

<210> SEQ ID NO 12
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 12
ugaugcuaua aca                                                          13

<210> SEQ ID NO 13
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 13
acaugcgcac aaa                                                          13

<210> SEQ ID NO 14
<211> LENGTH: 13
<212> TYPE: RNA
```

```
<213> ORGANISM: Artificial Sequence
<220> FEATURE:
<223> OTHER INFORMATION: Synthetic Polynucleotide

<400> SEQUENCE: 14
augcgcacaa aua                                                    13

<210> SEQ ID NO 15
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 15
augaaguccg gua                                                    13

<210> SEQ ID NO 16
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 16
ugaaguccgg uua                                                    13

<210> SEQ ID NO 17
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 17
guccgguuuu uca                                                    13

<210> SEQ ID NO 18
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 18
uccgguuuuu caa                                                    13

<210> SEQ ID NO 19
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 19
ccgguuuuuc aaa                                                    13

<210> SEQ ID NO 20
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 20
cgguuuuuca aaa                                                    13
```

-continued

<210> SEQ ID NO 21
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 21 gguuuucaa aga                                                         13

<210> SEQ ID NO 22
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 22
ggagguauga uga                                                        13

<210> SEQ ID NO 23
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 23
gagguaugau gaa                                                        13

<210> SEQ ID NO 24
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 24
agguaugaug aaa                                                        13

<210> SEQ ID NO 25
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 25
guaugaugaa uaa                                                        13

<210> SEQ ID NO 26
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 26
augaugaaua uaa                                                        13

<210> SEQ ID NO 27
<211> LENGTH: 13
<212> TYPE: RNA
<213> ORGANISM: Artificial Sequence
<220> FEATURE:

<223> OTHER INFORMATION: Synthetic Polynucleotide

<400> SEQUENCE: 27
augaauauaa aca                                                              13

<210> SEQ ID NO 28
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 28
gauccagguu aua                                                              13

<210> SEQ ID NO 29
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 29
auccagguua uca                                                              13

<210> SEQ ID NO 30
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 30
ccaaaaugau aga                                                              13

<210> SEQ ID NO 31
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 31
caaaaugaua gca                                                              13

<210> SEQ ID NO 32
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 32
aaaaugauag caa                                                              13

<210> SEQ ID NO 33
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 33
uuccuggaau uga                                                              13

-continued

```
<210> SEQ ID NO 34
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 34
uaauagcugg uua                                                          13

<210> SEQ ID NO 35
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 35
aauagcuggu uca                                                          13

<210> SEQ ID NO 36
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 36
auagcugguu caa                                                          13

<210> SEQ ID NO 37
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 37
uagcugguuc aaa                                                          13

<210> SEQ ID NO 38
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 38
agcugguuca aca                                                          13

<210> SEQ ID NO 39
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 39
gcugguucaa cua                                                          13

<210> SEQ ID NO 40
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 40
cugguucaac uga                                                          13

<210> SEQ ID NO 41
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 41
ugguucaacu gca                                                          13

<210> SEQ ID NO 42
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 42
gguucaacug caa                                                          13

<210> SEQ ID NO 43
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 43
ucaauccugu aggucagau                                                    19

<210> SEQ ID NO 44
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 44
uuucaauccu guaggucag                                                    19

<210> SEQ ID NO 45
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 45
uauuuucaau ccuguaggu                                                    19

<210> SEQ ID NO 46
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 46
uguguaauuu ucaauccug                                                    19

<210> SEQ ID NO 47
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 47
ugguccaccu uucaucuuc                                              19

<210> SEQ ID NO 48
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 48
uugguccacc uuucaucuu                                              19

<210> SEQ ID NO 49
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 49
uagcugaaca ucaccacug                                              19

<210> SEQ ID NO 50
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 50
uagcaucaaa gguuagcuu                                              19

<210> SEQ ID NO 51
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 51
uuauagcauc aaagguuag                                              19

<210> SEQ ID NO 52
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 52
uuuauagcau caaagguua                                              19

<210> SEQ ID NO 53
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 53
```
uguuauagca ucaaagguu 19

<210> SEQ ID NO 54
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 54
uuugugcgca uguagaauc 19

<210> SEQ ID NO 55
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 55
uauuugugcg cauguagaa 19

<210> SEQ ID NO 56
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 56
uaccggacuu caucucugu 19

<210> SEQ ID NO 57
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 57
uaaccggacu ucaucucug 19

<210> SEQ ID NO 58
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 58 ugaaaaccg gacuucauc 19

<210> SEQ ID NO 59
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 59
uugaaaaacc ggacuucau 19

<210> SEQ ID NO 60
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 60
uuugaaaaac cggacuuca                                              19

<210> SEQ ID NO 61
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 61
uuuugaaaaa ccggacuuc                                              19

<210> SEQ ID NO 62
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 62
ucuuugaaaa accggacuu                                              19

<210> SEQ ID NO 63
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 63
ucaucauacc uccaguauu                                              19

<210> SEQ ID NO 64
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 64
uucaucauac cuccaguau                                              19

<210> SEQ ID NO 65
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 65
uuucaucaua ccuccagua                                              19

<210> SEQ ID NO 66
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 66
uuauucauca uaccuccag                                              19
```

```
<210> SEQ ID NO 67
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 67
uuauauucau cauaccucc                                               19

<210> SEQ ID NO 68
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 68
uguuuauauu caucauacc                                               19

<210> SEQ ID NO 69
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 69
uauaaccugg auccauaga                                               19

<210> SEQ ID NO 70
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 70
ugauaaccug gauccauag                                               19

<210> SEQ ID NO 71
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 71
ucuaucauuu ugggauaac                                               19

<210> SEQ ID NO 72
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 72
ugcuaucauu uugggauaa                                               19

<210> SEQ ID NO 73
<211> LENGTH: 19
<212> TYPE: RNA
<213> ORGANISM: Artificial Sequence
<220> FEATURE:
<223> OTHER INFORMATION: Synthetic Polynucleotide
```

<400> SEQUENCE: 73
uugcuaucau uuugggaua                                                    19

<210> SEQ ID NO 74
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 74
ucaauuccag gaaagucau                                                    19

<210> SEQ ID NO 75
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 75
uaaccagcua uuagcuuuc                                                    19

<210> SEQ ID NO 76
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 76
ugaaccagcu auuagcuuu                                                    19

<210> SEQ ID NO 77
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 77
uugaaccagc uauuagcuu                                                    19

<210> SEQ ID NO 78
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 78
uuugaaccag cuauuagcu                                                    19

<210> SEQ ID NO 79
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 79
uguugaacca gcuauuagc                                                    19

<210> SEQ ID NO 80

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 80
uaguugaacc agcuauuag                                              19

<210> SEQ ID NO 81
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 81
ucaguugaac cagcuauua                                              19

<210> SEQ ID NO 82
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 82
ugcaguugaa ccagcuauu                                              19

<210> SEQ ID NO 83
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 83
uugcaguuga accagcuau                                              19

<210> SEQ ID NO 84
<211> LENGTH: 2082
<212> TYPE: DNA
<213> ORGANISM: Homo sapiens

<400> SEQUENCE: 84
atcactgtag tagtagctgg aaagagaaat ctgtgactcc aattagccag ttcctgcaga    60
ccttgtgagg actagaggaa gaatgctcct ggctgttttg tactgcctgc tgtggagttt   120
ccagacctcc gctggccatt tcctagagc ctgtgtctcc tctaagaacc tgatggagaa   180
ggaatgctgt ccaccgtgga gcggggacag gagtccctgt ggccagcttt caggcagagg   240
ttcctgtcag aatatccttc tgtccaatgc accacttggg cctcaatttc ccttcacagg   300
ggtggatgac cgggagtcgt ggccttccgt cttttataat aggacctgcc agtgctctgg   360
caacttcatg ggattcaact gtggaaactg caagtttggc ttttgggac caaactgcac   420 agagagacga ctcttggtga agaaacat cttcgatttg agtgcccag agaaggacaa   480 attttttgcc tacctcactt tagcaaagca taccatcagc tcagactatg tcatccccat   540
agggacctat ggccaaatga aaatggatc aacacccatg tttaacgaca tcaatattta   600
tgacctcttt gtctggatgc attattatgt gtcaatggat gcactgcttg ggggatctga   660 aatctgggaga gacattgatt ttgcccatga agcaccagc tttctgcctt ggcatagact   720
cttcttgttg cggtgggaac aagaaatcca gaagctgaca ggagatgaaa acttcactat   780
```

-continued

```
tccatattgg gactggcggg atgcagaaaa gtgtgacatt tgcacagatg agtacatggg      840
aggtcagcac cccacaaatc ctaacttact cagcccagca tcattcttct cctcttggca      900
gattgtctgt agccgattgg aggagtacaa cagccatcag tctttatgca atggaacgcc      960
cgagggacct ttacggcgta atcctggaaa ccatgcaaaa tccagaaccc caaggctccc      1020
ctcttcagct gatgtagaat tttgcctgag tttgacccaa tatgaatctg gttccatgga      1080
taaagctgcc aatttcagct ttagaaatac actggaagga tttgctagtc cacttactgg      1140
gatagcggat gcctctcaaa gcagcatgca caatgccttg cacatctata tgaatggaac      1200
aatgtcccag gtacagggat ctgccaacga tcctatcttc cttcttcacc atgcatttgt      1260
tgacagtatt tttgagcagt ggctccgaag gcaccgtcct cttcaagaag tttatccaga      1320
agccaatgca cccattggac ataaccggga atcctacatg gttccttttta taccactgta      1380 cagaaatggt gatttcttta tttcatccaa agatctgggc tatgactata gctatctaca      1440
agattcagac ccagactctt ttcaagacta cattaagtcc tatttggaac aagcgagtcg      1500
gatctggtca tggctccttg gggcggcgat ggtaggggcc gtcctcactg ccctgctggc      1560
agggcttgtg agcttgctgt gtcgtcacaa gagaaagcag cttcctgaag aaaagcagcc      1620
actcctcatg gagaaagagg attaccacag cttgtatcag agccatttat aaaaggctta      1680
ggcaatagag tagggccaaa aagcctgacc tcactctaac tcaaagtaat gtccaggttc      1740
ccagagaata tctgctggta ttttttctgta aagaccattt gcaaaattgt aacctaatac      1800
aaagtgtagc cttcttccaa ctcaggtaga acacacctgt ctttgtcttg ctgttttcac      1860
tcagcccttt taacattttc ccctaagccc atatgtctaa ggaaaggatg ctatttggta      1920
atgaggaact gttatttgta tgtgaattaa agtgctctta ttttaaaaaa ttgaaataat      1980
tttgattttt gccttctgat tatttaaaga tctatatatg ttttattggc cccttcttta      2040
ttttaataaa acagtgagaa atctaaaaaa aaaaaaaaaa aa                        2082
```

<210> SEQ ID NO 85
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 85
uauaauagga cca      13

<210> SEQ ID NO 86
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 86
auaauaggac cua      13

<210> SEQ ID NO 87
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 87

-continued uaauaggacc uga                                                        13

<210> SEQ ID NO 88
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 88
ucacuuuagc aaa                                                        13

<210> SEQ ID NO 89
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 89
cacuuuagca aaa                                                        13

<210> SEQ ID NO 90
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 90
uggccaaaug aaa                                                        13

<210> SEQ ID NO 91
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 91
agagacauug aua                                                        13

<210> SEQ ID NO 92
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 92
gagacauuga uua                                                        13

<210> SEQ ID NO 93
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 93
cugccuuggc aua                                                        13

<210> SEQ ID NO 94
<211> LENGTH: 13
<212> TYPE: RNA
<213> ORGANISM: Artificial Sequence

```
<220> FEATURE:
<223> OTHER INFORMATION: Synthetic Polynucleotide

<400> SEQUENCE: 94
gacauuugca caa                                                          13

<210> SEQ ID NO 95
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 95
cauuugcaca gaa                                                          13

<210> SEQ ID NO 96
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 96
auuugcacag aua                                                          13

<210> SEQ ID NO 97
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 97
uuugcacaga uga                                                          13

<210> SEQ ID NO 98
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 98
ugcacagaug aga                                                          13

<210> SEQ ID NO 99
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 99
gcacagauga gua                                                          13

<210> SEQ ID NO 100
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 100
cacagaugag uaa                                                          13
```

```
<210> SEQ ID NO 101
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 101
acagaugagu aca                                                          13

<210> SEQ ID NO 102
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 102
uccuaacuua cua                                                          13

<210> SEQ ID NO 103
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 103
ccuaacuuac uca                                                          13

<210> SEQ ID NO 104
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 104
cuaacuuacu caa                                                          13

<210> SEQ ID NO 105
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 105
uucuccucuu gga                                                          13

<210> SEQ ID NO 106
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 106
cuggaaacca uga                                                          13

<210> SEQ ID NO 107
<211> LENGTH: 13
<212> TYPE: RNA
<213> ORGANISM: Artificial Sequence
<220> FEATURE:
<223> OTHER INFORMATION: Synthetic Polynucleotide
```

-continued

<400> SEQUENCE: 107
uggaaaccau gaa                                                          13

<210> SEQ ID NO 108
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 108
ggaaaccaug aca                                                          13

<210> SEQ ID NO 109
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 109
gaaaccauga caa                                                          13

<210> SEQ ID NO 110
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 110
aaaccaugac aaa                                                          13

<210> SEQ ID NO 111
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 111
aaccaugaca aaa                                                          13

<210> SEQ ID NO 112
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 112
ccaauuucag cua                                                          13

<210> SEQ ID NO 113
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 113
uuuagaaaua caa                                                          13

<210> SEQ ID NO 114

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 114
auacacugga aga                                                        13

<210> SEQ ID NO 115
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 115
acacuggaag gaa                                                        13

<210> SEQ ID NO 116
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 116
ggaaggauuu gca                                                        13

<210> SEQ ID NO 117
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 117
aggauuugcu aga                                                        13

<210> SEQ ID NO 118
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 118
gauuugcuag uca                                                        13

<210> SEQ ID NO 119
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 119
gaauggaaca aua                                                        13

<210> SEQ ID NO 120
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 120
```
uggaacaaug uca                                                          13

<210> SEQ ID NO 121
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 121
ccagaagcca aua                                                          13

<210> SEQ ID NO 122
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 122
cagaagccaa uga                                                          13

<210> SEQ ID NO 123
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 123
agaagccaau gca                                                          13

<210> SEQ ID NO 124
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 124
cagagccauu uaa                                                          13

<210> SEQ ID NO 125
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 125
agagccauuu aua                                                          13

<210> SEQ ID NO 126
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 126
ugguccuauu auaaaagac                                                    19

<210> SEQ ID NO 127
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 127
uagguccuau auaaaaga                                                    19

<210> SEQ ID NO 128
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 128
ucagguccua uuauaaaag                                                   19

<210> SEQ ID NO 129
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 129
uuugcuaaag ugagguagg                                                   19

<210> SEQ ID NO 130
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 130
uuuugcuaaa gugagguag                                                   19

<210> SEQ ID NO 131
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 131
uuucauuugg ccauagguc                                                   19

<210> SEQ ID NO 132
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 132
uaucaauguc ucuccagau                                                   19

<210> SEQ ID NO 133
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 133
uaaucaaugu cucuccaga                                                   19
```

```
<210> SEQ ID NO 134
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 134
uaugccaagg cagaaaagc                                                  19

<210> SEQ ID NO 135
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 135
uugugcaaau gucacacuu                                                  19

<210> SEQ ID NO 136
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 136
uucugugcaa augucacac                                                  19

<210> SEQ ID NO 137
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 137
uaucugugca aaugucaca                                                  19

<210> SEQ ID NO 138
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 138
ucaucugugc aaaugucac                                                  19

<210> SEQ ID NO 139
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 139
ucucaucugu gcaaauguc                                                  19

<210> SEQ ID NO 140
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 140
uacucaucug ugcaaaugu                                                    19

<210> SEQ ID NO 141
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 141
uuacucaucu gugcaaaug                                                    19

<210> SEQ ID NO 142
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 142
uguacucauc ugugcaaau                                                    19

<210> SEQ ID NO 143
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 143
uaguaaguua ggauuugug                                                    19

<210> SEQ ID NO 144
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 144
ugaguaaguu aggauuugu                                                    19

<210> SEQ ID NO 145
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 145
uugaguaagu uaggauuug                                                    19

<210> SEQ ID NO 146
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 146
uccaagagga gaagaauga                                                    19

```
<210> SEQ ID NO 147
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 147
ucaugguuuc caggauuac                                                    19

<210> SEQ ID NO 148
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 148
uucaugguuu ccaggauua                                                    19

<210> SEQ ID NO 149
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 149
ugucaugguu uccaggauu                                                    19

<210> SEQ ID NO 150
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 150
uugucauggu uuccaggau                                                    19

<210> SEQ ID NO 151
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 151
uuugucaugg uuuccagga                                                    19

<210> SEQ ID NO 152
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 152
uuuugucaug guuuccagg                                                    19

<210> SEQ ID NO 153
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 153
uagcugaaau uggcagcuu                                           19

<210> SEQ ID NO 154
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 154
uuguauuucu aaagcugaa                                           19

<210> SEQ ID NO 155
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 155
ucuuccagug uauuucuaa                                           19

<210> SEQ ID NO 156
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 156
uuccuuccag uguauuucu                                           19

<210> SEQ ID NO 157
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 157
ugcaaauccu uccagugua                                           19

<210> SEQ ID NO 158
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 158
ucuagcaaau ccuuccagu                                           19

<210> SEQ ID NO 159
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 159
ugacuagcaa auccuucca                                           19

<210> SEQ ID NO 160
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 160
uauuguucca uucauauag                                                       19

<210> SEQ ID NO 161
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 161
ugacauuguu ccauucaua                                                       19

<210> SEQ ID NO 162
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 162
uauuggcuuc uggauaaac                                                       19

<210> SEQ ID NO 163
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 163
ucauuggcuu cuggauaaa                                                       19

<210> SEQ ID NO 164
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 164
ugcauuggcu ucuggauaa                                                       19

<210> SEQ ID NO 165
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 165
uuaaauggcu cugauacaa                                                       19

<210> SEQ ID NO 166
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 166
```
uauaaauggc ucugauaca                                              19

<210> SEQ ID NO 167
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 167
ugauguucag cua                                                    13

<210> SEQ ID NO 168
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 168
ugauguucag cua                                                    13

<210> SEQ ID NO 169
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 169
ugauguucag cua                                                    13

<210> SEQ ID NO 170
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 170
ugauguucag cua                                                    13

<210> SEQ ID NO 171
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (6)..(7)
<223> OTHER INFORMATION: n is 5 methyl U
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature

```
<222> LOCATION: (12)..(12)
<223> OTHER INFORMATION: n is 5 methyl U

<400> SEQUENCE: 171
ngangnnnag nna                                                    13

<210> SEQ ID NO 172
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 172
ugauguucag cua                                                    13

<210> SEQ ID NO 173
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 173
accuuugaug cua                                                    13

<210> SEQ ID NO 174
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 174
accuuugaug cua                                                    13

<210> SEQ ID NO 175
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 175
accuuugaug cua                                                    13

<210> SEQ ID NO 176
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 176
accuuugaug cua                                                    13

<210> SEQ ID NO 177
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 177
accuuugaug cua                                                    13
```

```
<210> SEQ ID NO 178
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 178
accuuugaug cua                                                              13

<210> SEQ ID NO 179
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(3)
<223> OTHER INFORMATION: n is 5 methyl C
<220> FEATURE:
<221> NAME/KEY: misc_feature
<222> LOCATION: (4)..(6)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl U

<400> SEQUENCE: 179
annnnngang nna                                                              13

<210> SEQ ID NO 180
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 180
agguaugaug aaa                                                              13

<210> SEQ ID NO 181
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 181
agguaugaug aaa                                                              13

<210> SEQ ID NO 182
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 182
agguaugaug aaa                                                              13
```

<210> SEQ ID NO 183
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 183
agguaugaug aaa                                                          13

<210> SEQ ID NO 184
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl U

<400> SEQUENCE: 184
aggnangang aaa                                                          13

<210> SEQ ID NO 185
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl U

<400> SEQUENCE: 185
aggnangang aaa                                                          13

<210> SEQ ID NO 186
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 186
uagcugguuc aaa                                                          13

<210> SEQ ID NO 187
<211> LENGTH: 13
<212> TYPE: RNA
<213> ORGANISM: Artificial Sequence
<220> FEATURE:

```
<223> OTHER INFORMATION: Synthetic Polynucleotide

<400> SEQUENCE: 187
uagcugguuc aaa                                                          13

<210> SEQ ID NO 188
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 188
uagcugguuc aaa                                                          13

<210> SEQ ID NO 189
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 189
uagcugguuc aaa                                                          13

<210> SEQ ID NO 190
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (5)..(5)
<223> OTHER INFORMATION: n is 5 methyl U
<220> FEATURE:
<221> NAME/KEY: misc_feature
<222> LOCATION: (8)..(9)
<223> OTHER INFORMATION: n is 5 methyl U
<220> FEATURE:
<221> NAME/KEY: misc_feature
<222> LOCATION: (10)..(10)
<223> OTHER INFORMATION: n is 5 methyl C

<400> SEQUENCE: 190
nagnnggnnn aaa                                                          13

<210> SEQ ID NO 191
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 191
agcugguuca aca                                                          13

<210> SEQ ID NO 192
<211> LENGTH: 13
<212> TYPE: RNA
<213> ORGANISM: Artificial Sequence
```

```
<220> FEATURE:
<223> OTHER INFORMATION: Synthetic Polynucleotide

<400> SEQUENCE: 192
agcugguuca aca                                                            13

<210> SEQ ID NO 193
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 193
agcugguuca aca                                                            13

<210> SEQ ID NO 194
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 194
agcugguuca aca                                                            13

<210> SEQ ID NO 195
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3)..(3)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (7)..(8)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl C

<400> SEQUENCE: 195 agnggnnna ana                                                             13

<210> SEQ ID NO 196
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 196
uagcugaaca ucaccacug                                                      19

<210> SEQ ID NO 197
<211> LENGTH: 19
<212> TYPE: RNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (5)..(5)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl U
<220> FEATURE:
<221> NAME/KEY: misc_feature
<222> LOCATION: (12)..(12)
<223> OTHER INFORMATION: n is 5 methyl C
<220> FEATURE:
<221> NAME/KEY: misc_feature
<222> LOCATION: (14)..(15)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl U

<400> SEQUENCE: 197
nagnngaana nnannanng                                                  19

<210> SEQ ID NO 198
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (5)..(5)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl U
<220> FEATURE:
<221> NAME/KEY: misc_feature
<222> LOCATION: (12)..(12)
<223> OTHER INFORMATION: n is 5 methyl C
<220> FEATURE:
<221> NAME/KEY: misc_feature
<222> LOCATION: (14)..(15)
<223> OTHER INFORMATION: n is 5 methyl C
```

<220> FEATURE:
<221> NAME/KEY: misc_feature
<222> LOCATION: (17)..(17)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl U

<400> SEQUENCE: 198
nagnngaana nnannanng                                              19

<210> SEQ ID NO 199
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 199
uagcugaaca ucaccacug                                              19

<210> SEQ ID NO 200
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 200
uagcugaaca ucaccacug                                              19

<210> SEQ ID NO 201
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 201
uagcugaaca ucaccacug                                              19

<210> SEQ ID NO 202
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 202
uagcaucaaa gguuagcuu                                              19

<210> SEQ ID NO 203
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 203
uagcaucaaa gguuagcuu                                              19

<210> SEQ ID NO 204
<211> LENGTH: 19
<212> TYPE: RNA
<213> ORGANISM: Artificial Sequence
<220> FEATURE:

```
<223> OTHER INFORMATION: Synthetic Polynucleotide

<400> SEQUENCE: 204
uagcaucaaa gguuagcuu                                                  19

<210> SEQ ID NO 205
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (13)..(14)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl U

<400> SEQUENCE: 205
nagnannaaa ggnnagnnu                                                  19

<210> SEQ ID NO 206
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl C
<220> FEATURE:
<221> NAME/KEY: misc_feature
```

```
<222> LOCATION: (18)..(18)
<223> OTHER INFORMATION: n is 5 methyl U

<400> SEQUENCE: 206
nagnannaaa ggnuagnnu                                            19

<210> SEQ ID NO 207
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (13)..(14)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl U

<400> SEQUENCE: 207
uagnannaaa ggnnagnnu                                            19

<210> SEQ ID NO 208
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 208
uagcaucaaa gguuagcuu                                            19

<210> SEQ ID NO 209
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 209
uuucaucaua ccuccagua                                            19

<210> SEQ ID NO 210
<211> LENGTH: 19
<212> TYPE: RNA
<213> ORGANISM: Artificial Sequence
<220> FEATURE:
<223> OTHER INFORMATION: Synthetic Polynucleotide
```

<400> SEQUENCE: 210
uuucaucaua ccuccagua                                                19

<210> SEQ ID NO 211
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (9)..(9)
<223> OTHER INFORMATION: n is 5 methyl U
<220> FEATURE:
<221> NAME/KEY: misc_feature
<222> LOCATION: (11)..(12)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (14)..(15)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl U

<400> SEQUENCE: 211
nnnnannana nnnnnagna                                                19

<210> SEQ ID NO 212
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (9)..(9)
<223> OTHER INFORMATION: n is 5 methyl U

```
<220> FEATURE:
<221> NAME/KEY: misc_feature
<222> LOCATION: (11)..(12)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (14)..(15)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl U

<400> SEQUENCE: 212
nnnnannana nnnnnagna                                                  19

<210> SEQ ID NO 213
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 213
uuucaucaua ccuccagua                                                  19

<210> SEQ ID NO 214
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 214
uuucaucaua ccuccagua                                                  19

<210> SEQ ID NO 215
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 215
uuugaaccag cuauuagcu                                                  19

<210> SEQ ID NO 216
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 216
uuugaaccag cuauuagcu                                                  19

<210> SEQ ID NO 217
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
```

```
<223> OTHER INFORMATION: n is 5 methyl U
<220> FEATURE:
<221> NAME/KEY: misc_feature
<222> LOCATION: (7)..(8)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl U
<220> FEATURE:
<221> NAME/KEY: misc_feature
<222> LOCATION: (14)..(15)
<223> OTHER INFORMATION: n is 5 methyl U
<220> FEATURE:
<221> NAME/KEY: misc_feature
<222> LOCATION: (18)..(18)
<223> OTHER INFORMATION: n is 5 methyl C

<400> SEQUENCE: 217
nnngaannag nnannagnu                                                19

<210> SEQ ID NO 218
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is 5 methyl U
<220> FEATURE:
<221> NAME/KEY: misc_feature
<222> LOCATION: (7)..(8)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl U
<220> FEATURE:
<221> NAME/KEY: misc_feature
<222> LOCATION: (14)..(15)
<223> OTHER INFORMATION: n is 5 methyl U
<220> FEATURE:
<221> NAME/KEY: misc_feature
<222> LOCATION: (18)..(18)
<223> OTHER INFORMATION: n is 5 methyl C

<400> SEQUENCE: 218
nnngaannag nnannagnu                                                19

<210> SEQ ID NO 219
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 219
uuugaaccag cuauuagcu                                                19

<210> SEQ ID NO 220
<211> LENGTH: 19
<212> TYPE: RNA
<213> ORGANISM: Artificial Sequence
```

```
<220> FEATURE:
<223> OTHER INFORMATION: Synthetic Polynucleotide

<400> SEQUENCE: 220
uguugaacca gcuauuagc                                                19

<210> SEQ ID NO 221
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 221
uguugaacca gcuauuagc                                                19

<210> SEQ ID NO 222
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (3)..(4)
<223> OTHER INFORMATION: n is 5 methyl U
<220> FEATURE:
<221> NAME/KEY: misc_feature
<222> LOCATION: (8)..(9)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (15)..(16)
<223> OTHER INFORMATION: n is 5 methyl U

<400> SEQUENCE: 222
ngnngaanna gnnannagc                                                19

<210> SEQ ID NO 223
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (3)..(4)
<223> OTHER INFORMATION: n is 5 methyl U
<220> FEATURE:
<221> NAME/KEY: misc_feature
<222> LOCATION: (8)..(9)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl C
<220> FEATURE:
```

```
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (15)..(16)
<223> OTHER INFORMATION: n is 5 methyl U

<400> SEQUENCE: 223
ngnngaanna gnnannagc                                                   19

<210> SEQ ID NO 224
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 224
uguugaacca gcuauuagc                                                   19

<210> SEQ ID NO 225
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 225
cacuuuagca aaa                                                         13

<210> SEQ ID NO 226
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 226
cacuuuagca aaa                                                         13

<210> SEQ ID NO 227
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 227
cacuuuagca aaa                                                         13

<210> SEQ ID NO 228
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 228
cacuuuagca aaa                                                         13

<210> SEQ ID NO 229
<211> LENGTH: 13
<212> TYPE: RNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (3)..(3)
<223> OTHER INFORMATION: n is 5 methyl C
<220> FEATURE:
<221> NAME/KEY: misc_feature
<222> LOCATION: (4)..(6)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C

<400> SEQUENCE: 229
nannnnagna aaa                                                          13

<210> SEQ ID NO 230
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (3)..(3)
<223> OTHER INFORMATION: n is 5 methyl C
<220> FEATURE:
<221> NAME/KEY: misc_feature
<222> LOCATION: (4)..(6)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C

<400> SEQUENCE: 230
nannnnagna aaa                                                          13

<210> SEQ ID NO 231
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 231
gagacauuga uua                                                          13

<210> SEQ ID NO 232
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 232
gagacauuga uua                                                          13

<210> SEQ ID NO 233
<211> LENGTH: 13
<212> TYPE: RNA
<213> ORGANISM: Artificial Sequence
<220> FEATURE:
```

-continued

<223> OTHER INFORMATION: Synthetic Polynucleotide

<400> SEQUENCE: 233
gagacauuga uua                                                        13

<210> SEQ ID NO 234
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 234
gagacauuga uua                                                        13

<210> SEQ ID NO 235
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (7)..(8)
<223> OTHER INFORMATION: n is 5 methyl U
<220> FEATURE:
<221> NAME/KEY: misc_feature
<222> LOCATION: (11)..(12)
<223> OTHER INFORMATION: n is 5 methyl U

<400> SEQUENCE: 235
gaganannga nna                                                        13

<210> SEQ ID NO 236
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 236
uuugcacaga uga                                                        13

<210> SEQ ID NO 237
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 237
uuugcacaga uga                                                        13

<210> SEQ ID NO 238
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 238
uuugcacaga uga                                                        13

```
<210> SEQ ID NO 239
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 239
uuugcacaga uga                                                          13

<210> SEQ ID NO 240
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl U

<400> SEQUENCE: 240
nnngnanaga nga                                                          13

<210> SEQ ID NO 241
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (11)..(11)
<223> OTHER INFORMATION: n is 5 methyl U

<400> SEQUENCE: 241
nnngnanaga nga                                                          13

<210> SEQ ID NO 242
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 242
gcacagauga gua                                                          13
```

<210> SEQ ID NO 243
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 243
gcacagauga gua                                                          13

<210> SEQ ID NO 244
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 244
gcacagauga gua                                                          13

<210> SEQ ID NO 245
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 245
gcacagauga gua                                                          13

<210> SEQ ID NO 246
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 246
gcacagauga gua                                                          13

<210> SEQ ID NO 247
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl U
<220> FEATURE:
<221> NAME/KEY: misc_feature
<222> LOCATION: (12)..(12)
<223> OTHER INFORMATION: n is 5 methyl U

<400> SEQUENCE: 247
gnanaganga gna                                                          13

<210> SEQ ID NO 248
<211> LENGTH: 13

-continued

```
<212> TYPE: RNA
<213> ORGANISM: Artificial Sequence
<220> FEATURE:
<223> OTHER INFORMATION: Synthetic Polynucleotide

<400> SEQUENCE: 248
uucuccucuu gga                                                              13

<210> SEQ ID NO 249
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 249
uucuccucuu gga                                                              13

<210> SEQ ID NO 250
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 250
uucuccucuu gga                                                              13

<210> SEQ ID NO 251
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 251
uucuccucuu gga                                                              13

<210> SEQ ID NO 252
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is 5 methyl U
<220> FEATURE:
<221> NAME/KEY: misc_feature
<222> LOCATION: (3)..(3)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(6)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (9)..(10)
```

```
<223> OTHER INFORMATION: n is 5 methyl U

<400> SEQUENCE: 252
nnnnnnnnnn gga                                                          13

<210> SEQ ID NO 253
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 253
aggauuugcu aga                                                          13

<210> SEQ ID NO 254
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 254
aggauuugcu aga                                                          13

<210> SEQ ID NO 255
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 255
aggauuugcu aga                                                          13

<210> SEQ ID NO 256
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 256
aggauuugcu aga                                                          13

<210> SEQ ID NO 257
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(7)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl U

<400> SEQUENCE: 257
aggannngnn aga                                                          13
```

```
<210> SEQ ID NO 258
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 258
gaauggaaca aua                                                          13

<210> SEQ ID NO 259
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 259
gaauggaaca aua                                                          13

<210> SEQ ID NO 260
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 260
gaauggaaca aua                                                          13

<210> SEQ ID NO 261
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 261
gaauggaaca aua                                                          13

<210> SEQ ID NO 262
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl U

<400> SEQUENCE: 262
gaanggaana ana                                                          13

<210> SEQ ID NO 263
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (9)..(9)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl U

<400> SEQUENCE: 263
gaanggaana ana                                                          13

<210> SEQ ID NO 264
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 264
uuuugcuaaa gugagguag                                                    19

<210> SEQ ID NO 265
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 265
uuuugcuaaa gugagguag                                                    19

<210> SEQ ID NO 266
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: n is 5 methyl U
<220> FEATURE:
<221> NAME/KEY: misc_feature
<222> LOCATION: (6)..(6)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (12)..(12)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl U

<400> SEQUENCE: 266
nnnngnnaaa gngaggnag                                                    19

<210> SEQ ID NO 267
<211> LENGTH: 19
<212> TYPE: RNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(4)
<223> OTHER INFORMATION: n is 5 methyl U
<220> FEATURE:
<221> NAME/KEY: misc_feature
<222> LOCATION: (6)..(6)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (12)..(12)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl U

<400> SEQUENCE: 267
nnnngnnaaa gngaggnag                                                  19

<210> SEQ ID NO 268
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 268
uuuugcuaaa gugagguag                                                  19

<210> SEQ ID NO 269
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 269
uuuugcuaaa gugagguag                                                  19

<210> SEQ ID NO 270
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 270
uaaucaaugu cucuccaga                                                  19

<210> SEQ ID NO 271
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 271
uaaucaaugu cucuccaga                                                  19

<210> SEQ ID NO 272
<211> LENGTH: 19
<212> TYPE: RNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl U
<220> FEATURE:
<221> NAME/KEY: misc_feature
<222> LOCATION: (10)..(10)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl U
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (14)..(14)
<223> OTHER INFORMATION: n is 5 methyl U
<220> FEATURE:
<221> NAME/KEY: misc_feature
<222> LOCATION: (15)..(16)
<223> OTHER INFORMATION: n is 5 methyl C

<400> SEQUENCE: 272
naannaangn nnnnnnaga                                                  19

<210> SEQ ID NO 273
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl U
<220> FEATURE:
<221> NAME/KEY: misc_feature
<222> LOCATION: (10)..(10)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
```

```
<222> LOCATION: (12)..(12)
<223> OTHER INFORMATION: n is 5 methyl U
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (14)..(14)
<223> OTHER INFORMATION: n is 5 methyl U
<220> FEATURE:
<221> NAME/KEY: misc_feature
<222> LOCATION: (15)..(16)
<223> OTHER INFORMATION: n is 5 methyl C

<400> SEQUENCE: 273
naannaangn nnnnnnaga                                             19

<210> SEQ ID NO 274
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 274
uaaucaaugu cucuccaga                                             19

<210> SEQ ID NO 275
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 275
ucaucugugc aaaugucac                                             19

<210> SEQ ID NO 276
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 276
ucaucugugc aaaugucac                                             19

<210> SEQ ID NO 277
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
```

```
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (8)..(8)
<223> OTHER INFORMATION: n is 5 methyl U
<220> FEATURE:
<221> NAME/KEY: misc_feature
<222> LOCATION: (10)..(10)
<223> OTHER INFORMATION: n is 5 methyl C
<220> FEATURE:
<221> NAME/KEY: misc_feature
<222> LOCATION: (14)..(14)
<223> OTHER INFORMATION: n is 5 methyl U
<220> FEATURE:
<221> NAME/KEY: misc_feature
<222> LOCATION: (16)..(16)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl C

<400> SEQUENCE: 277
nnannngngn aaangnnac                                          19

<210> SEQ ID NO 278
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (6)..(6)
<223> OTHER INFORMATION: n is 5 methyl U
<220> FEATURE:
<221> NAME/KEY: misc_feature
<222> LOCATION: (8)..(8)
<223> OTHER INFORMATION: n is 5 methyl U
<220> FEATURE:
<221> NAME/KEY: misc_feature
<222> LOCATION: (10)..(10)
<223> OTHER INFORMATION: n is 5 methyl C
<220> FEATURE:
<221> NAME/KEY: misc_feature
<222> LOCATION: (14)..(14)
<223> OTHER INFORMATION: n is 5 methyl U
<220> FEATURE:
<221> NAME/KEY: misc_feature
<222> LOCATION: (16)..(16)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl C

<400> SEQUENCE: 278
nnannngngn aaangnnac                                          19
```

```
<210> SEQ ID NO 279
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 279
ucaucugugc aaaugucac                                               19

<210> SEQ ID NO 280
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 280
ucaucugugc aaaugucac                                               19

<210> SEQ ID NO 281
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 281
uacucaucug ugcaaaugu                                               19

<210> SEQ ID NO 282
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 282
uacucaucug ugcaaaugu                                               19

<210> SEQ ID NO 283
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (3)..(3)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (8)..(8)
```

```
<223> OTHER INFORMATION: n is 5 methyl C
<220> FEATURE:
<221> NAME/KEY: misc_feature
<222> LOCATION: (9)..(9)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl U
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl U

<400> SEQUENCE: 283
nannnannng ngnaaangu                                               19

<210> SEQ ID NO 284
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (3)..(3)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl U
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (9)..(9)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl U
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl U

<400> SEQUENCE: 284
nannnannng ngnaaangu                                               19

<210> SEQ ID NO 285
<211> LENGTH: 19
<212> TYPE: RNA
<213> ORGANISM: Artificial Sequence
```

```
<220> FEATURE:
<223> OTHER INFORMATION: Synthetic Polynucleotide

<400> SEQUENCE: 285
uacucaucug ugcaaaugu                                              19

<210> SEQ ID NO 286
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 286
uacucaucug ugcaaaugu                                              19

<210> SEQ ID NO 287
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 287
uccaagagga gaagaauga                                              19

<210> SEQ ID NO 288
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 288
uccaagagga gaagaauga                                              19

<210> SEQ ID NO 289
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (2)..(3)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl U

<400> SEQUENCE: 289
nnnaagagga gaagaanga                                              19

<210> SEQ ID NO 290
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
```

```
<221> NAME/KEY: misc_feature
<222> LOCATION: (2)..(3)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl U

<400> SEQUENCE: 290
nnnaagagga gaagaanga                                                19

<210> SEQ ID NO 291
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 291
uccaagagga gaagaauga                                                19

<210> SEQ ID NO 292
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 292
ucuagcaaau ccuuccagu                                                19

<210> SEQ ID NO 293
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 293
ucuagcaaau ccuuccagu                                                19

<210> SEQ ID NO 294
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (3)..(3)
<223> OTHER INFORMATION: n is 5 methyl U
<220> FEATURE:
<221> NAME/KEY: misc_feature
<222> LOCATION: (6)..(6)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl U
<220> FEATURE:
<221> NAME/KEY: misc_feature
<222> LOCATION: (11)..(12)
<223> OTHER INFORMATION: n is 5 methyl C
```

```
<220> FEATURE:
<221> NAME/KEY: misc_feature
<222> LOCATION: (13)..(14)
<223> OTHER INFORMATION: n is 5 methyl U
<220> FEATURE:
<221> NAME/KEY: misc_feature
<222> LOCATION: (15)..(16)
<223> OTHER INFORMATION: n is 5 methyl C

<400> SEQUENCE: 294
nnnagnaaan nnnnnnagu                                              19

<210> SEQ ID NO 295
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (3)..(3)
<223> OTHER INFORMATION: n is 5 methyl U
<220> FEATURE:
<221> NAME/KEY: misc_feature
<222> LOCATION: (6)..(6)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl U
<220> FEATURE:
<221> NAME/KEY: misc_feature
<222> LOCATION: (11)..(12)
<223> OTHER INFORMATION: n is 5 methyl C
<220> FEATURE:
<221> NAME/KEY: misc_feature
<222> LOCATION: (13)..(14)
<223> OTHER INFORMATION: n is 5 methyl U
<220> FEATURE:
<221> NAME/KEY: misc_feature
<222> LOCATION: (15)..(16)
<223> OTHER INFORMATION: n is 5 methyl C

<400> SEQUENCE: 295
nnnagnaaan nnnnnnagu                                              19

<210> SEQ ID NO 296
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 296
ucuagcaaau ccuuccagu                                              19

<210> SEQ ID NO 297
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 297
```

-continued uauuguucca uucauauag                                          19

<210> SEQ ID NO 298
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 298
uauuguucca uucauauag                                          19

<210> SEQ ID NO 299
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (3)..(4)
<223> OTHER INFORMATION: n is 5 methyl U
<220> FEATURE:
<221> NAME/KEY: misc_feature
<222> LOCATION: (6)..(7)
<223> OTHER INFORMATION: n is 5 methyl U
<220> FEATURE:
<221> NAME/KEY: misc_feature
<222> LOCATION: (8)..(9)
<223> OTHER INFORMATION: n is 5 methyl C
<220> FEATURE:
<221> NAME/KEY: misc_feature
<222> LOCATION: (11)..(12)
<223> OTHER INFORMATION: n is 5 methyl U
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (15)..(15)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl U

<400> SEQUENCE: 299
nanngnnnna nnnananag                                          19

<210> SEQ ID NO 300
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is 5 methyl U
<220> FEATURE:
<221> NAME/KEY: misc_feature
<222> LOCATION: (3)..(4)
<223> OTHER INFORMATION: n is 5 methyl U
<220> FEATURE:
<221> NAME/KEY: misc_feature
<222> LOCATION: (6)..(7)
<223> OTHER INFORMATION: n is 5 methyl U
<220> FEATURE:
<221> NAME/KEY: misc_feature

```
<222> LOCATION: (8)..(9)
<223> OTHER INFORMATION: n is 5 methyl C
<220> FEATURE:
<221> NAME/KEY: misc_feature
<222> LOCATION: (11)..(12)
<223> OTHER INFORMATION: n is 5 methyl U
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (15)..(15)
<223> OTHER INFORMATION: n is 5 methyl U
<220> FEATURE:
<221> NAME/KEY: misc_feature
<222> LOCATION: (17)..(17)
<223> OTHER INFORMATION: n is 5 methyl U

<400> SEQUENCE: 300
nanngnnnna nnnananag                                              19

<210> SEQ ID NO 301
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 301
uauuguucca uucauauag                                              19

<210> SEQ ID NO 302
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 302
uauuguucca uucauauag                                              19
```

METHODS FOR TREATING AGING AND SKIN DISORDERS USING NUCLEIC ACIDS TARGETING TYR OR MMP1

RELATED APPLICATIONS

This application is a national stage filing under 35 U.S.C. § 371 of International Application No. PCT/US2015/048565, entitled "METHODS FOR TREATING AGING AND SKIN DISORDERS USING NUCLEIC ACIDS TARGETING TYR OR MMP1," filed on Sep. 4, 2015, which was published under PCT Article 21(2) in English and which claims the benefit under 35 U.S.C. § 119(e) of U.S. Provisional Application Serial No. U.S. 62/046,523, entitled "METHODS FOR TREATING AGING AND SKIN DISORDERS USING NUCLEIC ACIDS TARGETING TYR OR MMP1," filed on Sep. 5, 2014, U.S. Provisional Application Serial No. U.S. 62/047,972, entitled "METHODS FOR TREATING AGING AND SKIN DISORDERS USING NUCLEIC ACIDS TARGETING TYR OR MMP1," filed on Sep. 9, 2014, and U.S. Provisional Application Serial No. U.S. 62/102,287, entitled "METHODS FOR TREATING AGING AND SKIN DISORDERS USING NUCLEIC ACIDS TARGETING TYR OR MMP1," filed on Jan. 12, 2015, the entire disclosures of each of which are herein incorporated by reference in their entireties.

FIELD OF THE INVENTION

The invention pertains to nucleic acid molecules with improved in vivo delivery properties and their use to reduce the expression of MMP1 or TYR.

BACKGROUND OF THE INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions in vivo.

A major problem has been the delivery of these compounds to cells and tissues. Conventional double-stranded RNAi compounds, 19-29 bases long, form a highly negatively-charged rigid helix of approximately 1.5 by 10-15 nm in size. This rod type molecule cannot get through the cell-membrane and as a result has very limited efficacy both in vitro and in vivo. As a result, all conventional RNAi compounds require some kind of delivery vehicle to promote their tissue distribution and cellular uptake. This is considered to be a major limitation of the RNAi technology.

There have been previous attempts to apply chemical modifications to oligonucleotides to improve their cellular uptake properties. One such modification was the attachment of a cholesterol molecule to the oligonucleotide. A first report on this approach was by Letsinger et al., in 1989. Subsequently, ISIS Pharmaceuticals, Inc. (Carlsbad, Calif.) reported on more advanced techniques in attaching the cholesterol molecule to the oligonucleotide (Manoharan, 1992).

With the discovery of siRNAs in the late nineties, similar types of modifications were attempted on these molecules to enhance their delivery profiles. Cholesterol molecules conjugated to slightly modified (Soutschek, 2004) and heavily modified (Wolfrum, 2007) siRNAs appeared in the literature. Yamada et al., 2008 also reported on the use of advanced linker chemistries which further improved cholesterol mediated uptake of siRNAs. In spite of all this effort, the uptake of these types of compounds impaired to be inhibited in the presence of biological fluids resulting in highly limited efficacy in gene silencing in vivo, limiting the applicability of these compounds in a clinical setting.

SUMMARY

Aspects of the invention relate to methods for treating a skin disorder comprising administering to a subject in need thereof a therapeutically effective amount of a nucleic acid molecule that is directed against a gene encoding Matrix metalloproteinase-1 (MMP1), tyrosinase (TYR) or prostaglandin-endoperoxide synthase 2 (PTGS2).

In some embodiments, the nucleic acid molecule is a chemically modified oligonucleotide. In some embodiments, the nucleic acid molecule is a double stranded nucleic acid molecule. In some embodiments, the nucleic acid molecule is an isolated double stranded nucleic acid molecule that includes a double stranded region and a single stranded region, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the isolated double stranded nucleic acid molecule are modified.

In some embodiments, the isolated double stranded nucleic acid molecule further comprises a hydrophobic conjugate that is attached to the isolated double stranded nucleic acid molecule.

In some embodiments, the skin disorder is skin photo aging or acne scarring. In some embodiments, the nucleic acid molecule is directed against a gene encoding MMP1. In some embodiments, the skin disorder is cutaneous hyperpigmentation, melasma or skin lentigos.

In some embodiments, the nucleic acid molecule is directed against a gene encoding TYR. In some embodiments, the nucleic acid molecule silences gene expression through an RNAi mechanism of action.

In some embodiments, the nucleic acid molecule is in a composition formulated for topical delivery. In some embodiments, the nucleic acid molecule is in a composition formulated for delivery to the skin. In some embodiments, the nucleic acid molecule is in a composition formulated for intradermal injection. In some embodiments, the nucleic acid molecule is in a composition formulated for extended release of the molecule following intradermal injection.

In some embodiments, two or more nucleic acid molecules directed against genes encoding different proteins are administered to the subject. In some embodiments, two or more nucleic acid molecules directed against genes encoding the same protein are administered to the subject.

In some embodiments, the nucleic acid molecule is composed of nucleotides and at least 30% of the nucleotides are chemically modified. In some embodiments, the nucleic acid molecule contains at least one modified backbone linkage. In some embodiments, the nucleic acid molecule contains at least one phosphorothioate linkage. In some embodiments, the nucleic acid molecule is composed of nucleotides and at least one of the nucleotides contains a 2' chemical modifications selection from 2'OMe or 2'Fluoro.

In some embodiments, the nucleic acid molecule is administered once. In some embodiments, the nucleic acid molecule is administered more than once.

In some embodiments, the nucleic acid molecule comprises at least 12 contiguous nucleotides of a sequence with Table 1 or Table 2. In some embodiments, the nucleic acid molecule comprises a sequence selected from: MMP1-2, MMP1-7, MMP1-8, MMP1-23, MMP1-35 and MMP1-36, as indicated in Tables 1 and 2.

In some embodiments, the nucleic acid molecule is directed against at least 12 contiguous nucleotides of a sequence with Table 3 or Table 4. In some embodiments, the nucleic acid molecule comprises a sequence selected from: TYR-5, TYR-8, TYR-13, TYR-14, TYR-15, TYR-20, TYR-32, TYR-33 and TYR-34, as indicated in Tables 3 and 4.

In some embodiments, the skin disorder is selected from the group consisting of: chronic ulcers (venous ulcers), gangrene (*Vibrio* and *Clostridium*), and blistering skin disorders (e.g. Stevens-Johnson, etc.). In some embodiments, the skin disorder is keloids.

Aspects of the invention relate to a chemically modified double stranded nucleic acid molecule that is directed against a sequence selected from the sequences within Tables 1-4. In some embodiments, the chemically modified double stranded nucleic acid molecule is an sd-rxRNA.

Aspects of the invention relate to a chemically modified double stranded nucleic acid molecule that is directed against a sequence comprising at least 12 contiguous nucleotides of a sequence selected from the sequences within Tables 1-4. In some embodiments, the chemically modified double stranded nucleic acid molecule is an sd-rxRNA.

Aspects of the invention relate to a chemically modified double stranded nucleic acid molecule that comprises at least 12 contiguous nucleotides of a sequence selected from the sequences within Tables 1-4. In some embodiments, the chemically modified double stranded nucleic acid molecule is an sd-rxRNA.

In some embodiments, the sd-rxRNA is hydrophobically modified. In some embodiments, the sd-rxRNA is linked to one or more hydrophobic conjugates.

Aspects of the invention relate to compositions comprising any of the chemically modified double stranded nucleic acid molecules described herein.

In some embodiments, a chemically modified double stranded nucleic acid molecule comprises a sequence selected from: MMP1-2, MMP1-7, MMP1-8, MMP1-23, MMP1-35, MMP1-36, TYR-5, TYR-8, TYR-13, TYR-14, TYR-15, TYR-20, TYR-32, TYR-33 and TYR-34.

Aspects of the invention relate to methods for treating tuberculosis, arthritis (osteo and rheumatoid), corneal erosions, periodontitis, endometrial cancer, or endometriosis comprising administering to a subject in need thereof a therapeutically effective amount of a nucleic acid molecule that is directed against a gene encoding Matrix metalloproteinase-1 (MMP1).

In some embodiments, a nucleic acid molecule comprises at least 12 contiguous nucleotides of a sequence selected from the sequences within Table 5 or Table 6. In some embodiments, a nucleic acid molecule comprises a sequence selected from the sequences within Table 5 or Table 6. In some embodiments, a nucleic acid molecule comprises a sense strand sequence selected from the sequences within Table 5 and an antisense strand sequence selected from the sequences within Table 6.

In some embodiments, a nucleic acid molecule comprises at least 12 contiguous nucleotides of a sequence selected from the sequences within Table 7 or Table 8. In some embodiments, a nucleic acid molecule comprises a sequence selected from the sequences within Table 7 or Table 8. In some embodiments, a nucleic acid molecule comprises a sense strand sequence selected from the sequences within Table 7 and an antisense strand sequence selected from the sequences within Table 8.

Aspects of the invention relate to chemically modified double stranded nucleic acid molecules selected from the sequences within Tables 5-8. In some embodiments, the chemically modified double stranded nucleic acid molecule is an sd-rxRNA.

Aspects of the invention relate to chemically modified double stranded nucleic acid molecules that comprises at least 12 contiguous nucleotides of a sequence selected from the sequences within Tables 5-8. In some embodiments, the chemically modified double stranded nucleic acid molecule is an sd-rxRNA. In some embodiments, the sd-rxRNA is hydrophobically modified. In some embodiments, the sd-rxRNA is linked to one or more hydrophobic conjugates.

In some embodiments, the chemically modified double stranded nucleic acid molecule is directed against MMP-1 and:
  i) the sense strand sequence is selected from the group consisting of: SEQ ID NOs 167, 171 and 172, including the modifications indicated in Table 5, and the antisense strand sequence is selected from the group consisting of: SEQ ID NOs 196, 197, 198, 199 and 200, including the modifications indicated in Table 6;
  ii) the sense strand sequence is selected from the group consisting of SEQ ID NOs 173 and 179, including the modifications indicated in Table 5, and the antisense strand sequence is selected from the group consisting of SEQ ID NOs 202, 203, 204, 205, 206, 207 and 208, including the modifications indicated in Table 6;
  iii) the sense strand sequence is selected from the group consisting of SEQ ID NOs 180, 184 and 185, including the modifications indicated in Table 5, and the antisense strand sequence is selected from the group consisting of SEQ ID NOs 209, 210, 211, 212 and 213, including the modifications indicated in Table 6;
  iv) the sense strand sequence is selected from the group consisting of SEQ ID NOs 186 and 190, including the modifications indicated in Table 5, and the antisense strand sequence is selected from the group consisting of SEQ ID NOs 215, 216, 217, 218 and 219, including the modifications indicated in Table 6; or
  v) the sense strand sequence is selected from the group consisting of SEQ ID NOs 191 and 195, including the modifications indicated in Table 5, and the antisense strand sequence is selected from the group consisting of SEQ ID NOs 220, 221, 222, 223 and 224, including the modifications indicated in Table 6.

In some embodiments, the chemically modified double stranded nucleic acid molecule is directed against TYR and:
  i) the sense strand sequence is selected from the group consisting of SEQ ID NOs 225, 229 and 230, including the modifications indicated in Table 7, and the antisense strand sequence is selected from the group consisting of SEQ ID NOs 264, 265, 266, 267 and 268, including the modifications indicated in Table 8;
  ii) the sense strand sequence is selected from the group consisting of SEQ ID NOs 231 and 235, including the modifications indicated in Table 7, and the antisense strand sequence is selected from the group consisting of SEQ ID NOs 270, 271, 272, 273 and 274, including the modifications indicated in Table 8.

iii) the sense strand sequence is selected from the group consisting of SEQ ID NOs 236, 240 and 241, including the modifications indicated in Table 7, and the antisense strand sequence is selected from the group consisting of SEQ ID NOs 275, 276, 277, 278 and 279, including the modifications indicated in Table 8;

iv) the sense strand sequence is selected from the group consisting of SEQ ID NOs 242, 246 and 247, including the modifications indicated in Table 7, and the antisense strand sequence is selected from the group consisting of SEQ ID NOs 281, 282, 283, 284 and 285, including the modifications indicated in Table 8;

v) the sense strand sequence is selected from the group consisting of SEQ ID NOs 248 and 252, including the modifications indicated in Table 7, and the antisense strand sequence is selected from the group consisting of SEQ ID NOs 287, 288, 289, 290 and 291, including the modifications indicated in Table 8;

vi) the sense strand sequence is selected from the group consisting of SEQ ID NOs 253 and 257, including the modifications indicated in Table 7, and the antisense strand sequence is selected from the group consisting of SEQ ID NOs 292, 293, 294, 295 and 296, including the modifications indicated in Table 8; or vii) the sense strand sequence is selected from the group consisting of SEQ ID NOs 258, 262 and 263, including the modification indicated in Table 7, and the antisense strand sequence is selected from the group consisting of SEQ ID NOs 297, 298, 299, 300 and 301, including the modifications indicated in Table 8.

Aspects of the invention relate to methods for treating retinitis pigmentosa, Addison's disease, neuroblastoma, glioblastoma or Parkinson's disease comprising administering to a subject in need thereof a therapeutically effective amount of a nucleic acid molecule that is directed against a gene encoding tyrosinase (TYR).

In some embodiments, the nucleic acid molecule is a chemically modified oligonucleotide. In some embodiments, the nucleic acid molecule is a double stranded nucleic acid molecule. In some embodiments, the nucleic acid molecule is an isolated double stranded nucleic acid molecule that includes a double stranded region and a single stranded region, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the isolated double stranded nucleic acid molecule are modified. In some embodiments, the isolated double stranded nucleic acid molecule further comprises a hydrophobic conjugate that is attached to the isolated double stranded nucleic acid molecule Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE FIGURES

The accompanying drawings are not intended to be drawn to scale. In the drawings, each identical or nearly identical component that is illustrated in various figures is represented by a like numeral. For purposes of clarity, not every component may be labeled in every drawing. In the drawings:

In FIG. 2A, for each sample, the order of bars on the graph corresponds to: 1 µM, 0.5 µM, 0.1 µM, 0.05 µM, 0.025 µM and 0.01 µM. In FIG. 2B, the order of bars on the graph corresponds to: 1 µM, 0.5 µM, 0.1 µM, 0.05 µM and 0.01 µM.

FIG. 5A and FIG. 5B show MMP-1 and TYR compound potency improved by chemical optimization. For each sample, the order of bars on the graphs corresponds to: 0.01 µM, 0.025 µM, 0.1 µM, 0.5 µM and 1.0 µM.

FIG. 6A shows that a dose-dependent reduction of MMP1 mRNA levels were observed when HT-1080 cells were treated with MMP1-targeting sd-rxRNA MMP1-23. FIG. 6B shows that a dose-dependent reduction in MMP1 enzyme activity was observed when HT-1080 cells were treated with MMP1-targeting sd-rxRNA MMP1-23.

FIG. 7A shows a scratch migration assay in A549 non-small cell lung carcinoma cell line. FIG. 7B shows cells in culture treated with MMP1-targeting sd-rxRNA, non-targeting control (NTC), or untreated control (UTC). Reduced migration in the scratch assay may indicate a reduction in the invasive nature of the cancer cell due to MMP1 reduction as a result of sd-rxRNA treatment.

DETAILED DESCRIPTION

Figures 1A, 1B:
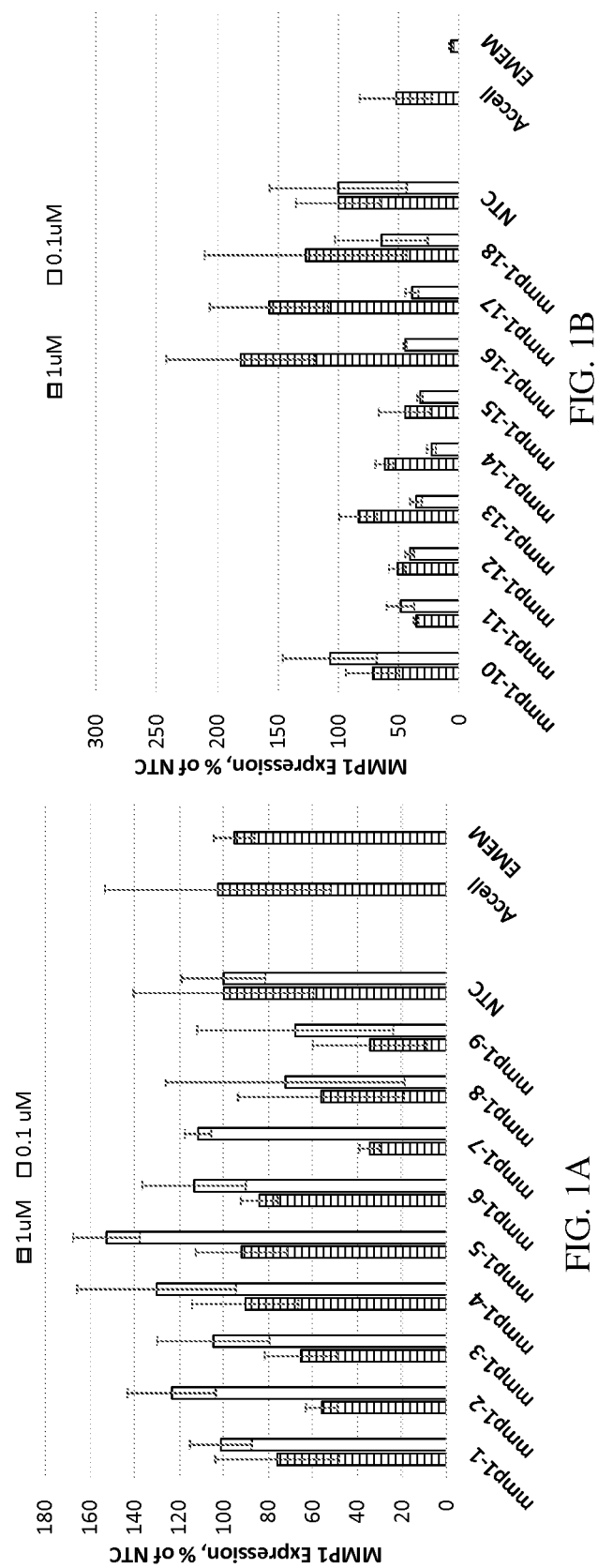
FIGS. 1A-1C show the identification of MMP1-targeting sd-rxRNAs. MMP1-targeting sd-rxRNAs within Tables 1 and 2 significantly reduce target gene mRNA levels in vitro in HT-1080 cells. For each sample, 1 µM is shown on the left and 0.1 µM is shown on the right.

As used herein, "nucleic acid molecule" includes but is not limited to: sd-rxRNA, rxRNAori, oligonucleotides, ASO, siRNA, shRNA, miRNA, ncRNA, cp-lasiRNA, aiRNA, BMT-101, RXI-109, EXC-001, single-stranded nucleic acid molecules, double-stranded nucleic acid molecules, RNA and DNA. In some embodiments, the nucleic acid molecule is a chemically modified nucleic acid molecule, such as a chemically modified oligonucleotide.

sd-rxRNA Molecules

Aspects of the invention relate to sd-rxRNA molecules. As used herein, an "sd-rxRNA" or an "sd-rxRNA molecule" refers to a self-delivering RNA molecule such as those described in, and incorporated by reference from, U.S. Pat. No. 8,796,443, granted on Aug. 5, 2014, entitled "REDUCED SIZE SELF-DELIVERING RNAI COMPOUNDS" and PCT Publication No. WO2010/033247 (Application No. PCT/US2009/005247), filed on Sep. 22, 2009, and entitled "REDUCED SIZE SELF-DELIVERING RNAI COMPOUNDS." Briefly, an sd-rxRNA, (also referred to as an sd-rxRNA$^{nano}$) is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications. In preferred embodiments, the double stranded nucleic acid molecule has one end that is blunt or includes a one or two nucleotide overhang. sd-rxRNA molecules can be optimized through chemical modification, and in some instances through attachment of hydrophobic conjugates.

In some embodiments, an sd-rxRNA comprises an isolated double stranded nucleic acid molecule comprising a guide strand and a passenger strand, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the double stranded nucleic acid are modified.

The polynucleotides of the invention are referred to herein as isolated double stranded or duplex nucleic acids, oligonucleotides or polynucleotides, nano molecules, nano RNA, sd-rxRNA$^{nano}$, sd-rxRNA or RNA molecules of the invention.

sd-rxRNAs are much more effectively taken up by cells compared to conventional siRNAs. These molecules are highly efficient in silencing of target gene expression and offer significant advantages over previously described RNAi molecules including high activity in the presence of serum, efficient self delivery, compatibility with a wide variety of linkers, and reduced presence or complete absence of chemical modifications that are associated with toxicity.

In contrast to single-stranded polynucleotides, duplex polynucleotides have traditionally been difficult to deliver to a cell as they have rigid structures and a large number of negative charges which makes membrane transfer difficult. sd-rxRNAs however, although partially double-stranded, are recognized in vivo as single-stranded and, as such, are capable of efficiently being delivered across cell membranes. As a result the polynucleotides of the invention are capable in many instances of self delivery. Thus, the polynucleotides of the invention may be formulated in a manner similar to conventional RNAi agents or they may be delivered to the cell or subject alone (or with non-delivery type carriers) and allowed to self deliver. In one embodiment of the present invention, self delivering asymmetric double-stranded RNA molecules are provided in which one portion of the molecule resembles a conventional RNA duplex and a second portion of the molecule is single stranded.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. This class of RNAi like compounds have superior efficacy in vitro and in vivo. It is believed that the reduction in the size of the rigid duplex region in combination with phosphorothioate modifications applied to a single stranded region contribute to the observed superior efficacy.

Methods of effectively administering sd-rxRNA to the skin and silencing gene expression have been demonstrated in U.S. Pat. No. 8,664,189, granted on Mar. 4, 2014 and entitled "RNA INTERFERENCE IN SKIN INDICATIONS," US Patent Publication No. US2014/0113950, filed on Apr. 4, 2013 and entitled "RNA INTERFERENCE IN DERMAL AND FIBROTIC INDICATIONS," PCT Publication No. WO 2010/033246, filed on Sep. 22, 2009 and entitled "RNA INTERFERENCE IN SKIN INDICATIONS" and PCT Publication No. WO2011/119887, filed on Mar. 24, 2011 and entitled "RNA INTERFERENCE IN DERMAL AND FIBROTIC INDICATIONS." Each of the above-referenced patents and publications are incorporated by reference herein in their entireties.

For example, FIG. 42 in US Patent Publication No. US2014/0113950 demonstrates CTGF silencing following intradermal injection of RXI-109 in vivo (Rat skin) after two intradermal injections of RXI-109 (CTGF-targeting sd-rxRNA). Data presented are from a study using an excisional wound model in rat dermis. Following two intradermal injections of RXI-109, silencing of CTGF vs. non-targeting control was sustained for at least five days. The reduction of CTGF mRNA was dose dependent: 51 and 67% for 300 and 600 μg, respectively, compared to the dose matched non-targeting control. Methods: RXI-109 or non-targeting control (NTC) was administered by intradermal injection (300 or 600 ug per 200 uL injection) to each of four sites on the dorsum of rats on Days 1 and 3. A 4 mm excisional wound was made at each injection site ~30 min after the second dose (Day 3). Terminal biopsy samples encompassing the wound site and surrounding tissue were harvested on Day 8. RNA was isolated and subjected to gene expression analysis by qPCR. Data are normalized to the level of the TATA box binding protein (TBP) housekeeping gene and graphed relative to the PBS vehicle control set at 1.0. Error bars represent standard deviation between the individual biopsy samples. P values for RXI-109-treated groups vs dose-mathced non-targeting control groups were ** $p<0.001$ for 600 μg, * $p<0.01$ for 300 μg.

It should be appreciated that the sd-rxRNA molecules disclosed herein can be administered to the skin in the same manner as the sd-rxRNA molecules disclosed in US Patent Publication No. US2014/0113950, incorporated by reference in its entirety.

Matrix Metalloproteinases

In some aspects, the instant disclosure relates to the use of nucleic acids, such as sd-rxRNA, targeting matrix metalloproteinases (MMPs). As used herein, "matrix metalloproteinase" refers to a zinc-dependent endopeptidase that is capable of degrading extracellular matrix proteins, including but not limited to collagen, gelatin, fibronectin, laminin, cholesterol sulfate, aggrecan, fibrinogen and fibrin. MMPs have been linked to several cell behaviors, for example cell proliferation, cell migration, cell differentiation, angiogenesis, apoptosis and immune function. Several genes encode MMPs, including but not limited to MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A/B, MMP24, MMP25, MMP26, MMP27 and MMP28. In some embodiments, the sd-rxRNA targets an MMP that degrades or breaks down interstitial collagen. In some embodiments, the interstitial collagen is collagen I, collagen II and/or collagen III. In some embodiments, the sd-rxRNA targets MMP1.

Tyrosinase

In some aspects, the instant disclosure relates to the use of nucleic acids, such as sd-rxRNA, targeting tyrosinase. As used herein, "tyrosinase" refers to an oxidase that controls the rate limiting step for melanin production, the hydroxylation of tyrosine and oxidation Dopa to Dopaquinone. Tyrosinase is encoded by the TYR gene. In some embodiments, the sd-rxRNA targets TYR.

In a preferred embodiment the RNAi compounds of the invention comprise an asymmetric compound comprising a duplex region (required for efficient RISC entry of 8-15 bases long) and single stranded region of 4-12 nucleotides long. In some embodiments, the duplex region is 13 or 14 nucleotides long. A 6 or 7 nucleotide single stranded region is preferred in some embodiments. The single stranded region of the new RNAi compounds also comprises 2-12 phosphorothioate internucleotide linkages (referred to as phosphorothioate modifications). 6-8 phosphorothioate internucleotide linkages are preferred in some embodiments. Additionally, the RNAi compounds of the invention also include a unique chemical modification pattern, which provides stability and is compatible with RISC entry. The combination of these elements has resulted in unexpected properties which are highly useful for delivery of RNAi reagents in vitro and in vivo.

The chemical modification pattern, which provides stability and is compatible with RISC entry includes modifications to the sense, or passenger, strand as well as the antisense, or guide, strand. For instance the passenger strand can be modified with any chemical entities which confirm stability and do not interfere with activity. Such modifications include 2' ribo modifications (O-methyl, 2' F, 2 deoxy and others) and backbone modification like phosphorothioate modifications. A preferred chemical modification pattern in the passenger strand includes Omethyl modification of C and U nucleotides within the passenger strand or alternatively the passenger strand may be completely Omethyl modified.

The guide strand, for example, may also be modified by any chemical modification which confirms stability without interfering with RISC entry. A preferred chemical modification pattern in the guide strand includes the majority of C and U nucleotides being 2' F modified and the 5' end being phosphorylated. Another preferred chemical modification pattern in the guide strand includes 2' Omethyl modification of position 1 and C/U in positions 11-18 and 5' end chemical phosphorylation. Yet another preferred chemical modification pattern in the guide strand includes 2'Omethyl modification of position 1 and C/U in positions 11-18 and 5' end chemical phosphorylation and 2'F modification of C/U in positions 2-10. In some embodiments the passenger strand and/or the guide strand contains at least one 5-methyl C or U modifications.

In some embodiments, at least 30% of the nucleotides in the sd-rxRNA are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sd-rxRNA are modified. In some embodiments, 100% of the nucleotides in the sd-rxRNA are modified.

The above-described chemical modification patterns of the oligonucleotides of the invention are well tolerated and actually improved efficacy of asymmetric RNAi compounds. In some embodiments, elimination of any of the described components (Guide strand stabilization, phosphorothioate stretch, sense strand stabilization and hydrophobic conjugate) or increase in size in some instances results in sub-optimal efficacy and in some instances complete lost of efficacy. The combination of elements results in development of a compound, which is fully active following passive delivery to cells such as HeLa cells.

The sd-rxRNA can be further improved in some instances by improving the hydrophobicity of compounds using of novel types of chemistries. For example, one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. A version of sd-rxRNA compounds where multiple deoxy Uridines are present without interfering with overall compound efficacy was used. In addition major improvement in tissue distribution and cellular uptake might be obtained by optimizing the structure of the hydrophobic conjugate. In some of the preferred embodiment the structure of sterol is modified to alter (increase/decrease) C17 attached chain. This type of modification results in significant increase in cellular uptake and improvement of tissue uptake prosperities in vivo.

dsRNA formulated according to the invention also includes rxRNAori. rxRNAori refers to a class of RNA molecules described in and incorporated by reference from PCT Publication No. WO2009/102427 (Application No. PCT/US2009/000852), filed on Feb. 11, 2009, and entitled, "MODIFIED RNAI POLYNUCLEOTIDES AND USES THEREOF," and US Patent Publication No. 2011/0039914, filed on Nov. 1, 2010, and entitled "MODIFIED RNAI POLYNUCLEOTIDES AND USES THEREOF."

In some embodiments, an rxRNAori molecule comprises a double-stranded RNA (dsRNA) construct of 12-35 nucleotides in length, for inhibiting expression of a target gene, comprising: a sense strand having a 5'-end and a 3'-end, wherein the sense strand is highly modified with 2'-modified ribose sugars, and wherein 3-6 nucleotides in the central portion of the sense strand are not modified with 2'-modified ribose sugars and, an antisense strand having a 5'-end and a 3'-end, which hybridizes to the sense strand and to mRNA of the target gene, wherein the dsRNA inhibits expression of the target gene in a sequence-dependent manner.

rxRNAori can contain any of the modifications described herein. In some embodiments, at least 30% of the nucleotides in the rxRNAori are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the rxRNAori are modified. In some embodiments, 100% of the nucleotides in the sd-rxRNA are modified. In some embodiments, only the passenger strand of the rxRNAori contains modifications.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Thus, aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments, the length of the passenger strand ranges from 8-15 nucleotides long. In certain embodiments, the passenger strand is 8, 9, 10, 11, 12, 13, 14 or 15 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-15 nucleotides long. In certain embodiments, the region of the molecule that is double stranded is 8, 9, 10, 11, 12, 13, 14 or 15 nucleotides long. In certain embodiments the double stranded region is 13 or 14 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is at least 6 or at least 7 nucleotides long.

RNAi constructs associated with the invention can have a thermodynamic stability ($\Delta G$) of less than −13 kkal/mol. In some embodiments, the thermodynamic stability ($\Delta G$) is less than −20 kkal/mol. In some embodiments there is a loss of efficacy when ($\Delta G$) goes below −21 kkal/mol. In some embodiments a ($\Delta G$) value higher than −13 kkal/mol is compatible with aspects of the invention. Without wishing to be bound by any theory, in some embodiments a molecule with a relatively higher ($\Delta G$) value may become active at a relatively higher concentration, while a molecule with a relatively lower ($\Delta G$) value may become active at a relatively lower concentration. In some embodiments, the ($\Delta G$) value may be higher than −9 kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al 2004).

Without wishing to be bound by any theory, results described herein suggest that a stretch of 8-10 bp of dsRNA or dsDNA will be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If optimal thermodynamics are present and there is a double stranded portion that is preferably at least 8 nucleotides then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 2'-O-methyl, 2'-O-ethyl, 2'-fluoro, ribothymidine, C-5 propynyl-dC (pdC) and C-5 propynyl-dU (pdU); C-5 propynyl-C (pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxyCytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule.

Specifically, reduction in 2'F content of a molecule is predicted to reduce toxicity of the molecule. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, an optimal passenger strand is approximately 11-14 nucleotides in length. The passenger strand may contain modifications that confer increased stability. One or more nucleotides in the passenger strand can be 2'OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2'OMe modified. One or more of the nucleotides on the passenger strand can also be phosphate-modified such as phosphorothioate modified. The passenger strand can also contain 2' ribo, 2'F and 2 deoxy modifications or any combination of the above. Chemical modification patterns on both the guide and passenger strand can be well tolerated and a combination of chemical modifications can lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications.

Molecules associated with the invention are also optimized for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12 C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. In some embodiments, molecules that have a double stranded region of 8-15 nucleotides can be selected for use in RNAi. In some embodiments, molecules are selected based on their thermodynamic stability (ΔG). In some embodiments, molecules will be selected that have a (ΔG) of less than −13 kkal/mol. For example, the (ΔG) value may be −13, −14, −15, −16, −17, −18, −19, −21, −22 or less than −22 kkal/mol. In other embodiments, the (ΔG) value may be higher than −13 kkal/mol. For example, the (ΔG) value may be −12, −11, −10, −9, −8, −7 or more than −7 kkal/mol. It should be appreciated that ΔG can be calculated using any method known in the art. In some embodiments ΔG is calculated using Mfold, available through the Mfold internet site (mfold.bioinfo.rpi.edu/cgi-bin/rna-form1.cgi). Methods for calculating ΔG are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the sd-rxRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

In some embodiments, the 5'-stem sequence may comprise a 2'-modified ribose sugar, such as 2'-O-methyl modified nucleotide, at the $2^{nd}$ nucleotide on the 5'-end of the polynucleotide and, in some embodiments, no other modified nucleotides. The hairpin structure having such modification may have enhanced target specificity or reduced off-target silencing compared to a similar construct without the 2'-O-methyl modification at said position.

Certain combinations of specific 5'-stem sequence and 3'-stem sequence modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the sd-rxRNA structures of the present invention mediates sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments a version of sd-rxRNA compounds, which are effective in cellular uptake and inhibiting of miRNA activity are described. Essentially the compounds are similar to RISC entering version but large strand chemical modification patterns are optimized in the way to block cleavage and act as an effective inhibitor of the RISC action. For example, the compound might be completely or mostly Omethyl modified with the PS content described previously. For these types of compounds the 5' phosphorylation is not necessary. The presence of double stranded region is preferred as it is promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. The subject single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo.

As such, the RNAi constructs of the invention are useful for treating a patient with a disease characterized by the overexpression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the nucleic acids of the invention, and cells comprising such vectors or the nucleic acids. The cell may be a mammalian cell in vivo or in culture, such as a human cell.

The invention further relates to compositions comprising the subject RNAi constructs, and a pharmaceutically acceptable carrier or diluent.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

In some embodiments, the base moiety of a nucleoside may be modified. For example, a pyrimidine base may be modified at the 2, 3, 4, 5, and/or 6 position of the pyrimidine ring. In some embodiments, the exocyclic amine of cytosine may be modified. A purine base may also be modified. For example, a purine base may be modified at the 1, 2, 3, 6, 7, or 8 position. In some embodiments, the exocyclic amine of adenine may be modified. In some cases, a nitrogen atom in a ring of a base moiety may be substituted with another atom, such as carbon. A modification to a base moiety may be any suitable modification. Examples of modifications are known to those of ordinary skill in the art. In some embodiments, the base modifications include alkylated purines or pyrimidines, acylated purines or pyrimidines, or other heterocycles.

In some embodiments, a pyrimidine may be modified at the 5 position. For example, the 5 position of a pyrimidine may be modified with an alkyl group, an alkynyl group, an alkenyl group, an acyl group, or substituted derivatives thereof. In other examples, the 5 position of a pyrimidine may be modified with a hydroxyl group or an alkoxyl group or substituted derivative thereof. Also, the $N^4$ position of a pyrimidine may be alkylated. In still further examples, the pyrimidine 5-6 bond may be saturated, a nitrogen atom within the pyrimidine ring may be substituted with a carbon atom, and/or the $O^2$ and $O^4$ atoms may be substituted with sulfur atoms. It should be understood that other modifications are possible as well.

In other examples, the $N^7$ position and/or $N^2$ and/or $N^3$ position of a purine may be modified with an alkyl group or substituted derivative thereof. In further examples, a third ring may be fused to the purine bicyclic ring system and/or a nitrogen atom within the purine ring system may be substituted with a carbon atom. It should be understood that other modifications are possible as well.

Non-limiting examples of pyrimidines modified at the 5 position are disclosed in U.S. Pat. Nos. 5,591,843, 7,205,297, 6,432,963, and 6,020,483; non-limiting examples of pyrimidines modified at the $N^4$ position are disclosed in U.S. Pat. No. 5,580,731; non-limiting examples of purines modified at the 8 position are disclosed in U.S. Pat. Nos. 6,355,787 and 5,580,972; non-limiting examples of purines modified at the $N^6$ position are disclosed in U.S. Pat. Nos. 4,853,386, 5,789,416, and 7,041,824; and non-limiting examples of purines modified at the 2 position are disclosed in U.S. Pat. Nos. 4,201,860 and 5,587,469, all of which are incorporated herein by reference.

Non-limiting examples of modified bases include $N^4,N^4$-ethanocytosine, 7-deazaxanthosine, 7-deazaguanosine, 8-oxo-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, 5-methoxyuracil, 2-methylthio-$N^6$-isopentenyladenine, pseudouracil, 5-methyl-2-thiouracil, 2-thiouracil, 4-thiouracil, 5-methyluracil, 2-thiocytosine, and 2,6-diaminopurine. In some embodiments, the base moiety may be a heterocyclic base other than a purine or pyrimidine. The heterocyclic base may be optionally modified and/or substituted.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, $NHR$, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($—OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

Definitions of specific functional groups and chemical terms are described in more detail below. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2—CH_2—CH_3$), glycol ($—O—CH_2—CH_2—O—$) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(mmethoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

The terms "halo" and "halogen" as used herein refer to an atom selected from fluorine, chlorine, bromine, and iodine.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The olynucleotide may compirse a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligunucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

The nucleic acid molecules may be associated with a hydrophobic moiety for targeting and/or delivery of the molecule to a cell. In certain embodiments, the hydrophobic moiety is associated with the nucleic acid molecule through a linker. In certain embodiments, the association is through non-covalent interactions. In other embodiments, the association is through a covalent bond. Any linker known in the art may be used to associate the nucleic acid with the hydrophobic moiety. Linkers known in the art are described in published international PCT applications, WO 92/03464, WO 95/23162, WO 2008/021157, WO 2009/021157, WO 2009/134487, WO 2009/126933, U.S. Patent Application Publication 2005/0107325, U.S. Pat. Nos. 5,414,077, 5,419, 966, 5,512,667, 5,646,126, and 5,652,359, which are incorporated herein by reference. The linker may be as simple as a covalent bond to a multi-atom linker. The linker may be cyclic or acyclic. The linker may be optionally substituted. In certain embodiments, the linker is capable of being cleaved from the nucleic acid. In certain embodiments, the linker is capable of being hydrolyzed under physiological conditions. In certain embodiments, the linker is capable of being cleaved by an enzyme (e.g., an esterase or phosphodiesterase). In certain embodiments, the linker comprises a spacer element to separate the nucleic acid from the hydrophobic moiety. The spacer element may include one to thirty carbon or heteroatoms. In certain embodiments, the linker and/or spacer element comprises protonatable functional groups. Such protonatable functional groups may promote the endosomal escape of the nucleic acid molecule. The protonatable functional groups may also aid in the delivery of the nucleic acid to a cell, for example, neutralizing the overall charge of the molecule. In other embodiments, the linker and/or spacer element is biologically inert (that is, it does not impart biological activity or function to the resulting nucleic acid molecule).

In certain embodiments, the nucleic acid molecule with a linker and hydrophobic moiety is of the formulae described herein. In certain embodiments, the nucleic acid molecule is of the formula:

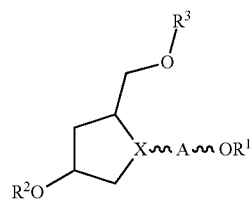

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the molecule is of the formula:

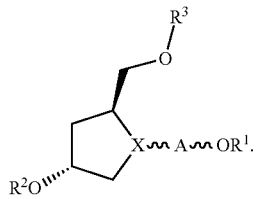

In certain embodiments, the molecule is of the formula:

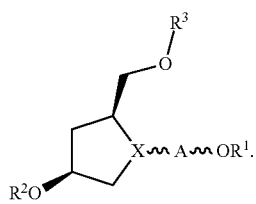

In certain embodiments, the molecule is of the formula:

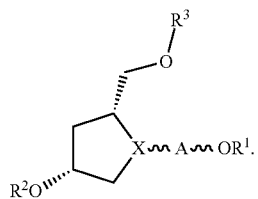

In certain embodiments, the molecule is of the formula:

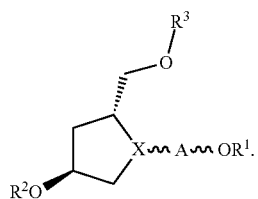

In certain embodiments, X is N. In certain embodiments, X is CH.

In certain embodiments, A is a bond. In certain embodiments, A is substituted or unsubstituted, cyclic or acyclic, branched or unbranched aliphatic. In certain embodiments, A is acyclic, substituted or unsubstituted, branched or unbranched aliphatic. In certain embodiments, A is acyclic, substituted, branched or unbranched aliphatic. In certain embodiments, A is acyclic, substituted, unbranched aliphatic. In certain embodiments, A is acyclic, substituted, unbranched alkyl. In certain embodiments, A is acyclic, substituted, unbranched $C_{1-20}$ alkyl. In certain embodiments, A is acyclic, substituted, unbranched $C_{1-12}$ alkyl. In certain embodiments, A is acyclic, substituted, unbranched $C_{1-10}$ alkyl. In certain embodiments, A is acyclic, substituted, unbranched $C_{1-8}$ alkyl. In certain embodiments, A is acyclic, substituted, unbranched $C_{1-6}$ alkyl. In certain embodiments, A is substituted or unsubstituted, cyclic or acyclic, branched or unbranched heteroaliphatic. In certain embodiments, A is acyclic, substituted or unsubstituted, branched or unbranched heteroaliphatic. In certain embodiments, A is acyclic, substituted, branched or unbranched heteroaliphatic. In certain embodiments, A is acyclic, substituted, unbranched heteroaliphatic.

In certain embodiments, A is of the formula:

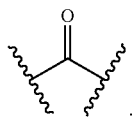

In certain embodiments, A is of one of the formulae:

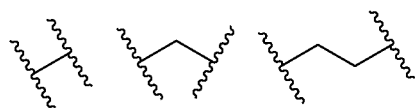

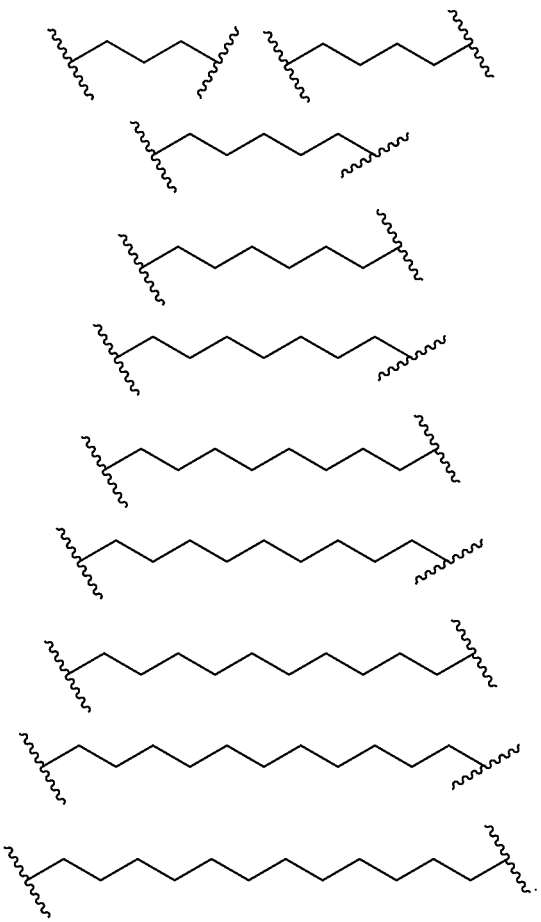

In certain embodiments, A is of one of the formulae:

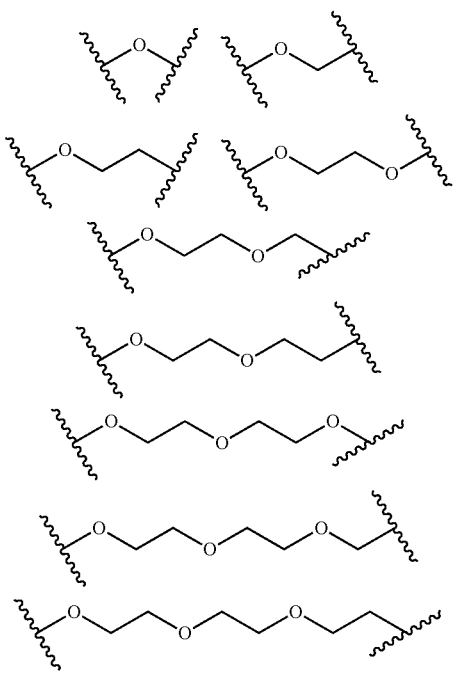

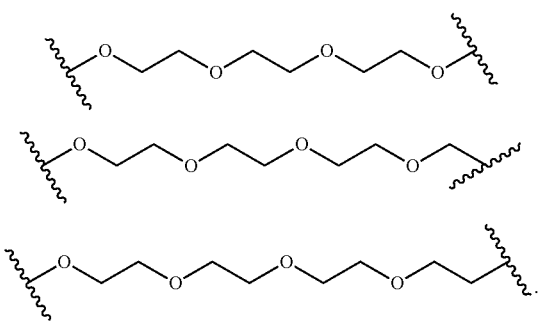

In certain embodiments, A is of one of the formulae:

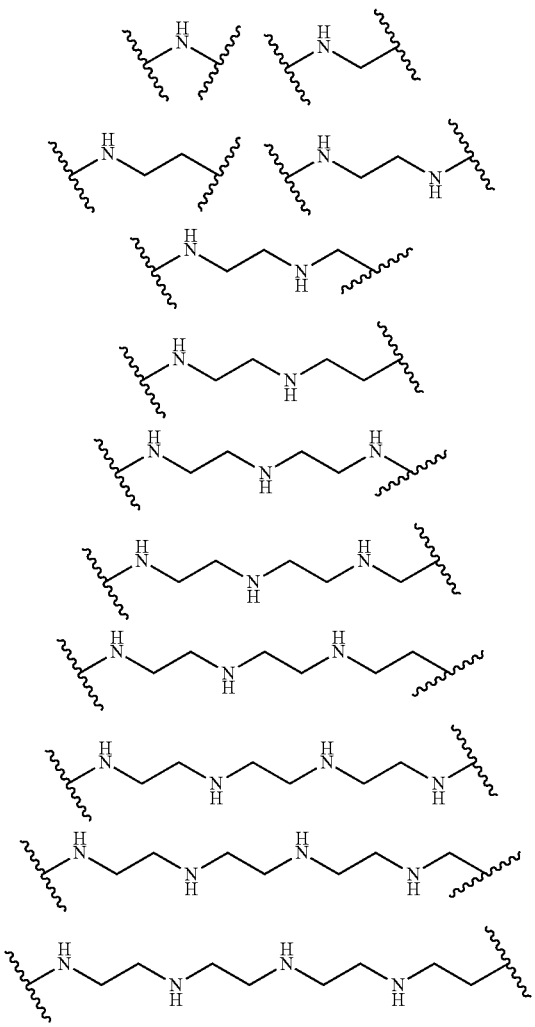

In certain embodiments, A is of the formula:

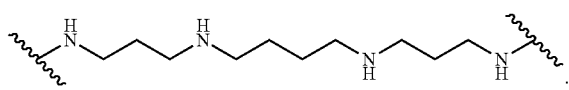 [SMILES: *NCCCNCCCCNCCCN*]

In certain embodiments, A is of the formula:

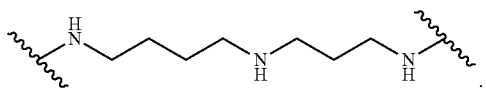 [SMILES: *NCCCCNCCCN*]

In certain embodiments, A is of the formula:

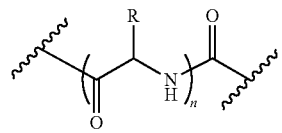

wherein
each occurrence of R is independently the side chain of a natural or unnatural amino acid; and
n is an integer between 1 and 20, inclusive. In certain embodiments, A is of the formula:

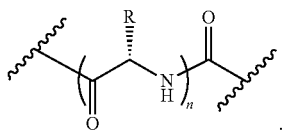

In certain embodiments, each occurrence of R is independently the side chain of a natural amino acid. In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

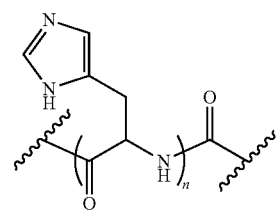

wherein n is an integer between 1 and 20, inclusive. In certain embodiments, A is of the formula:

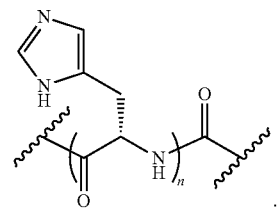

In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

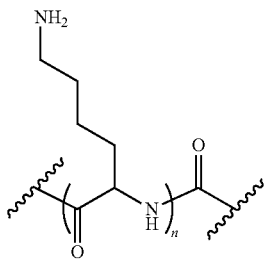

wherein n is an integer between 1 and 20, inclusive. In certain embodiments, A is of the formula:

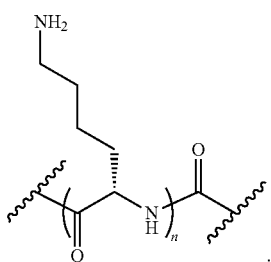

In certain embodiments, n is an integer between 1 and 15, inclusive. In certain embodiments, n is an integer between 1 and 10, inclusive. In certain embodiments, n is an integer between 1 and 5, inclusive.

In certain embodiments, the molecule is of the formula:

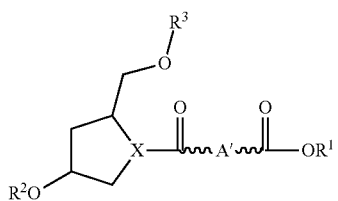

wherein X, $R^1$, $R^2$, and $R^3$ are as defined herein; and

A' is substituted or unsubstituted, cyclic or acyclic, branched or unbranched aliphatic; or substituted or unsubstituted, cyclic or acyclic, branched or unbranched heteroaliphatic.

In certain embodiments, A' is of one of the formulae:

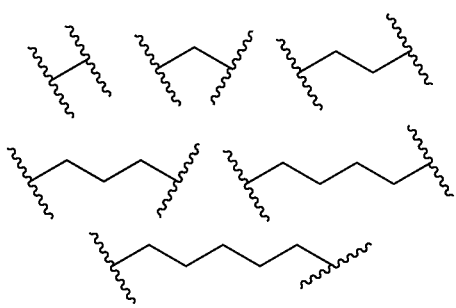

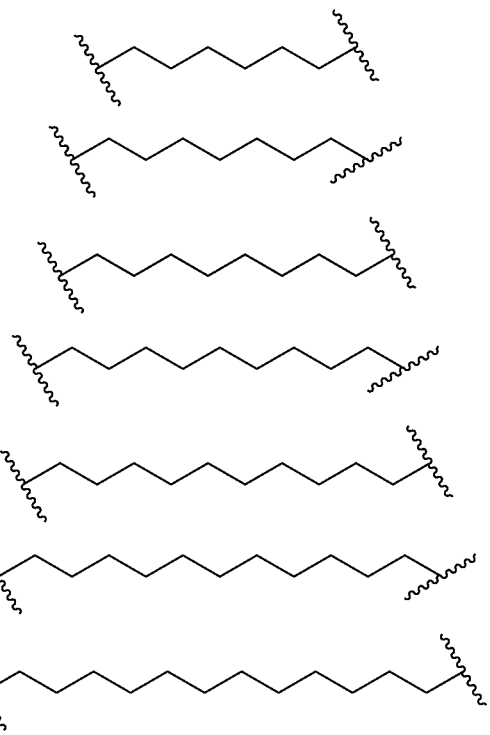

In certain embodiments, A is of one of the formulae:

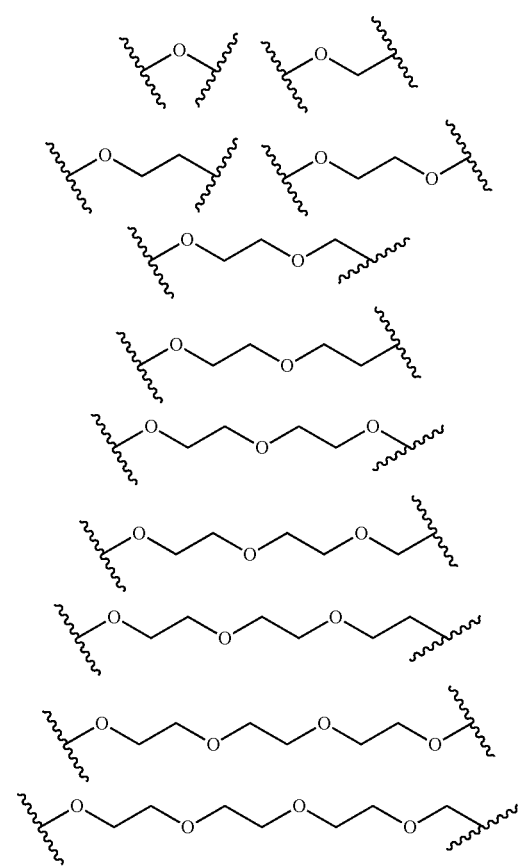

-continued

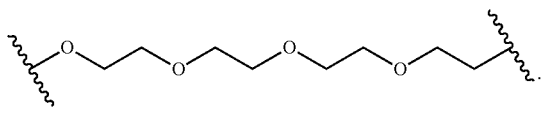

In certain embodiments, A is of one of the formulae:

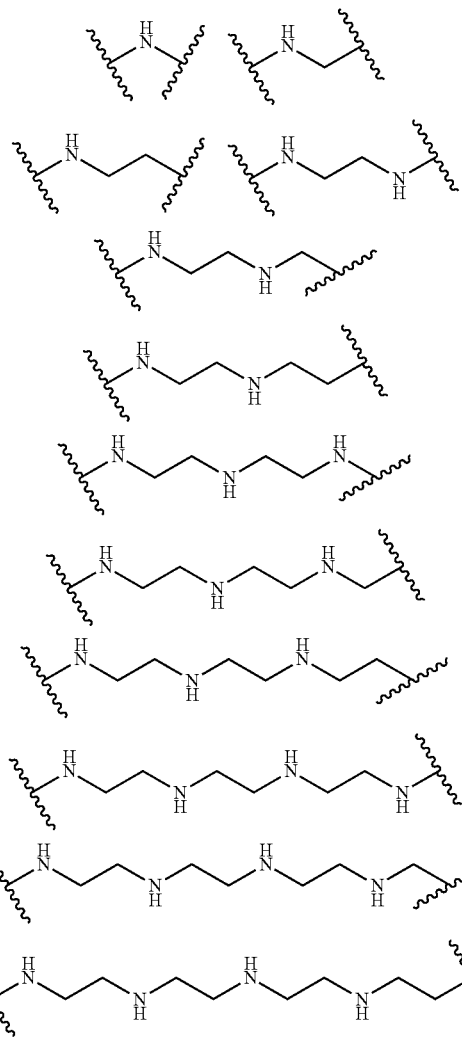

In certain embodiments, A is of the formula:

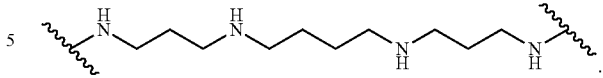

In certain embodiments, A is of the formula:

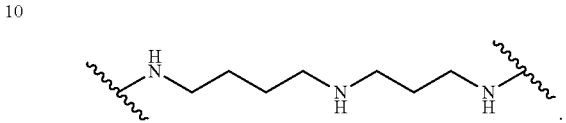

In certain embodiments, $R^1$ is a steroid. In certain embodiments, $R^1$ is a cholesterol. In certain embodiments, $R^1$ is a lipophilic vitamin. In certain embodiments, $R^1$ is a vitamin A. In certain embodiments, $R^1$ is a vitamin E.

In certain embodiments, $R^1$ is of the formula:

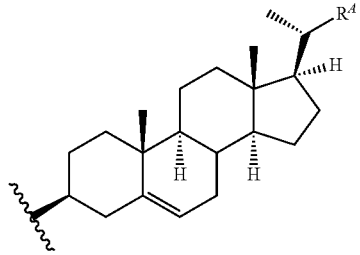

wherein $R^A$ is substituted or unsubstituted, cyclic or acyclic, branched or unbranched aliphatic; or substituted or unsubstituted, cyclic or acyclic, branched or unbranched hetero aliphatic.

In certain embodiments, $R^1$ is of the formula:

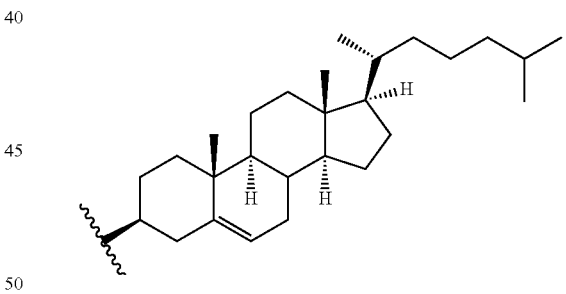

In certain embodiments, $R^1$ is of the formula:

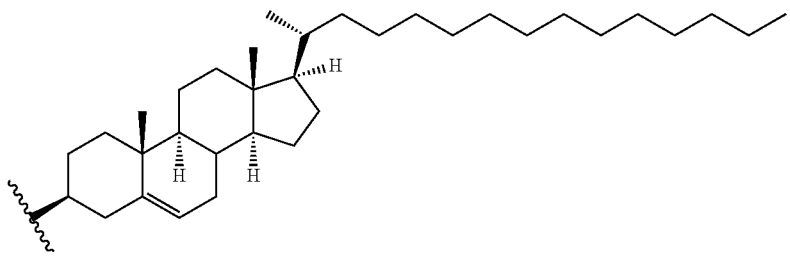

In certain embodiments, $R^1$ is of the formula:

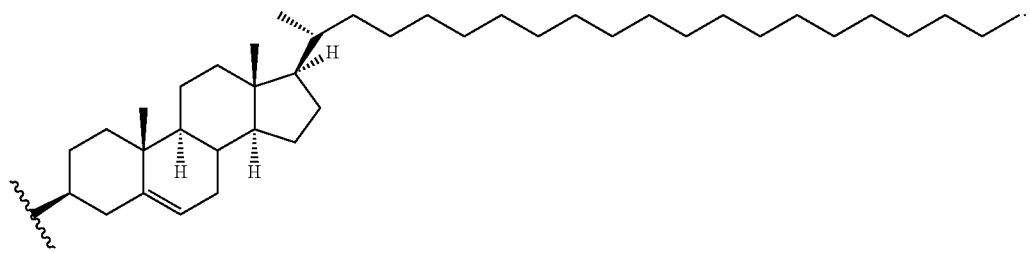

In certain embodiments, $R^1$ is of the formula:

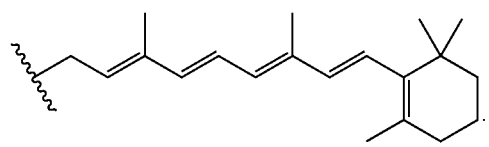 [SMILES: *C/C=C(C)/C=C/C=C(C)/C=C/C1=C(C)CCCC1(C)C]

In certain embodiments, $R^1$ is of the formula:

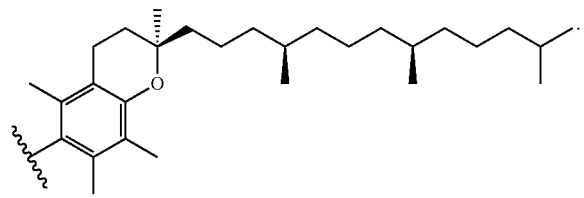 [SMILES: *c1c(C)c(C)c2c(c1C)CC[C@@](C)(CCC[C@H](C)CCC[C@H](C)CCCC(C)C)O2]

In certain embodiments, the nucleic acid molecule is of the formula:

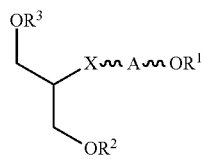

wherein
  X is N or CH;
  A is a bond; substituted or unsubstituted, cyclic or acyclic, branched or unbranched aliphatic; or substituted or unsubstituted, cyclic or acyclic, branched or unbranched heteroaliphatic;
  $R^1$ is a hydrophobic moiety;
  $R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and
  $R^3$ is a nucleic acid.

In certain embodiments, the nucleic acid molecule is of the formula:

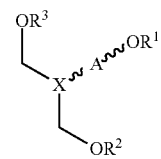

wherein
  X is N or CH;
  A is a bond; substituted or unsubstituted, cyclic or acyclic, branched or unbranched aliphatic; or substituted or unsubstituted, cyclic or acyclic, branched or unbranched heteroaliphatic;
  $R^1$ is a hydrophobic moiety;
  $R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and
  $R^3$ is a nucleic acid.

In certain embodiments, the nucleic acid molecule is of the formula:

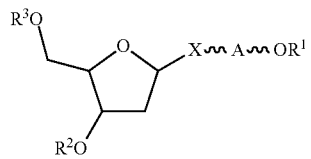

wherein
  X is N or CH;
  A is a bond; substituted or unsubstituted, cyclic or acyclic, branched or unbranched aliphatic; or substituted or unsubstituted, cyclic or acyclic, branched or unbranched heteroaliphatic;
  $R^1$ is a hydrophobic moiety;
  $R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl; and R³ is a nucleic acid. In certain embodiments, the nucleic acid molecule is of the formula:

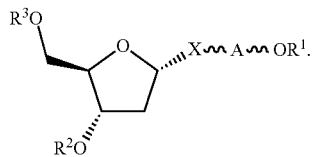

In certain embodiments, the nucleic acid molecule is of the formula:

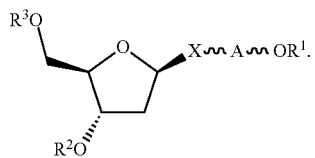

In certain embodiments, the nucleic acid molecule is of the formula:

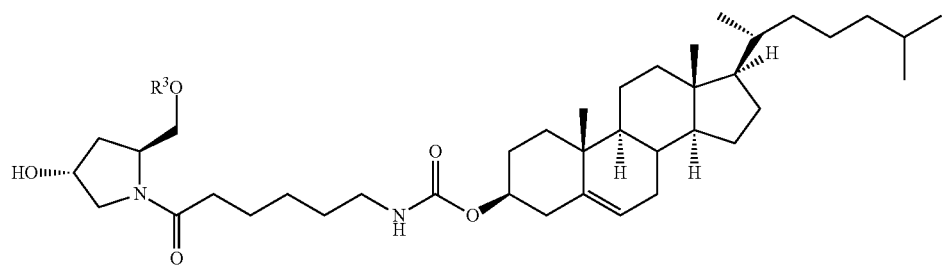

wherein R³ is a nucleic acid.

In certain embodiments, the nucleic acid molecule is of the formula:

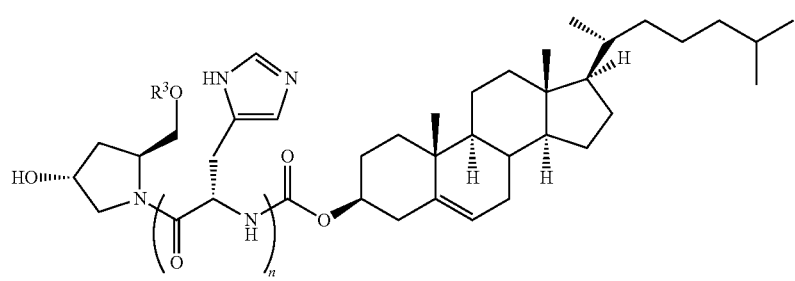

wherein $R^3$ is a nucleic acid; and
n is an integer between 1 and 20, inclusive.
In certain embodiments, the nucleic acid molecule is of the formula:
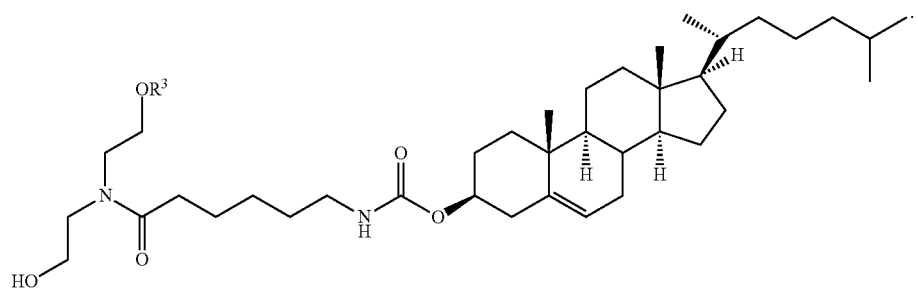
In certain embodiments, the nucleic acid molecule is of the formula:
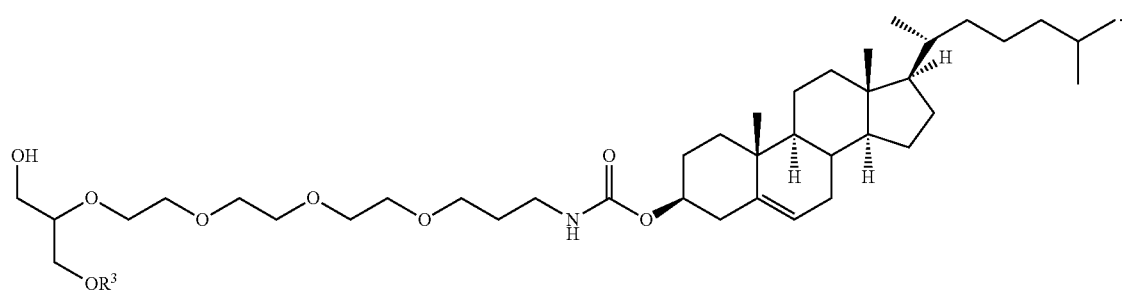
45
In certain embodiments, the nucleic acid molecule is of the formula:
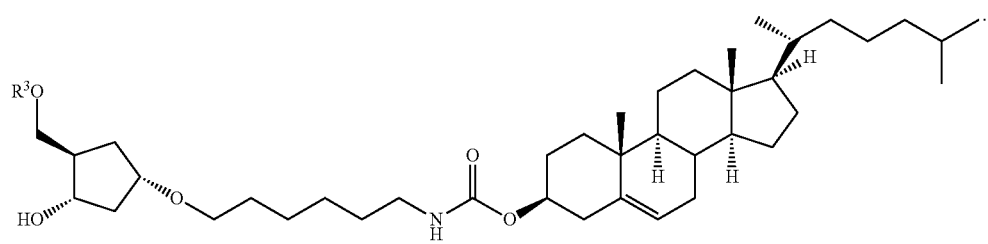

In certain embodiments, the nucleic acid molecule is of the formula:

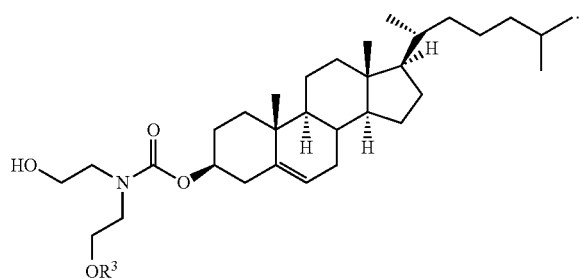

In certain embodiments, the nucleic acid molecule is of the formula:

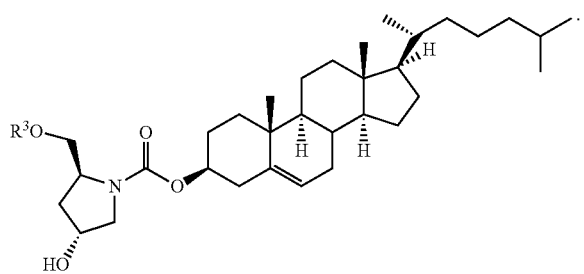

As used herein, the term "linkage" includes a naturally occurring, unmodified phosphodiester moiety (—O—(PO$^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxy-phosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise hydrophobicly modified nucleotides or "hydrophobic modifications." As used herein "hydrophobic modifications" refers to bases that are modified such that (1) overall hydrophobicity of the base is significantly increased, and/or (2) the base is still capable of forming close to regular Watson-Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl (C8H6N) CH2CH(NH2)CO), Isobutyl, butyl, aminobenzyl; phenyl; and naphthyl.

Another type of conjugates that can be attached to the end (3' or 5' end), the loop region, or any other parts of the sd-rxRNA might include a sterol, sterol type molecule, peptide, small molecule, protein, etc. In some embodiments, a sdrxRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. This allows the positioning of this 2'-modification in the Dicer-resistant hairpin structure, thus enabling one to design better RNAi constructs with less or no off-target silencing.

In one embodiment, a hairpin polynucleotide of the invention can comprise one nucleic acid portion which is DNA and one nucleic acid portion which is RNA. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed, based on the data described herein, to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. The chemical modification patterns may include combination of ribose, backbone, hydrophobic nucleoside and conjugate type of modifications. In addition, in some of the embodiments, the 5' end of the single polynucleotide may be chemically phosphorylated.

In yet another embodiment, the present invention provides a description of the chemical modifications patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier
Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. In some embodiments, Oligonucleotides are administered topically or through electroporation. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. Nucleic Acids Research. 21:3567). Enhanced delivery of oligonucleotides can also be mediated by the use of vectors (See e.g., Shi, Y. 2003. Trends Genet 2003 January 19:9; Reichhart J M et al. Genesis. 2002. 34(1-2): 1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the sd-rxRNA of the invention may be delivered by using various beta-glucan containing particles, referred to as GeRPs (glucan encapsulated RNA loaded particle), described in, and incorporated by reference from, U.S. Provisional Application No. 61/310,611, filed on Mar. 4, 2010 and entitled "Formulations and Methods for Targeted Delivery to Phagocyte Cells." Such particles are also described in, and incorporated by reference from US Patent Publications US 2005/0281781 A1, and US 2010/0040656, and in PCT publications WO 2006/007372, and WO 2007/050643. The sd-rxRNA molecule may be hydrophobically modified and optionally may be associated with a lipid and/or amphiphilic peptide. In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Glucan particles can be derived from insoluble components of fungal cell walls such as yeast cell walls. In some embodiments, the yeast is Baker's yeast. Yeast-derived glucan molecules can include one or more of β-(1,3)-Glucan, β-(1,6)-Glucan, mannan and chitin. In some embodiments, a glucan particle comprises a hollow yeast cell wall whereby the particle maintains a three dimensional structure resembling a cell, within which it can complex with or encapsulate a molecule such as an RNA molecule. Some of the advantages associated with the use of yeast cell wall particles are availability of the components, their biodegradable nature, and their ability to be targeted to phagocytic cells.

In some embodiments, glucan particles can be prepared by extraction of insoluble components from cell walls, for example by extracting Baker's yeast (Fleischmann's) with 1M NaOH/pH 4.0 H2O, followed by washing and drying. Methods of preparing yeast cell wall particles are discussed in, and incorporated by reference from U.S. Pat. Nos. 4,810,646, 4,992,540, 5,082,936, 5,028,703, 5,032,401, 5,322,841, 5,401,727, 5,504,079, 5,607,677, 5,968,811, 6,242,594, 6,444,448, 6,476,003, US Patent Publications 2003/0216346, 2004/0014715 and 2010/0040656, and PCT published application WO02/12348.

Protocols for preparing glucan particles are also described in, and incorporated by reference from, the following references: Soto and Ostroff (2008), "Characterization of multilayered nanoparticles encapsulated in yeast cell wall particles for DNA delivery." *Bioconjug Chem* 19(4):840-8; Soto and Ostroff (2007), "Oral Macrophage Mediated Gene Delivery System," *Nanotech*, Volume 2, Chapter 5 ("Drug Delivery"), pages 378-381; and Li et al. (2007), "Yeast glucan particles activate murine resident macrophages to secrete proinflammatory cytokines via MyD88- and Syk kinase-dependent pathways." *Clinical Immunology* 124(2): 170-181.

Glucan containing particles such as yeast cell wall particles can also be obtained commercially. Several non-limiting examples include: Nutricell MOS 55 from Biorigin (Sao Paolo, Brazil), SAF-Mannan (SAF Agri, Minneapolis, Minn.), Nutrex (Sensient Technologies, Milwaukee, Wis.), alkali-extracted particles such as those produced by Nutricepts (Nutricepts Inc., Burnsville, Minn.) and ASA Biotech, acid-extracted WGP particles from Biopolymer Engineering, and organic solvent-extracted particles such as Adjuvax™ from Alpha-beta Technology, Inc. (Worcester, Mass.) and microparticulate glucan from Novogen (Stamford, Conn.).

Glucan particles such as yeast cell wall particles can have varying levels of purity depending on the method of production and/or extraction. In some instances, particles are alkali-extracted, acid-extracted or organic solvent-extracted to remove intracellular components and/or the outer mannoprotein layer of the cell wall. Such protocols can produce particles that have a glucan (w/w) content in the range of 50%-90%. In some instances, a particle of lower purity, meaning lower glucan w/w content may be preferred, while in other embodiments, a particle of higher purity, meaning higher glucan w/w content may be preferred.

Glucan particles, such as yeast cell wall particles, can have a natural lipid content. For example, the particles can contain 1%, 2%, 3%, 4%, 5%, 6%, 7%, 8%, 9%, 10%, 11%, 12%, 13%, 14%, 15%, 16%, 17%, 18%, 19%, 20% or more than 20% w/w lipid. In the Examples section, the effectiveness of two glucan particle batches are tested: YGP SAF and YGP SAF+L (containing natural lipids). In some instances, the presence of natural lipids may assist in complexation or capture of RNA molecules.

Glucan containing particles typically have a diameter of approximately 2-4 microns, although particles with a diameter of less than 2 microns or greater than 4 microns are also compatible with aspects of the invention.

The RNA molecule(s) to be delivered are complexed or "trapped" within the shell of the glucan particle. The shell or RNA component of the particle can be labeled for visualization, as described in, and incorporated by reference from, Soto and Ostroff (2008) *Bioconjug Chem* 19:840. Methods of loading GeRPs are discussed further below.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

Nucleic acids associated with the invention can be hydrophobically modified and can be encompassed within neutral nanotransporters. Further description of neutral nanotransporters is incorporated by reference from PCT Application PCT/US2009/005251, filed on Sep. 22, 2009, and entitled "Neutral Nanotransporters." Such particles enable quantitative oligonucleotide incorporation into non-charged lipid mixtures. The lack of toxic levels of cationic lipids in such neutral nanotransporter compositions is an important feature.

As demonstrated in PCT/US2009/005251, oligonucleotides can effectively be incorporated into a lipid mixture that is free of cationic lipids and such a composition can effectively deliver a therapeutic oligonucleotide to a cell in a manner that it is functional. For example, a high level of activity was observed when the fatty mixture was composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non charged formulation.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is build into the oligonucleotide itself, enables efficient encapsulation of oligonucleotide in neutral lipid particles.

In some aspects, stable particles ranging in size from 50 to 140 nm can be formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

The neutral nanotransporter compositions of the invention include a hydrophobic modified polynucleotide, a neutral fatty mixture, and optionally a cargo molecule. A "hydrophobic modified polynucleotide" as used herein is a polynucleotide of the invention (i.e. sd-rxRNA) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more then 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Thus, sterols useful in the invention, for example, include cholesterols, as well as unique sterols in which position 17 has attached side chain of 2-7 or longer then 9 carbons. In a particular embodiment, the length of the polycarbon tail is varied between 5 and 9 carbons. Such conjugates may have significantly better in vivo efficacy, in particular delivery to liver. These types of molecules are expected to work at concentrations 5 to 9 fold lower then oligonucleotides conjugated to conventional cholesterols.

Alternatively the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with optimal chemical modification patterns of the polynucleotide (as described herein in detail), containing but not limited to hydrophobic modifications, phosphorothioate modifications, and 2' ribo modifications.

In another embodiment the sterol type molecule may be a naturally occurring PhytoSterols. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. In some embodiments, vitamin A or E is used. Complexes are formed at different oligonucleotide concentrations, with higher concentrations favoring more efficient complex formation.

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more then 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues.

In another embodiment the fat emulsions of the cargo molecule contain more then 70% of Linoleic acid (C18H32O2) and/or cardiolipin.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl$^-$, Br$^-$, I$^-$, F$^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Treatment Indications

In some aspects, the instant disclosure relates to the use of sd-rxRNA to target a gene associated with disease. In some embodiments, the gene associated with disease encodes a matrix metalloproteinase. In some embodiments, the matrix metalloproteinase is matrix metalloproteinase 1 (MMP1). Non-limiting examples of diseases that may be treated by a sd-rxRNA targeting MMP1 include skin disorders, arthritis (osteo and rheumatoid), acne scarring, chronic ulcers (venous ulcers), gangrene (*Vibrio* and *Clostridium*), corneal erosions, periodontitis, blistering skin disorders (e.g. Stevens-Johnson, etc.), skin photo ageing including photo damage), endometrial cancer and endometriosis.

In some embodiments, a sd-rxRNA targeting a MMP can be used to treat osteoarthritis. In some embodiments, the sd-rxRNA targets MMP1. Osteoarthritis (also known as degenerative arthritis or degenerative joint disease), a chronic condition, occurs when cartilage in joints wear down over time, resulting in pain and potentially reduced mobility of the joint. Osteoarthritis affects over 25 million people in the United States and is the most common form of arthritis. (Iannone Fl, Lapadula G., Aging Clin Exp Res. 2003 October; 15(5):364-72, incorporated herein by reference). In some embodiments, sd-rxRNA targeting MMP1 can be used to treat rheumatoid arthritis. Rheumatoid Arthritis is an autoimmune disorder, resulting in chronic inflammation of the small joints. Rheumatoid Arthritis affects over 1 million people in the United States.

In some embodiments, a sd-rxRNA targeting a MMP can be used to treat acne scarring. In some embodiments, the sd-rxRNA targets MMP1. Acne is highly prevalent among adolescents and in some cases acne lesions can result in scarring (either atrophic or hypertrophic). The healing of the lesion occurs in three stages, the last being the remodeling of the ECM. MMPs are required for this stage and overexpression of MMPs at this stage of wound healing may lead to scarring. (Fabbrocini, Annunziata, Monfrecola, Dermatology Research and Practice Volume 2010 (2010), Article ID 893080, incorporated herein by reference).

In some embodiments, asd-rxRNA targeting a MMP can be used to treat chronic ulcers. In some embodiments, the sd-rxRNA targets MMP1. Venous ulcers (stasis ulcers, varicose ulcers or ulcus cruris) affects ~1% of the US population and are the most common form of leg ulcers. Venous incompetence and venous hypertension are believed to be the primary mechanism of ulcer formation. In certain embodiments, the sd-rxRNA is used to treat chronic venous ulcers. (Collins L and Seraj S, Am Fam Physician. Apr. 15, 2010; 81(8):989-996, incorporated herein by reference).

In some embodiments, a sd-rxRNA targeting a MMP can be used to treat gangrene. In some embodiments, the sd-rxRNA targets MMP1. Gangrene, necrosis of a considerable tissue, is caused by reduced blood flow to the affected tissue due to trauma, vascular disorder or infection (*Vibrio* or *Clostridium*). Collagenases are a known virulence factor in the spread of gas gangrene.

In some embodiments, a sd-rxRNA targeting a MMP can be used to treat corneal erosions. In some embodiments, the sd-rxRNA targets MMP1. Corneal erosions or recurrent corneal erosions, occur when the outer layer of the cornea, the epithelium, detaches from the Boman's layer the basement membrane resulting in the exposure of corneal nerves. Corneal erosions may be caused by trauma or corneal disorders. Collagenase has been found to be up-regulated in patients suffering from corneal erosions. (Ramamurthi, S, Rahman, M Q, Dutton, G N and Ramaesh K, Eye (2006) 20, 635-644; published online Jul. 15, 2005, incorporated by reference herein).

In some embodiments, a sd-rxRNA targeting a MMP can be used to treat periodontitis. In some embodiments, the sd-rxRNA targets MMP1. Periodontitis (pyorrhea) is caused due to an infection of the gums and results in a chronic inflammatory disease and if left untreated may lead to the loss of the bones that support teeth.

In some embodiments, a sd-rxRNA targeting a MMP can be used to treat blistering skin disorders. In some embodiments, the sd-rxRNA targets MMP1. Non-limiting examples of blistering skin disorders include Stevens-Johnson Syndrome and Toxic Epidermal Necrolysis. In Steven Johnson syndrome and Toxic Epidermal Necrolysis the epidermis (outer layer of the skin) detaches from the dermis due to a reaction to drugs or bacterial infection.

In some embodiments, a sd-rxRNA targeting a MMP can be used to treat skin photoaging. In some embodiments, the sd-rxRNA targets MMP1. Photoaging of the skin results from repeated exposure to ultraviolet A (UVA) rays that damage collagen fibrils in the dermis. This damage results in the improper repair of the affected skin leading to wrinkles and/or leathery skin.

In some embodiments, a sd-rxRNA targeting a MMP can be used to treat endometrial cancer. In some embodiments, the sd-rxRNA targets MMP1. Endometrial cancer originates in the endometrium of the uterus (inner lining of the uterus). MMP1 was found to be up-regulated in endometrial cancers and suggested to play in role in the development and/or pathogenesis of the carcinoma. (Nishioka et al., Cancer Science, June 2000, Volume 91, Issue 6, pages 612-615, incorporated herein by reference). In some embodiments, a sd-rxRNA targeting a MMP can be used to treat endometriosis. In some embodiments, the sd-rxRNA targets MMP1. Endometriosis is a condition where the endometrium (inner lining of the uterus) grows outside of the uterus. MMP1 was found to be up-regulated in endometrial lesions, suggesting the protein is involved in the pathogenesis of endometriosis. (Lass et al., Hum. Reprod., June 2005, 20(6): 1695-1701, incorporated herein by reference).

In some embodiments, a sd-rxRNA targeting a MMP can be used to treat tuberculosis. In some embodiments, the sd-rxRNA targets MMP1. Tuberculosis is an infectious disease caused by mycobacteria (most commonly *Mycobacterium tuberculosis*) which leads to destruction of tissue, most commonly in the lung (pulmonary tuberculosis). Over one third of the world's population is believed to have been infected with tuberculosis. (Dye et al. Science., 2010; 328

(5980):856-861, incorporated herein by reference.) Collagenases have been shown to be to be upregulated in patients with tuberculosis. (Elkington et al., Volume 121, Issue 5 (May 2, 2011) J Clin Invest. 2011; 121(5):1827-1833. doi: 10.1172/JCI45666.)

In some embodiments, the gene associated with disease encodes a tyrosinase (TYR). Non-limiting examples of diseases that may be treated using a sd-rxRNA that targets TYR include cutaneous pigmentation disorders (e.g. hypermelanosis, post inflammatory hyperpigmentation, melasma, solar lentigo), freckles and lentigines (multiple lentigines syndrome), retinitis pigmentosa, Addison's disease, neuroblastoma, glioblastoma, Parkinson's disease, and keloids.

In some embodiments, a sd-rxRNA targeting TYR can be used to treat cutaneous Hyperpigmentation. Hyperpigmentation, the darkening of an area of skin, results from increased levels melanin, altered melanocyte density or both. Tyrosinase is the enzyme responsible for catalyzing the rate limiting step of the melanin biosynthetic pathway. In certain embodiments, sd-rxRNA is used to treat cutaneous hyperpigmentation. In some embodiments the sd-rxRNA targets TYR. In some embodiments, a sd-rxRNA targeting TYR can be used to treat hypermelanosis. Hypermelanosis is a darkening of the skin associated with increased levels of melanin.

In some embodiments, a sd-rxRNA targeting TYR can be used to treat inflammatory hyperpigmentation. Inflammatory hyperpigmentation of the skin may result following an occurrence of inflammation or cutaneous injury. The inflammation or injury in the skin may lead to melanocytes to increase production of melanin.

In some embodiments, a sd-rxRNA targeting TYR can be used to treat melasma. Melasma (also referred to as chloasma in pregnant woman) is an acquired form of hyperpigmentation that affects millions of people worldwide, 90% of which are women. Causes of melasma include but are not limited to ultraviolet exposure, pregnancy, hormone replacement therapy and birth control pills. Although the pathogenesis of melasma is unknown, it is hypothesized that there is an increase in active melanocytes. (Vashi, N A, British Journal of Dermatology, 2013, 169, 41-56, incorporated herein by reference). In certain embodiments, the sd-rxRNA is used to treat melasma. In some embodiments, the sd-rxRNA targets Tyrosinase.

In some embodiments, a sd-rxRNA targeting TYR can be used to treat solar lentigo. Solar lentigos, also known as sun-induced freckles, is a hyperpigmented lesion caused by repeated exposure to sun and/or ultraviolet light. The repeated exposure induce mutations leading to increases in melanin production in the affected areas.

In some embodiments, a sd-rxRNA targeting TYR can be used to treat retinitis pigmentosa. Retinitis pigmentosa is an inherited retinal degenerative disease caused by mutations in several known genes. In certain embodiments, the sd-rxRNA is used to treat retinitis pigmentosa. (Hartong, Lancet 2006, 368, 1795, incorporated herein by reference). In some embodiments, the sd-rxRNA targets TYR.

In some embodiments, a sd-rxRNA targeting TYR can be used to treat Addison's disease. Addison's disease (also known as: chronic adrenal insufficiency, hypocortisolism and hypoadrenalism) is a chronic endocrine disorder resulting in reduced levels of glucocorticoids, androgens and aldosterone. The reduction in levels of steroids leads to increases in levels of adrenocorticotropic hormone (ACTH) and melanocyte stimulating hormone (MSH) leading to the activation of melanocytes and production of melanin.

In some embodiments, a sd-rxRNA targeting TYR can be used to treat Parkinson's disease. Parkinson's disease is a neurodegenerative disease that results in the progressive loss of neurons from regions of the brain.

In some embodiments, a sd-rxRNA targeting TYR can be used to treat keloids. Keloids are scars which extend beyond the original skin injury. Keloids are a particularly aggressive form of dermal scars that do not regress. Keloid scars are raised, irregular-shaped, pink to dark red in color and characteristically extend beyond the boundaries of the original wound. Keloids are commonly tender or painful and may itch intensely. While keloids are more prevalent in darker skinned individuals and often run in families, keloids can occur in people with all skin types.

In some embodiments, a sd-rxRNA targeting TYR can be used to treat neuroblastoma. Neuroblastoma tumors, the most common extracranial solid tumor in infants, originate in neuroblasts of the sympathetic nervous system. Familial neuroblastoma is caused by mutations in several known genes. In some embodiments, a sd-rxRNA targeting TYR can be used to treat glioblastoma.

In some embodiments, the disease associated with TYR is a neoplasm. In some instances, an sd-rxRNA is targeted to a neoplasm or a neoplastic tissue and is used to ameliorate at least one symptom of a condition or disorder associated with neoplasia. Neoplasia refers to the abnormal proliferation of cells, often resulting in an abnormal mass of tissue (i.e., a neoplasm). Neoplasm may be benign, pre-malignant (e.g., a carcinoma in situ), or malignant (cancerous). Benign neoplasms include uterine fibroids and melanocytic nevi (i.e., skin moles) that do not transform into cancer. Potentially malignant, or pre-cancerous, neoplasms include carcinoma in situ, which is a early form of carcinoma that does not invade surrounding tissue, but rather proliferate in their normal environment. Malignant neoplasms are commonly referred to as cancer, and they invade and destroy surrounding tissue, may form metastases, and eventually may be fatal to the host.

In some instances, the sd-rxRNA is targeted to a neoplasm or neoplastic cells of epithelial origin. Epithelial cells reside in one or more layers which cover the entire surface of the body and which line most of the hollow structures of the body, excluding the blood vessels, lymph vessels, and the heart interior, which are lined with endothelium, and the chest and abdominal cavities which are lined with mesothelium.

Epithelial neoplasms include, but are not limited to, benign and premalignant epithelial tumors, such as breast fibroadenoma and colon adenoma, and malignant epithelial tumors. Malignant epithelial tumors include primary tumors, also referred to as carcinomas, and secondary tumors, also referred to as metastases of epithelial origin. Carcinomas include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypernephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum.

In other instances, the sd-rxRNA is targeted to a neoplasm or neoplastic cells of mesenchymal origin, for example, neoplastic cells forming a sarcoma. Sarcomas are rare mesenchymal neoplasms that arise in bone and soft tissues. Different types of sarcomas are recognized, including liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal [not bone] Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

In yet other instances, the sd-rxRNA targets neoplasms or neoplastic cells of melanocytic origin. Melanomas are tumors arising from the melanocytic system of the skin and other organs. Examples of melanoma include lentigo maligna melanoma, superficial spreading melanoma, nodular melanoma, and acral lentiginous melanoma.

In still other instances, the sd-rxRNA targets malignant neoplasms or neoplastic cells including, but not limited to, those found in biliary tract cancer, endometrial cancer, esophageal cancer, gastric cancer, intraepithelial neoplasms, including Bowen's disease and Paget's disease, liver cancer, oral cancer, including squamous cell carcinoma, sarcomas, including fibrosarcoma and osteosarcoma, skin cancer, including melanoma, Kaposi's sarcoma, testicular cancer, including germinal tumors (seminoma, non-seminoma (teratomas, choriocarcinomas)), stromal tumors and germ cell tumors, thyroid cancer, including thyroid adenocarcinoma and medullar carcinoma, and renal cancer including adenocarcinoma and Wilms tumor.

In other instances, the sd-rxRNA targets neoplasms or neoplastic cells originating in bone, muscle or connective tissue. The neoplastic cells may be found in primary tumors (e.g., sarcomas) of bone and connective tissue.

In some instances, the sd-rxRNA is delivered directly to a neoplasm, for example, by injection using a needle and syringe. Injection into the neoplasm permits large quantities of the sd-rxRNA to be delivered directly to the target cells while minimizing delivery to systemic sites. By direct injection into the neoplasm, an effective amount to promote RNA interference by the sd-rxRNA is distributed throughout at least a substantial volume of the neoplasm. In some instances, delivery of the sd-rxRNA requires a single injection into the neoplasm. In other instances, delivery of the sd-rxRNA requires multiple injections into separate regions of the neoplasm such that the entire mass of the neoplasm is invested with an effective amount to promote RNA interference by the sd-rxRNA. See U.S. Pat. Nos. 5,162,115 and 5,051,257, and Livraghi et al, *Tumori* 72 (1986), pp. 81-87, each of which is incorporated herein by reference.

The total dose, concentration, volume of the sd-rxRNA delivered, and rate of delivery can be optimized for a given neoplasm type, size and architecture. The zone of RNA interference can be controlled by optimizing these parameters. The volume and concentration of the sd-rxRNA delivered into the neoplasm must be sufficient to promote RNA interference throughout the tumor. Depending on the number of injections, and their placement with respect to neoplasm architecture, it can be useful to administer total sd-rxRNA volumes less than the neoplasm volume, greater than the neoplasm volume, or approximately equal to the neoplasm volume.

In some instances, the sd-rxRNA is delivered directly to the neoplasm using an implantable device.

In some instances sd-rxRNA injection into a neoplasm can be accompanied by ultrasound guidance.

In other instances, the sd-rxRNA is administered systemically, for example, intravenously, intraarterially, intramuscularly, or subcutaneously.

In some embodiments, an sd-rxRNA that is targeted to a neoplasm targets a proliferative gene or a gene that is expressed at higher levels in a neoplastic tissue than in other tissues. A "proliferative gene," as referred to herein, can be any gene that promotes, directly or indirectly, increased rate of growth or replication of cells, resulting in formation of a neoplasm or neoplastic cells. Increase rate of growth or replication resulting from expression/function of a proliferative gene is relative to the rate of growth or replication of non-neoplastic tissue of similar origin (e.g., neoplasms of the skin v. non-neoplastic skin). Several non-limiting examples of proliferative genes or genes that are expressed at higher levels in a neoplastic tissue than in other tissues include VEGF/VEGFR, HER2, PDGF/PDGFR, HDAC, MET, c-kit, CDK, FLT-1, IGF/IGFR, FGF/FGFR, Ras/Raf, Abl, Bcl-2, Src, mTOR, PKC, MAPK, BIRC5, FAS, HIF1A, CDH16, MYC, HRAS, and CTNNB1.

Vascular endothelial growth factor (VEGF) is a member of the PDGF/VEGF growth factor family and encodes a protein that is often found as a disulfide linked homodimer. This protein is a glycosylated mitogen that specifically acts on endothelial cells and has various effects, including mediating increased vascular permeability, inducing angiogenesis, vasculogenesis and endothelial cell growth, promoting cell migration, and inhibiting apoptosis. Elevated levels of this protein is linked to POEMS syndrome, also known as Crow-Fukase syndrome. Mutations in this gene have been associated with proliferative and nonproliferative diabetic retinopathy. Alternatively spliced transcript variants, encoding either freely secreted or cell-associated isoforms, have been characterized, and can be targeted with sd-rxRNAs of the present invention. There is also evidence for the use of non-AUG (CUG) translation initiation sites upstream of, and in-frame with the first AUG, leading to additional isoforms. A representative example of a transcript variant of human VEGFA is Genbank accession number NM_001025366.2. Its corresponding protein is Genbank accession number NP_001020537.2.

Platelet-derived growth factor (PDGFA/PDGFB) is a member of the platelet-derived growth factor family. The four members of this family are mitogenic factors for cells of mesenchymal origin and are characterized by a motif of eight cysteines. The PDGF gene product can exist either as a homodimer or as a heterodimer with the platelet-derived growth factor beta polypeptide, where the dimers are connected by disulfide bonds. Studies using knockout mice have shown cellular defects in oligodendrocytes, alveolar smooth muscle cells, and Leydig cells in the testis; knockout mice die either as embryos or shortly after birth. Two splice variants have been identified for PDGF, and can be targeted by the sd-rxRNA of the present invention. Representative examples of human PDGF transcripts are GenBank accession numbers NM_002607.5 and NM_011057.3. Their corresponding proteins are Genbank accession numbers NP_002598.4 and NP_03187.2, respectively. PDGF binds to its receptor, PDGFR. A representative example of human PDGFR transcript is Genbank accession number NM_006206.4, and its corresponding protein is NP_006197.1.

Human epidermal growth factor 2 (HER2, also referred to as HER-2, NEU, NGL, TKR1, CD340, MLN 19, and ERBB2) encodes a member of the epidermal growth factor (EGF) receptor family of receptor tyrosine kinases. This protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signaling pathways, such as those involving mitogen-activated protein kinase and phosphatidylinositol-3 kinase. Allelic variations at amino acid positions 654 and 655 of isoform a (positions 624 and 625 of isoform b) have been reported, with the most common allele being Ile654/Ile655. Amplification and/or overexpression of this gene has been reported in numerous cancers, including breast and ovarian tumors. Alternative splicing results in several additional transcript variants, some encoding different isoforms. Each transcript variant can be a target of the sd-rxRNA of the present invention. A representative example of a transcript variant of HER2 is GenBank accession number NM_004448.2. Its corresponding protein is Genbank accession number NP_004439.2.

Histone deacetylase 1 (HDAC1), belongs to the histone deacetylase/acuc/alpha family and is a component of the histone deacetylase complex. It interacts with retinoblastoma tumor-suppressor protein and this complex is a key element in the control of cell proliferation and differentiation. Together with metastasis-associated protein-2, it deacetylates p53 and modulates its effect on cell growth and apoptosis. In some instances, the sd-rxRNAs can target HDAC1, retinoblastoma tumor-suppressor protein, and/or metastasis-associated protein-2. In other instances, the sd-rxRNA can target p53. A representative example of human HDAC1 transcript is Genbank accession number NM_004964.2, and its corresponding protein is Genbank accession number NP_004955.2.

Met proto-oncogene (MET), is a hepatocyte growth factor receptor and encodes tyrosine-kinase activity. The primary single chain precursor protein is post-translationally cleaved to produce the alpha and beta subunits, which are disulfide linked to form the mature receptor. Various mutations in the MET gene are associated with papillary renal carcinoma. Two transcript variants encoding different isoforms have been found for this gene, each of which can be targeted by the sd-rxRNA. A representative example of human MET transcript is Genbank accession number NM_000245.2, and its corresponding protein is Genbank accession number NP_000236.2.

V-kit Hardy-Zuckerman 4 feline sarcoma viral oncogene (KIT, also referred to as PBT, SCFR, C-Kit, or CD117), encodes the human homolog of the proto-oncogene c-kit. C-kit was first identified as the cellular homolog of the feline sarcoma viral oncogene v-kit. This protein is a type 3 transmembrane receptor for MGF (mast cell growth factor, also known as stem cell factor). Mutations in this gene are associated with gastrointestinal stromal tumors, mast cell disease, acute myelogenous lukemia, and piebaldism. Multiple transcript variants encoding different isoforms have been found for this gene, each of which can be targeted by the sd-rxRNAs. A representative example of human KIT transcript is Genbank accession number NM_000222.2, and its corresponding protein is NP_000213.1.

Cyclin-dependent kinases (CDKs) play an essential role in cell cycle control of eukaryotic cells, are phosphorylated, and thus activated by the CDK-activating kinase (CAK). CAK is a multisubunit protein that includes CDK7 (MIM 601955), cyclin H (CCNH; MIM 601953), and MAT1. MAT1 (for 'menage a trois-1') is involved in the assembly of the CAK complex. A representative example of a human CDK transcript is Genbank accession number NM_001171434.1.

Fms-related tyrosine kinase 1 (FLT-1, also referred to as FLT, VEGFR1, FLT1) encodes a member of the vascular endothelial growth factor receptor (VEGFR) family. VEGFR family members are receptor tyrosine kinases (RTKs) which contain an extracellular ligand-binding region with seven immunoglobulin (Ig)-like domains, a transmembrane segment, and a tyrosine kinase (TK) domain within the cytoplasmic domain. This protein binds to VEGFR-A, VEGFR-B and placental growth factor and plays an important role in angiogenesis and vasculogenesis. Expression of this receptor is found in vascular endothelial cells, placental trophoblast cells and peripheral blood monocytes. Multiple transcript variants encoding different isoforms have been found for this gene. Isoforms include a full-length transmembrane receptor isoform and shortened, soluble isoforms. The soluble isoforms are associated with the onset of pre-eclampsia. Each transcript variant of FLT-1 can be a target of the sd-rxRNA. A representative example of human FLT-1 transcript is Genbank accession number NM_001159920.1, and its corresponding protein is NP_00115392.1.

Insulin-like growth factors (IGFs) are similar to insulin in function and structure and are members of a family of proteins involved in mediating growth and development. IGFI protein, for example, is processed from a precursor, bound by a specific receptor, and secreted. Defects in this gene are a cause of insulin-like growth factor I deficiency. Several transcript variants encoding different isoforms have been found for these genes, each of which can be a target of the sd-rxRNA. A representative example of human IGF transcript is Genbank accession number NM_000618.3, and its corresponding protein is NP_000609.1.

Fibroblast growth factor (FGF) family members possess broad mitogenic and cell survival activities, and are involved in a variety of biological processes, including embryonic development, cell growth, morphogenesis, tissue repair, tumor growth, and invasion. FGF1, for example, functions as a modifier of endothelial cell migration and proliferation, as well as an angiogenic factor. It acts as a mitogen for a variety of mesoderm- and neuroectoderm-derived cells in vitro, thus is thought to be involved in organogenesis. Alternatively spliced transcript variants encoding distinct isoforms of several FGFs have been reported, each of which may be a target of the sd-rxRNA. A representative example of human FGF1 transcript is Genbank accession number NM_000800.3, and its corresponding protein is NP_000791.1.

Fibroblast growth factor receptor (FGFR) family members, having highly conserved amino acid sequences between members and throughout evolution, differ from one another in their ligand affinities and tissue distribution. A full-length representative protein consists of an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. FGFR1, for example, binds both acidic and basic fibroblast growth factors and is involved in limb induction. Mutations in this gene have been associated with Pfeiffer syndrome, Jackson-Weiss syndrome, Antley-Bixler syndrome, osteoglophonic dysplasia, and autosomal dominant Kallmann syndrome 2. Chromosomal aberrations involving FGFR1 are associated with stem cell myeloproliferative disorder and stem cell leukemia lymphoma syndrome. Alternatively spliced variants which encode different protein isoforms of FGFR1 family members have been described, each of which may be a target of the sd-rxRNA. A representative example of a human FGFR1 is Genbank accession number NM_001174063.1, and its corresponding protein is NP_001167534.1.

The Ras subfamily (an abbreviation of RAt Sarcoma) is a protein subfamily of small GTPases that are involved in cellular signal transduction, and is also used to designate gene subfamily of the genes encoding those proteins. Activation of Ras signaling causes cell growth, differentiation and survival. Ras is the prototypical member of the Ras superfamily of proteins which are all related in structure and regulate diverse cell behaviors. Since Ras communicates signals from outside the cell to the nucleus, mutations in ras genes can permanently activate it and cause inappropriate transmission inside the cell, even in the absence of extracellular signals. Because these signals result in cell growth and division, dysregulated Ras signaling can ultimately lead to oncogenesis and cancer. Activating mutations in Ras are found in 20-25% of all human tumors and up to 90% in specific tumor types.

KRAS, a Kirsten ras oncogene homolog from the mammalian ras gene family, encodes a protein that is a member of the small GTPase superfamily. A single amino acid substitution is responsible for an activating mutation. The transforming protein that results is implicated in various malignancies, including lung adenocarcinoma, mucinous adenoma, ductal carcinoma of the pancreas and colorectal carcinoma. Alternative splicing leads to variants encoding two isoforms that differ in the C-terminal region. Each KRAS gene variant can be a target of the sd-rxRNA. A representative example of human KRAS transcript is Genbank accession number NM_004985.3, and its corresponding protein is NP_04976.2.

HRAS, a v-HA-ras Harvey rat sarcoma viral oncogene homolog from the mammalian ras gene family, encodes a protein that undergoes a continuous cycle of de- and re-palmitoylation, which regulates its rapid exchange between the plasma membrane and the Golgi apparatus. Mutations in this gene cause Costello syndrome, a disease characterized by increased growth at the prenatal stage, growth deficiency at the postnatal stage, predisposition to tumor formation, mental retardation, skin and musculoskeletal abnormalities, distinctive facial appearance and cardiovascular abnormalities. Defects in this gene are implicated in a variety of cancers, including bladder cancer, follicular thyroid cancer, and oral squamous cell carcinoma. Multiple transcript variants, which encode different isoforms, have been identified for this gene. Each transcript variant can be a target of the sd-rxRNA. A representative example of human HRAS transcript is Genbank accession number NM_001130442.1, and its corresponding protein is NP_001123914.1.

RAF proto-oncogene serine/threonine-protein kinase also known as proto-oncogene c-RAF or simply c-Raf is an enzyme that in humans is encoded by the RAF1 gene. The c-Raf protein functions in the MAPK/ERK signal transduction pathway as part of a protein kinase cascade. c-Raf is a member of the Raf kinase family of serine/threonine-specific protein kinases, and is a MAP kinase kinase kinase (MAP3K) that functions downstream of the Ras subfamily of membrane associated GTPases to which it binds directly. Once activated, Raf-1 can phosphorylate to activate the dual specificity protein kinases MEK1 and MEK2, which, in turn, phosphorylate to activate the serine/threonine-specific protein kinases ERK1 and ERK2. Activated ERKs are pleiotropic effectors of cell physiology and play an important role in the control of gene expression involved in the cell division cycle, apoptosis, cell differentiation, and cell migration. Any one or more of c-Raf (RAF1), MEK1, MEK2, ERK1, and ERK2 may be targets of the sd-rxRNA. A representative example of human RAF1 transcript is NM_002880.3, and its corresponding protein is NP_00287.1.

Mitogen-activated protein kinase 1 (MAPK1) (also referred to as ERK, p38, p40, p41, ERK2, ERT1, MAPK2, PRKM1, PRKM2, P42MAPK, or p41mapk) encodes a member of the MAP kinase family. MAP kinases, also known as extracellular signal-regulated kinases (ERKs), act as an integration point for multiple biochemical signals, and are involved in a wide variety of cellular processes such as proliferation, differentiation, transcription regulation and development. The activation of this kinase requires its phosphorylation by upstream kinases. Upon activation, this kinase translocates to the nucleus of the stimulated cells, where it phosphorylates nuclear targets. Two alternatively spliced transcript variants encoding the same protein, but differing in the UTRs, have been reported for this gene. Each transcript variant of MAPK1 can be a target of the sdrxRNA. A representative example of human MAPK1 transcript is NM_002745.4, and its corresponding protein is NP_002736.3.

C-abl oncogene 1, non-receptor tyrosine kinase (ABL1) encodes a cytoplasmic and nuclear protein tyrosine kinase that has been implicated in processes of cell differentiation, cell division, cell adhesion, and stress response. Activity of c-Abl protein is negatively regulated by its SH3 domain, and deletion of the SH3 domain turns ABL1 into an oncogene. The t(9;22) translocation results in the head-to-tail fusion of the BCR (MIM:151410) and ABL1 genes present in many cases of chronic myelogeneous leukemia. The DNA-binding activity of the ubiquitously expressed ABL1 tyrosine kinase is regulated by CDC2-mediated phosphorylation, suggesting a cell cycle function for ABL1. The ABL1 gene is expressed as either a 6- or 7-kb mRNA transcript, with alternatively spliced first exons spliced to the common exons 2-11. Each transcript variant of ABL1 can be a target of the sd-rxRNA. A representative example of human ABL1 transcript is Genbank accession number NM_005057.4, and its corresponding protein is NP_005148.2.

B-cell CLL/lymphoma 2 (Bcl-2) encodes an integral outer mitochondrial membrane protein that blocks the apoptotic death of some cells such as lymphocytes. Constitutive expression of BCL2, such as in the case of translocation of BCL2 to Ig heavy chain locus, is thought to be the cause of follicular lymphoma. Two transcript variants, produced by alternate splicing, differ in their C-terminal ends, each of which can be a target of the sd-rxRNA. A representative example of a human Bcl-2 transcript is NM_000633.2, and its corresponding protein is NP_00624.2.

V-src sarcoma viral oncogene homolog (SRC) is highly similar to the v-src gene of Rous sarcoma virus. This proto-oncogene may play a role in the regulation of embryonic development and cell growth. The protein encoded by this gene is a tyrosine-protein kinase whose activity can be inhibited by phosphorylation by c-SRC kinase. Mutations in this gene could be involved in the malignant progression of colon cancer. Two transcript variants encoding the same protein have been found for this gene, each of which may be a target of the sd-rxRNA. A representative example of a human SRC transcript is NM_005417.3, and its corresponding protein is NP_005408.1.

Mechanistic target of rapamycin (serine/threonine kinase) (mTOR) encodes a protein belonging to a family of phosphatidylinositol kinase-related kinases. These kinases mediate cellular responses to stresses such as DNA damage and nutrient deprivation. This protein acts as the target for the cell-cycle arrest and immunosuppressive effects of the FKBP12-rapamycin complex. A representative example of a human mTOR transcript is NM_004958.3, and its corresponding protein is NP_004949.1.

Protein kinase C (PKC) encodes a family of enzymes that are involved in controlling the function of other proteins through the phosphorylation of hydroxyl groups of serine and threonine amino acid residues on these proteins. PKC enzymes in turn are activated by signals such as increases in the concentration of diacylglycerol or Ca2+. Hence PKC enzymes play important roles in several signal transduction cascades. The PKC family consists of about ten isozymes. They are divided into three subfamilies, based on their second messenger requirements: conventional (or classical), novel, and atypical. Conventional (c)PKCs contain the isoforms α, βI, βII, and γ. These require Ca2+, diacylglycerol (DAG), and a phospholipid such as phosphatidylserine for activation. Novel (n)PKCs include the δ, ε, η, and θ isoforms, and require DAG, but do not require Ca2+ for activation. Thus, conventional and novel PKCs are activated through the same signal transduction pathway as phospholipase C. On the other hand, atypical (a)PKCs (including protein kinase Mζ and ι/λ isoforms) require neither Ca2+ nor diacylglycerol for activation. The term "protein kinase C" refers to the entire family of isoforms. Any one or more of conventional, novel, and atypical PKC genes can be a target of the sd-rxRNA. A representative example of human PKC transcript is NM_005400.2, and its corresponding protein NP_005391.1.

Baculoviral IAP repeat containing 5 (BIRCS) (also referred to as API4 or EPR-1) is a member of the inhibitor of apoptosis (IAP) gene family, which encode negative regulatory proteins that prevent apoptotic cell death. IAP family members usually contain multiple baculovirus IAP repeat (BIR) domains, but this gene encodes proteins with only a single BIR domain. The encoded proteins also lack a C-terminus RING finger domain. Gene expression is high during fetal development and in most tumors yet low in adult tissues. Antisense transcripts are involved in the regulation of this gene's expression. At least four transcript variants encoding distinct isoforms have been found for this gene, each of which may be a target of the sd-rxRNA. A representative example of human BIRCS transcript is NM_001012270.1, and its corresponding protein NP_001012270.1.

Fas (TNF receptor superfamily, member 6) (FAS, also referred to as APT1, CD95, FAS1, APO-1, FASTM, ALPS1A, or TNFRSF6) encodes a member of the TNF-receptor superfamily. This receptor contains a death domain. It has been shown to play a central role in the physiological regulation of programmed cell death, and has been implicated in the pathogenesis of various malignancies and diseases of the immune system. The interaction of this receptor with its ligand allows the formation of a death-inducing signaling complex that includes Fas-associated death domain protein (FADD), caspase 8, and caspase 10. The autoproteolytic processing of the caspases in the complex triggers a downstream caspase cascade, and leads to apoptosis. This receptor has been also shown to activate NF-kappaB, MAPK3/ERK1, and MAPK8/JNK, and is found to be involved in transducing the proliferating signals in normal diploid fibroblast and T cells. Several alternatively spliced transcript variants have been described, some of which are candidates for nonsense-mediated mRNA decay (NMD). The isoforms lacking the transmembrane domain may negatively regulate the apoptosis mediated by the full length isoform. Each transcript variant may be a target of the sd-rxRNA. In some instances, the sd-rxRNA target is FADD, caspase 8, and/or caspase 10. In other instances, the sd-rxRNA target is NF-kappaB, MAPK3/ERK1 and/or MAPK8/JNK. A representative example of human BIRC5 transcript is NM_001012270.1, and its corresponding protein NP_001012270.1.

Hypoxia inducible factor 1, alpha subunit (HIF1A), is a transcription factor found in mammalian cells cultured under reduced oxygen tension that plays an essential role in cellular and systemic homeostatic responses to hypoxia. HIF1 is a heterodimer composed of an alpha subunit and a beta subunit. The beta subunit has been identified as the aryl hydrocarbon receptor nuclear translocator (ARNT). This gene encodes the alpha subunit of HIF-1. Overexpression of a natural antisense transcript (aHIF) of this gene has been shown to be associated with nonpapillary renal carcinomas. Two alternative transcripts encoding different isoforms have been identified. Each transcript variant and/or the natural antisense transcript can be a target of the sd-rxRNA. A representative example of human HIF1A transcript is NM_001530.3, and its corresponding protein NP_001521.1.

Cadherin 16, KSP-cadherin (CDH16) is a member of the cadherin superfamily, genes encoding calcium-dependent, membrane-associated glycoproteins. Mapped to a previously identified cluster of cadherin genes on chromosome 16q22.1, the gene localizes with superfamily members CDH1, CDH3, CDH5, CDH8 and CDH11. The protein consists of an extracellular domain containing 6 cadherin domains, a transmembrane region and a truncated cytoplasmic domain but lacks the prosequence and tripeptide HAV adhesion recognition sequence typical of most classical cadherins. Expression is exclusively in kidney, where the protein functions as the principal mediator of homotypic cellular recognition, playing a role in the morphogenic direction of tissue development. Alternatively spliced transcript variants encoding distinct isoforms have been identified, each of which can be a target of the sd-rxRNA. A representative example of human CDH16 transcript is NM_004062.3, and its corresponding protein NP_004053.1.

Catenin (cadherin-associated protein), beta 1 (CTNNB1) encodes a protein that is part of a complex of proteins that constitute adherens junctions (AJs). AJs are necessary for the creation and maintenance of epithelial cell layers by regulating cell growth and adhesion between cells. The encoded protein also anchors the actin cytoskeleton and may be responsible for transmitting the contact inhibition signal that causes cells to stop dividing once the epithelial sheet is complete. This protein binds to the product of the APC gene, which is mutated in adenomatous polyposis of the colon. Mutations in this gene are a cause of colorectal cancer (CRC), pilomatrixoma (PTR), medulloblastoma (MDB), and ovarian cancer. Three transcript variants encoding the same protein have been found for this gene, each of which can be a target of the sd-rxRNA. A representative example of human CTNNB1 transcript is NM_001098209.1, and its corresponding protein NP_001091679.1.

V-myc myelocytomatosis viral oncogene homolog (MYC) encodes a multifunctional, nuclear phosphoprotein that plays a role in cell cycle progression, apoptosis and cellular transformation. It functions as a transcription factor that regulates transcription of specific target genes. Mutations, overexpression, rearrangement and translocation of this gene have been associated with a variety of hematopoietic tumors, leukemias and lymphomas, including Burkitt lymphoma. There is evidence to show that alternative translation initiations from an upstream, in-frame non-AUG (CUG) and a downstream AUG start site result in the production of two isoforms with distinct N-termini. The synthesis of non-AUG initiated protein is suppressed in Burkitt's lymphomas, suggesting its importance in the normal function of this gene. Each transcript variant, including mutant variants, can be a target of the sd-rxRNA. A representative example of human MYC transcript is NM_002467.4, and its corresponding protein NP_002458.2.

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. In preferred embodiments, the sd-rxRNA molecules are administered by intradermal injection or subcutaneously.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. In some embodiments, preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimens may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Administration of sd-rxRNAs, such as through intradermal injection or subcutaneous delivery, can be optimized through testing of dosing regimens. In some embodiments, a single administration is sufficient. To further prolong the effect of the administered sd-rxRNA, the sd-rxRNA can be administered in a slow-release formulation or device, as would be familiar to one of ordinary skill in the art. The hydrophobic nature of sd-rxRNA compounds can enable use of a wide variety of polymers, some of which are not compatible with conventional oligonucleotide delivery.

In other embodiments, the sd-rxRNA is administered multiple times. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Aspects of the invention relate to administering sd-rxRNA molecules to a subject. In some instances the subject is a patient and administering the sd-rxRNA molecule involves administering the sd-rxRNA molecule in a doctor's office.

In some embodiments, more than one sd-rxRNA molecule is administered simultaneously. For example a composition may be administered that contains 1, 2, 3, 4, 5, 6, 7, 8, 9, 10 or more than 10 different sd-rxRNA molecules. In certain embodiments, a composition comprises 2 or 3 different sd-rxRNA molecules. When a composition comprises more than one sd-rxRNA, the sd-rxRNA molecules within the composition can be directed to the same gene or to different genes.

In some instances, the effective amount of sd-rxRNA that is delivered by subcutaneous administration is at least approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 mg/kg including any intermediate values.

In some instances, the effective amount of sd-rxRNA that is delivered through intradermal injection is at least approximately 1, 5, 10, 15, 20, 25, 30, 35, 40, 45, 50, 55, 60, 65, 70, 75, 80, 85, 90, 95, 100, 125, 150, 200, 250, 300, 350, 400, 450, 500, 550, 600, 650, 700, 750, 800, 850, 900, 950 or more than 950 µg including any intermediate values.

sd-rxRNA molecules administered through methods described herein are effectively targeted to all the cell types in the skin.

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of nucleic acid encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, inhibit annealing of single strands, stabilize the single strands, or other-wise increase inhibition of the target gene.

Nucleic acid may be directly introduced into the cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

A further preferred use for the agents of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable priming agent/RNAi agent which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Therapeutic Use

By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), miRNA disorders, and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. *Genetic Engineering News* 16:1. Exemplary targets for cleavage by oligonucleotides include, e.g., protein kinase Cα, ICAM-1, c-raf kinase, p53, c-myb, and the bcr/abl fusion gene found in chronic myelogenous leukemia.

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), Xenopus, fish, insects (Drosophila, etc.), and worms (*C. elegans*), etc.

The invention provides methods for preventing in a subject, a disease or condition associated with an aberrant or unwanted target gene expression or activity, by administering to the subject a therapeutic agent (e.g., a RNAi agent or vector or transgene encoding same). If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the modulatory method of the invention involves contacting a cell capable of expressing target gene with a therapeutic agent of the invention that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent), in vivo (e.g., by administering the agent to a subject), or ex vivo. Typically, subjects are first treated with a priming agent so as to be more responsive to the subsequent RNAi therapy. As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

The therapeutic agents of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266

RNAi in Skin Indications

Nucleic acid molecules, or compositions comprising nucleic acid molecules, described herein may in some embodiments be administered to pre-treat, treat or prevent compromised skin. As used herein "compromised skin" refers to skin which exhibits characteristics distinct from normal skin. Compromised skin may occur in association with a dermatological condition. Several non-limiting examples of dermatological conditions include rosacea, common acne, seborrheic dermatitis, perioral dermatitis, acneform rashes, transient acantholytic dermatosis, and acne necrotica miliaris. In some instances, compromised skin may comprise a wound and/or scar tissue. In some instances, methods and compositions associated with the invention may be used to promote wound healing, prevention, reduction or inhibition of scarring, and/or promotion of re-epithelialisation of wounds.

A subject can be pre-treated or treated prophylactically with a molecule associated with the invention, prior to the skin of the subject becoming compromised. As used herein "pre-treatment" or "prophylactic treatment" refers to administering a nucleic acid to the skin prior to the skin becoming compromised. For example, a subject could be pre-treated 15 minutes, 30 minutes, 1 hour, 2 hours, 3 hours, 4 hours, 5 hours, 6 hours, 7 hours, 8 hours, 9 hours, 10 hours, 11 hours, 12 hours, 24 hours, 48 hours, 3 days, 4 days, 5 days, 6 days, 7 days, 8 days or more than 8 days prior to the skin becoming compromised. In other embodiments, a subject can be treated with a molecule associated with the invention immediately before the skin becomes compromised and/or simultaneous to the skin becoming compromised and/or after the skin has been compromised. In some embodiments, the skin is compromised through a medical procedure such as surgery, including elective surgery. In certain embodiments methods and compositions may be applied to areas of the skin that are believed to be at risk of becoming compromised. It should be appreciated that one of ordinary skill in the art would be able to optimize timing of administration using no more than routine experimentation.

In some aspects, methods associated with the invention can be applied to promote healing of compromised skin. Administration can occur at any time up until the compromised skin has healed, even if the compromised skin has already partially healed. The timing of administration can depend on several factors including the nature of the compromised skin, the degree of damage within the compromised skin, and the size of the compromised area. In some embodiments administration may occur immediately after the skin is compromised, or 30 minutes, 1 hour, 2 hours, 4 hours, 6 hours, 8 hours, 12 hours, 24 hours, 48 hours, or more than 48 hours after the skin has been compromised. Methods and compositions of the invention may be administered one or more times as necessary. For example, in some embodiments, compositions may be administered daily or twice daily. In some instances, compositions may be administered both before and after formation of compromised skin.

Compositions associated with the invention may be administered by any suitable route. In some embodiments, administration occurs locally at an area of compromised skin. For example, compositions may be administered by intradermal injection. Compositions for intradermal injection may include injectable solutions. Intradermal injection may in some embodiments occur around the are of compromised skin or at a site where the skin is likely to become compromised. In some embodiments, compositions may also be administered in a topical form, such as in a cream or ointment. In some embodiments, administration of compositions described herein comprises part of an initial treatment or pre-treatment of compromised skin, while in other embodiments, administration of such compositions comprises follow-up care for an area of compromised skin.

The appropriate amount of a composition or medicament to be applied can depend on many different factors and can be determined by one of ordinary skill in the art through routine experimentation. Several non-limiting factors that might be considered include biological activity and bioavailability of the agent, nature of the agent, mode of administration, half-life, and characteristics of the subject to be treated.

In some aspects, nucleic acid molecules associated with the invention may also be used in treatment and/or prevention of fibrotic disorders, including pulmonary fibrosis, liver cirrhosis, scleroderma and glomerulonephritis, lung fibrosis, liver fibrosis, skin fibrosis, muscle fibrosis, radiation fibrosis, kidney fibrosis, proliferative vitreoretinopathy and uterine fibrosis.

A therapeutically effective amount of a nucleic acid molecule described herein may in some embodiments be an amount sufficient to prevent the formation of compromised skin and/or improve the condition of compromised skin. In some embodiments, improvement of the condition of compromised skin may correspond to promotion of wound healing and/or inhibition of scarring and/or promotion of epithelial regeneration. The extent of prevention of formation of compromised skin and/or improvement to the condition of compromised skin may in some instances be determined by, for example, a doctor or clinician.

The ability of nucleic acid molecules associated with the invention to prevent the formation of compromised skin and/or improve the condition of compromised skin may in some instances be measured with reference to properties exhibited by the skin. In some instances, these properties may include rate of epithelialisation and/or decreased size of an area of compromised skin compared to control skin at comparable time points.

As used herein, prevention of formation of compromised skin, for example prior to a surgical procedure, and/or improvement of the condition of compromised skin, for example after a surgical procedure, can encompass any increase in the rate of healing in the compromised skin as compared with the rate of healing occurring in a control sample. In some instances, the condition of compromised skin may be assessed with respect to either comparison of the rate of re-epithelialisation achieved in treated and control skin, or comparison of the relative areas of treated and control areas of compromised skin at comparable time points. In some aspects, a molecule that prevents formation of compromised skin or promotes healing of compromised skin may be a molecule that, upon administration, causes the area of compromised skin to exhibit an increased rate of re-epithelialisation and/or a reduction of the size of compromised skin compared to a control at comparable time points. In some embodiments, the healing of compromised skin may give rise to a rate of healing that is 5%, 10%, 20%, 30%, 40%, 50%, 60%, 70%, 80%, 90% or 100% greater than the rate occurring in controls.

In some aspects, subjects to be treated by methods and compositions associated with the invention may be subjects who will undergo, are undergoing or have undergone a medical procedure such as a surgery. In some embodiments, the subject may be prone to defective, delayed or otherwise impaired re-epithelialisation, such as dermal wounds in the aged. Other non-limiting examples of conditions or disorders in which wound healing is associated with delayed or otherwise impaired re-epithelialisation include patients suffering from diabetes, patients with polypharmacy, post-menopausal women, patients susceptible to pressure injuries, patients with venous disease, clinically obese patients, patients receiving chemotherapy, patients receiving radiotherapy, patients receiving steroid treatment, and immuno-compromised patients. In some instances, defective re-epithelialisation response can contributes to infections at the wound site, and to the formation of chronic wounds such as ulcers.

In some embodiments, methods associated with the invention may promote the re-epithelialisation of compromised skin in chronic wounds, such as ulcers, and may also inhibit scarring associated with wound healing. In other embodiments, methods associated with the invention are applied to prevention or treatment of compromised skin in acute wounds in patients predisposed to impaired wound healing developing into chronic wounds. In other aspects, methods associated with the invention are applied to promote accelerated healing of compromised skin while preventing, reducing or inhibiting scarring for use in general clinical contexts. In some aspects, this can involve the treatment of surgical incisions and application of such methods may result in the prevention, reduction or inhibition of scarring that may otherwise occur on such healing. Such treatment may result in the scars being less noticeable and exhibiting regeneration of a more normal skin structure. In other embodiments, the compromised skin that is treated is not compromised skin that is caused by a surgical incision. The compromised skin may be subject to continued care and continued application of medicaments to encourage re-epithelialisation and healing.

In some aspects, methods associated with the invention may also be used in the treatment of compromised skin associated with grafting procedures. This can involve treatment at a graft donor site and/or at a graft recipient site. Grafts can in some embodiments involve skin, artificial skin, or skin substitutes. Methods associated with the invention can also be used for promoting epithelial regeneration. As used herein, promotion of epithelial regeneration encompasses any increase in the rate of epithelial regeneration as compared to the regeneration occurring in a control-treated or untreated epithelium. The rate of epithelial regeneration attained can in some instances be compared with that taking place in control-treated or untreated epithelia using any suitable model of epithelial regeneration known in the art. Promotion of epithelial regeneration may be of use to induce effective re-epithelialisation in contexts in which the re-epithelialisation response is impaired, inhibited, retarded or otherwise defective. Promotion of epithelial regeneration may be also effected to accelerate the rate of defective or normal epithelial regeneration responses in patients suffering from epithelial damage.

Some instances where re-epithelialisation response may be defective include conditions such as pemphigus, Hailey-Hailey disease (familial benign pemphigus), toxic epidermal necrolysis (TEN)/Lyell's syndrome, epidermolysis bullosa, cutaneous leishmaniasis and actinic keratosis. Defective re-epithelialisation of the lungs may be associated with idiopathic pulmonary fibrosis (IPF) or interstitial lung disease. Defective re-epithelialisation of the eye may be associated with conditions such as partial limbal stem cell deficiency or corneal erosions. Defective re-epithelialisation of the gastrointestinal tract or colon may be associated with conditions such as chronic anal fissures (fissure in ano), ulcerative colitis or Crohn's disease, and other inflammatory bowel disorders.

In some aspects, methods associated with the invention are used to prevent, reduce or otherwise inhibit compromised skin associated with scarring. This can be applied to any site within the body and any tissue or organ, including the skin, eye, nerves, tendons, ligaments, muscle, and oral cavity (including the lips and palate), as well as internal organs (such as the liver, heart, brain, abdominal cavity, pelvic cavity, thoracic cavity, guts and reproductive tissue). In the skin, treatment may change the morphology and organization of collagen fibers and may result in making the scars less visible and blend in with the surrounding skin. As used herein, prevention, reduction or inhibition of scarring encompasses any degree of prevention, reduction or inhibition in scarring as compared to the level of scarring occurring in a control-treated or untreated wound.

Prevention, reduction or inhibition of compromised skin, such as compromised skin associated with dermal scarring, can be assessed and/or measured with reference to microscopic and/or macroscopic characteristics. Macroscopic characteristics may include color, height, surface texture and stiffness of the skin. In some instances, prevention, reduction or inhibition of compromised skin may be demonstrated when the color, height, surface texture and stiffness of the skin resembles that of normal skin more closely after treatment than does a control that is untreated. Microscopic assessment of compromised skin may involve examining characteristics such as thickness and/or orientation and/or composition of the extracellular matrix (ECM) fibers, and cellularity of the compromised skin. In some instances, prevention, reduction or inhibition of compromised skin may be demonstrated when the thickness and/or orientation and/or composition of the extracellular matrix (ECM) fibers, and/or cellularity of the compromised skin resembles that of normal skin more closely after treatment than does a control that is untreated.

In some aspects, methods associated with the invention are used for cosmetic purposes, at least in part to contribute to improving the cosmetic appearance of compromised skin. In some embodiments, methods associated with the invention may be used to prevent, reduce or inhibit compromised skin such as scarring of wounds covering joints of the body. In other embodiments, methods associated with the invention may be used to promote accelerated wound healing and/or prevent, reduce or inhibit scarring of wounds at increased risk of forming a contractile scar, and/or of wounds located at sites of high skin tension.

In some embodiments, methods associated with the invention can be applied to promoting healing of compromised skin in instances where there is an increased risk of pathological scar formation, such as hypertrophic scars and keloids, which may have more pronounced deleterious effects than normal scarring. In some embodiments, methods described herein for promoting accelerated healing of compromised skin and/or preventing, reducing or inhibiting scarring are applied to compromised skin produced by surgical revision of pathological scars.

Aspects of the invention can be applied to compromised skin caused by burn injuries. Healing in response to burn injuries can lead to adverse scarring, including the formation of hypertrophic scars. Methods associated with the invention can be applied to treatment of all injuries involving damage to an epithelial layer, such as injuries to the skin in which the epidermis is damaged. Other non-limiting examples of injuries to epithelial tissue include injuries involving the respiratory epithelia, digestive epithelia or epithelia surrounding internal tissues or organs.

RNAi to Treat Liver Fibrosis

In some embodiments, methods associated with the invention are used to treat liver fibrosis. Liver fibrosis is the excessive accumulation of extracellular matrix proteins, including collagen, that occurs in most types of chronic liver diseases. It is the scarring process that represents the liver's response to injury. Advanced liver fibrosis results in cirrhosis, liver failure, and portal hypertension and often requires liver transplantation. In the same way as skin and other organs heal wounds through deposition of collagen and other matrix constituents so the liver repairs injury through the deposition of new collagen. Activated hepatic stellate cells, portal fibroblasts, and myofibroblasts of bone marrow origin have been identified as major collagen-producing cells in the injured liver. These cells are activated by fibrogenic cytokines such as TGF-β1, angiotensin II, and leptin. In some embodiments, methods provided herein are aimed at inhibiting the accumulation of fibrogenic cells and/or preventing the deposition of extracellular matrix proteins.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1

Figure 1C:
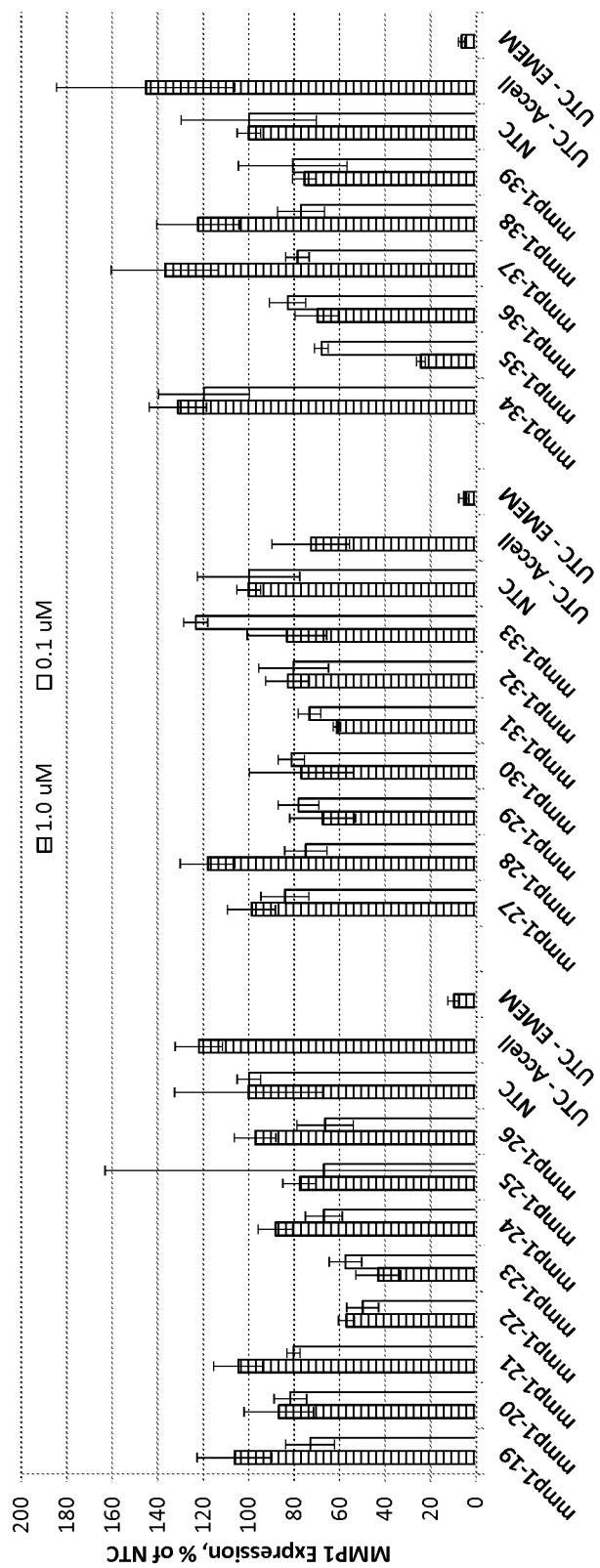

Identification of MMP1-Targeting sd-rxRNAs sd-rxRNAs targeting MMP1 were designed, synthesized and screened in vitro to determine the ability of the sd-rxRNAs to reduce target gene mRNA levels. The sd-rxRNAs were tested for activity in HT-1080 cells (human fibrosarcoma cell line, 10,000 cells/well, 96 well plate). HT-1080 cells were treated with varying concentrations of a panel of MMP1-targeting sd-rxRNAs or non-targeting control (NTC) in serum-free media. Concentrations tested were 1 and 0.1 µM. The non-targeting control sd-rxRNA (NTC) is of similar structure to the MMP1-targeting sd-rxRNA and contains similar stabilizing modifications throughout both strands. Forty-eight hours post administration, cells were lysed and mRNA levels determined by the Quantigene branched DNA assay according to the manufacture's protocol using gene-specific probes (Affymetrix). FIGS. 1A-1C demonstrate that MMP1-targeting sd-rxRNAs, found in Tables 1 and 2, significantly reduce target gene mRNA levels in vitro in HT-1080 cells. Data were normalized to a house keeping gene (PPIB) and graphed with respect to the non-targeting control. Error bars represent the standard deviation from the mean of biological triplicates.

The human MMP1 sequence is represented by GenBank accession number NM_002421.3 listed below:

```
                                              (SEQ ID NO: 1)
AGCATGAGTCAGACAGCCTCTGGCTTTCTGGAAGGGCAAGGACTCTATAT

ATACAGAGGGAGCTTCCTAGCTGGGATATTGGAGCAGCAAGAGGCTGGGA

AGCCATCACTTACCTTGCACTGAGAAAGAAGACAAAGGCCAGTATGCACA

GCTTTCCTCCACTGCTGCTGCTGCTGTTCTGGGGTGTGGTGTCTCACAGC

TTCCCAGCGACTCTAGAAACACAAGAGCAAGATGTGGACTTAGTCCAGAA

ATACCTGGAAAAATACTACAACCTGAAGAATGATGGGAGGCAAGTTGAAA
```

-continued

AGCGGAGAAATAGTGGCCCAGTGGTTGAAAAATTGAAGCAAATGCAGGAA

TTCTTTGGGCTGAAAGTGACTGGGAAACCAGATGCTGAAACCCTGAAGGT

GATGAAGCAGCCCAGATGTGGAGTGCCTGATGTGGCTCAGTTTGTCCTCA

CTGAGGGAACCCTCGCTGGGAGCAAACACATCTGACCTACAGGATTGAA

AATTACACGCCAGATTTGCCAAGAGCAGATGTGGACCATGCCATTGAGAA

AGCCTTCCAACTCTGGAGTAATGTCACACCTCTGACATTCACCAAGGTCT

CTGAGGGTCAAGCAGACATCATGATATCTTTTGTCAGGGGAGATCATCGG

GACAACTCTCCTTTTGATGGACCTGGAGGAAATCTTGCTCATGCTTTTCA

ACCAGGCCCAGGTATTGGAGGGGATGCTCATTTTGATGAAGATGAAGGT

GGACCAACAATTTCAGAGAGTACAACTTACATCGTGTTCAGCTCATGAA

CTCGGCCATTCTCTTGGACTCTCCCATTCTACTGATATCGGGGCTTTGAT

GTACCCTAGCTACACCTTCAGTGGTGATGTTCAGCTAGCTCAGGATGACA

TTGATGGCATCCAAGCCATATATGGACGTTCCCAAAATCCTGTCCAGCCC

ATCGGCCCACAAACCCCAAAAGCGTGTGACAGTAAGCTAACCTTTGATGC

TATAACTACGATTCGGGGAGAAGTGATGTTCTTTAAAGACAGATTCTACA

TGCGCACAAATCCCTTCTACCCGGAAGTTGAGCTCAATTTCATTTCTGTT

TTCTGGCCACAACTGCCAAATGGGCTTGAAGCTGCTTACGAATTTGCCGA

CAGAGATGAAGTCCGGTTTTTCAAAGGGAATAAGTACTGGGCTGTTCAGG

GACAGAATGTGCTACACGGATACCCCAAGGACATCTACAGCTCCTTTGGC

TTCCCTAGAACTGTGAAGCATATCGATGCTGCTCTTTCTGAGGAAACAC

TGGAAAAACCTACTTCTTTGTTGCTAACAAATACTGGAGGTATGATGAAT

ATAAACGATCTATGGATCCAGGTTATCCCAAAATGATAGCACATGACTTT

CCTGGAATTGGCCACAAAGTTGATGCAGTTTTCATGAAAGATGGATTTTT

CTATTTCTTTCATGGAACAAGACAATACAAATTGATCCTAAAACGAAGA

GAATTTTGACTCTCCAGAAAGCTAATAGCTGGTTCAACTGCAGGAAAAAT

TGAACATTACTAATTTGAATGGAAAACACATGGTGTGAGTCCAAAGAAGG

TGTTTTCCTGAAGAACTGTCTATTTTCTCAGTCATTTTTAACCTCTAGAG

TCACTGATACACAGAATATAATCTTATTTATACCTCAGTTTGCATATTTT

TTACTATTTAGAATGTAGCCCTTTTTGTACTGATATAATITAGTTCCACA

AATGGTGGGTACAAAAAGTCAAGTTTGTGGCTTATGGATTCATATAGGCC

AGAGTTGCAAAGATCTTTTCCAGAGTATGCAACTCTGACGTTGATCCCAG

AGAGCAGCTTCAGTGACAAACATATCCTTTCAAGACAGAAAGAGACAGGA

GACATGAGTCTTTGCCGGAGGAAAAGCAGCTCAAGAACACATGTGCAGTC

ACTGGTGTCACCCTGGATAGGCAAGGGATAACTCTTCTAACACAAAATAA

GTGTTTTATGTTTGGAATAAAGTCAACCTTGTTTCTACTGTTTTATACAC

TTTCAAAAAAAAAAAAAAAAAAAAAAAAAAA

TABLE 1

| | | | MMP1 Sense Strand Oligonucleotides | | |
|---|---|---|---|---|---|
| Oligo Number | Start Site | SEQ ID NO: | Sense sequence | Sense Chemistry | Sense Backbone |
| MMP1-1 | 481 | 2 | CCUACAGGAUUGA | mmm0m00m0mmmm-Chl | oooooooooosso |
| MMP1-2 | 483 | 3 | UACAGGAUUGAAA | mmm00m0m00mm-Chl | oooooooooosso |
| MMP1-3 | 486 | 4 | AGGAUUGAAAAUA | mm00mm00m00mm-Chl | oooooooooosso |
| MMP1-4 | 491 | 5 | UGAAAAUUACACA | m00m00mm0m0mm-Chl | oooooooooosso |
| MMP1-5 | 738 | 6 | GAAAGGUGGACCA | mm0m00m000mmm-Chl | oooooooooosso |
| MMP1-6 | 739 | 7 | AAAGGUGGACCAA | mm000m000mmmm-Chl | oooooooooosso |
| MMP1-7 | 869 | 8 | UGAUGUUCAGCUA | mm0m0mmm00mm-Chl | oooooooooosso |
| MMP1-8 | 984 | 9 | ACCUUUGAUGCUA | mmmmmm00m0mmm-Chl | oooooooooosso |
| MMP1-9 | 987 | 10 | UUUGAUGCUAUAA | mmm00m0mm0mm-Chl | oooooooooosso |
| MMP1-10 | 988 | 11 | UUGAUGCUAUAAA | mm00m0mm0mm-Chl | oooooooooosso |
| MMP1-11 | 989 | 12 | UGAUGCUAUAACA | mm0m0mmm0m00m-Chl | oooooooooosso |
| MMP1-12 | 1042 | 13 | ACAUGCGCACAAA | mm0m0m0m0m-Chl | oooooooooosso |
| MMP1-13 | 1044 | 14 | AUGCGCACAAAUA | mm0m0m0m000mm-Chl | oooooooooosso |
| MMP1-14 | 1150 | 15 | AUGAAGUCCGGUA | mm00mmm00mm-Chl | oooooooooosso |
| MMP1-15 | 1151 | 16 | UGAAGUCCGGUUA | mm000mmm00mm-Chl | oooooooooosso |
| MMP1-19 | 1155 | 17 | GUCCGGUUUUUCA | mmmm00mmmmmmm-Chl | oooooooooosso |

TABLE 1-continued

MMP1 Sense Strand Oligonucleotides

| Oligo Number | Start Site | SEQ ID NO: | Sense sequence | Sense Chemistry | Sense Backbone |
|---|---|---|---|---|---|
| MMP1-20 | 1156 | 18 | UCCGGUUUUUCAA | mmm00mmmmmmm-Chl | ooooooooooosso |
| MMP1-16 | 1157 | 19 | CCGGUUUUUCAAA | mm00mmmmmmOmm-Chl | ooooooooooosso |
| MMP1-17 | 1158 | 20 | CGGUUUUUCAAAA | mm0mmmmmm00mm-Chl | ooooooooooosso |
| MMP1-18 | 1159 | 21 | GGUUUUUCAAAGA | mmmmmmmm000mm-Chl | ooooooooooosso |
| MMP1-21 | 1330 | 22 | GGAGGUAUGAUGA | mm000m0m00mmm-Chl | ooooooooooosso |
| MMP1-22 | 1331 | 23 | GAGGUAUGAUGAA | mm0m0m00m0mm-Chl | ooooooooooosso |
| MMP1-23 | 1332 | 24 | AGGUAUGAUGAAA | mm0m0m00m00mm-Chl | ooooooooooosso |
| MMP1-24 | 1334 | 25 | GUAUGAUGAAUAA | mm0m00m000mm-Chl | ooooooooooosso |
| MMP1-25 | 1336 | 26 | AUGAUGAAUAUAA | mm00m000m0mm-Chl | ooooooooooosso |
| MMP1-26 | 1339 | 27 | AUGAAUAUAAACA | mm000m0m000mm-Chl | Ooooooooooosso |
| MMP1-27 | 1359 | 28 | GAUCCAGGUUAUA | mmmmm000mm-Chl | ooooooooooosso |
| MMP1-28 | 1360 | 29 | AUCCAGGUUAUCA | mmmm000mm-Chl | ooooooooooosso |
| MMP1-40 | 1372 | 30 | CCAAAAUGAUAGA | mm00m0m00m0mm-Chl | ooooooooooosso |
| MMP1-29 | 1373 | 31 | CAAAAUGAUAGCA | mm000m0m00mm-Chl | ooooooooooosso |
| MMP1-30 | 1374 | 32 | AAAAUGAUAGCAA | mm00m00m00mm-Chl | ooooooooooosso |
| MMP1-31 | 1393 | 33 | UUCCUGGAAUUGA | mmmmm00m0mmmm-Chl | ooooooooooosso |
| MMP1-32 | 1517 | 34 | UAAUAGCUGGUUA | mm0m00mm00mm-Chl | ooooooooooosso |
| MMP1-33 | 1518 | 35 | AAUAGCUGGUUCA | mmm00mm00mmmm-Chl | ooooooooooosso |
| MMP1-34 | 1519 | 36 | AUAGCUGGUUCAA | mm00mm00mmmmm-Chl | ooooooooooosso |
| MMP1-35 | 1520 | 37 | UAGCUGGUUCAAA | mm0mm00mm0mm-Chl | ooooooooooosso |
| MMP1-36 | 1521 | 38 | AGCUGGUUCAACA | mmmm00mmm00mm-Chl | ooooooooooosso |
| MMP1-37 | 1522 | 39 | GCUGGUUCAACUA | mmm00mmm00mm-Chl | ooooooooooosso |
| MMP1-38 | 1523 | 40 | CUGGUUCAACUGA | mm00mmm00mmmm-Chl | ooooooooooosso |
| MMP1-39 | 1524 | 41 | UGGUUCAACUGCA | mm0mmm00mm0mm-chl | ooooooooooosso |
| MMP1-41 | 1525 | 42 | GGUUCAACUGCAA | mmmmm00mm0mmm-Chl | ooooooooooosso | o: phosphodiester;
s: phosphorothioate;
P: 5' phosphorylation;
O: 2'-OH;
f: 2'-fluoro;
m: 2' O-methyl;
Chl: cholesterol.

TABLE 2

MMP1 Antisense Strand Oligonucleotides

| Oligo Number | SEQ ID NO: | Antisense sequence | AntiSense Chemistry | AntiSense Backbone |
|---|---|---|---|---|
| MMP1-1 | 43 | UCAAUCCUGUAGGUCAGAU | Pmf00ffff0f000ff00m0 | ooooooooooooosssssso |
| MMP1-2 | 44 | UUUCAAUCCUGUAGGUCAG | Pmfff00ffff0f000ff00 | ooooooooooooosssssso |

TABLE 2-continued

MMP1 Antisense Strand Oligonucleotides

| Oligo Number | SEQ ID NO: | Antisense sequence | AntiSense Chemistry | AntiSense Backbone |
|---|---|---|---|---|
| MMP1-3 | 45 | UAUUUUCAAUCCUGUAGGU | Pm0fffff00ffff0f00m0 | ooooooooooooosssssso |
| MMP1-4 | 46 | UGUGUAAUUUUCAAUCCUG | Pm0f0f00fffff00ffff0 | ooooooooooooosssssso |
| MMP1-5 | 47 | UGGUCCACCUUUCAUCUUC | Pm00fff0ffffff0ffff0 | ooooooooooooosssssso |
| MMP1-6 | 48 | UUGGUCCACCUUUCAUCUU | Pmf00fff0fffffff0fff0 | ooooooooooooosssssso |
| MMP1-7 | 49 | UAGCUGAACAUCACCACUG | Pm00ff000f0ff0ff0ff0 | ooooooooooooosssssso |
| MMP1-8 | 50 | UAGCAUCAAAGGUUAGCUU | Pm00f0ff00m00ff00ff0 | ooooooooooooosssssso |
| MMP1-9 | 51 | UUAUAGCAUCAAAGGUUAG | Pmf0f00f0ff00m00ff00 | ooooooooooooosssssso |
| MMP1-10 | 52 | UUUAUAGCAUCAAAGGUUA | Pmff0f00f0ff00m00ff0 | ooooooooooooosssssso |
| MMP1-11 | 53 | UGUUAUAGCAUCAAAGGUU | Pm0ff0f00f0ff00m00f0 | ooooooooooooosssssso |
| MMP1-12 | 54 | UUUGUGCGCAUGUAGAAUC | Pmff0f0f0f0f0f00m0f0 | ooooooooooooosssssso |
| MMP1-13 | 55 | UAUUUGUGCGCAUGUAGAA | Pm0fff0f0f0f0f0f00m0 | ooooooooooooosssssso |
| MMP1-14 | 56 | UACCGGACUUCAUCUCUGU | Pm0ff000ffff0fffff00 | ooooooooooooosssssso |
| MMP1-15 | 57 | UAACCGGACUUCAUCUCUG | Pm00ff000ffff0ffffff0 | ooooooooooooosssssso |
| MMP1-19 | 58 | UGAAAAACCGGACUUCAUC | Pm000m00ff000ffff0f0 | ooooooooooooosssssso |
| MMP1-20 | 59 | UUGAAAAACCGGACUUCAU | Pmf000m00ff000ffff00 | ooooooooooooosssssso |
| MMP1-16 | 60 | UUUGAAAAACCGGACUUCA | Pmff000m00ff000ffff0 | ooooooooooooosssssso |
| MMP1-17 | 61 | UUUUGAAAAACCGGACUUC | Pmfff000m00ff000fff0 | ooooooooooooosssssso |
| MMP1-18 | 62 | UCUUUGAAAAACCGGACUU | Pmffff000m00ff000ff0 | ooooooooooooosssssso |
| MMP1-21 | 63 | UCAUCAUACCUCCAGUAUU | Pmf0ff0f0fffff00f0f0 | ooooooooooooosssssso |
| MMP1-22 | 64 | UUCAUCAUACCUCCAGUAU | Pmff0ff0f0fffff00f00 | ooooooooooooosssssso |
| MMP1-23 | 65 | UUUCAUCAUACCUCCAGUA | Pmfff0ff0f0fffff00f0 | ooooooooooooosssssso |
| MMP1-24 | 66 | UUAUUCAUCAUACCUCCAG | Pmf0fff0ff0f0fffff00 | ooooooooooooosssssso |
| MMP1-25 | 67 | UUAUAUUCAUCAUACCUCC | Pmf0f0fff0ff0f0ffff0 | ooooooooooooosssssso |
| MMP1-26 | 68 | UGUUUAUAUUCAUCAUACC | Pm0fff0f0fff0ff0f0f0 | ooooooooooooosssssso |
| MMP1-27 | 69 | UAUAACCUGGAUCCAUAGA | Pm0f00fff000fff0f000 | ooooooooooooosssssso |
| MMP1-28 | 70 | UGAUAACCUGGAUCCAUAG | Pm00f00fff000fff0f00 | ooooooooooooosssssso |
| MMP1-40 | 71 | UCUAUCAUUUUGGGAUAAC | Pmf0ff0ffff0000f000 | ooooooooooooosssssso |
| MMP1-29 | 72 | UGCUAUCAUUUUGGGAUAA | Pm0ff0ff0ffff00m0f00 | ooooooooooooosssssso |
| MMP1-30 | 73 | UUGCUAUCAUUUUGGGAUA | Pmf0ff0ff0ffff00m0f0 | ooooooooooooosssssso |
| MMP1-31 | 74 | UCAAUUCCAGGAAAGUCAU | Pm00ffff000m000ff00 | ooooooooooooosssssso |
| MMP1-32 | 75 | UAACCAGCUAUUAGCUUUC | Pm00ff00ff0ff00ffff0 | ooooooooooooosssssso |
| MMP1-33 | 76 | UGAACCAGCUAUUAGCUUU | Pm000ff00ff0ff00fff0 | ooooooooooooosssssso |
| MMP1-34 | 77 | UUGAACCAGCUAUUAGCUU | Pmf000ff00ff0ff00ff0 | ooooooooooooosssssso |
| MMP1-35 | 78 | UUUGAACCAGCUAUUAGCU | Pmff000ff00ff0ff00f0 | ooooooooooooosssssso |
| MMP1-36 | 79 | UGUUGAACCAGCUAUUAGC | Pm0ff000ff00ff0ff000 | ooooooooooooosssssso |
| MMP1-37 | 80 | UAGUUGAACCAGCUAUUAG | Pm00ff000ff00ff0ff00 | ooooooooooooosssssso |
| MMP1-38 | 81 | UCAGUUGAACCAGCUAUUA | Pm00ff000ff00ff0ff0 | ooooooooooooosssssso |

TABLE 2-continued

MMP1 Antisense Strand Oligonucleotides

| Oligo Number | SEQ ID NO: | Antisense sequence | AntiSense Chemistry | AntiSense Backbone |
|---|---|---|---|---|
| MMP1-39 | 82 | UGCAGUUGAACCAGCUAUU | PmOfOOffOOOffOOffOfO | ooooooooooooosssssso |
| MMP1-41 | 83 | UUGCAGUUGAACCAGCUAU | PmfOfOOffOOOffOOffOO | ooooooooooooosssssso | o: phosphodiester;
s: phosphorothioate;
P: 5' phosphorylation;
O: 2'-OH;
f: 2'-fluoro;
m: 2' O-methyl.

Example 2

Dose Response Analysis of MMP1 Targeting sd-rxRNAs in HT-1080 Cells

Figures 2A, 2B:
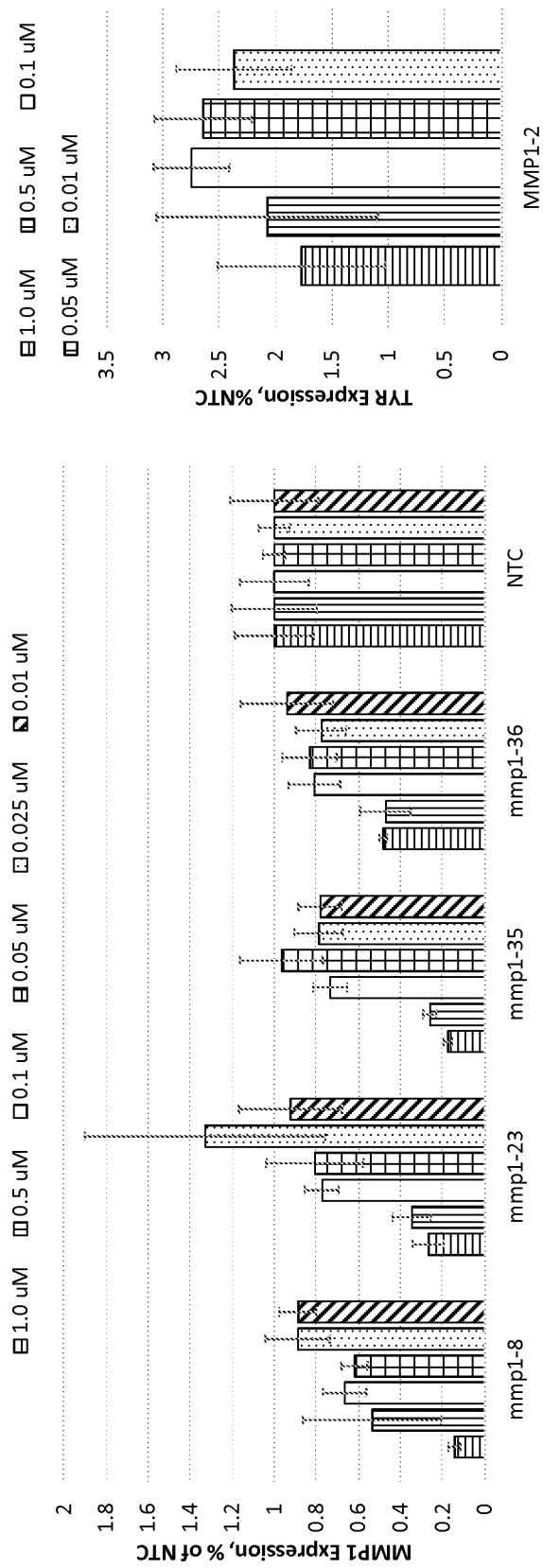
FIGS. 2A-2B show MMP1-targeting sd-rxRNA dose response in HT-1080 cells. Treatment with concentrations ranging from 0.01 µM-1.0 µM are shown.

MMP1-targeting sd-rxRNAs were tested in an in vitro dose response study. The sd-rxRNAs were tested for activity in HT-1080 cells (human fibrosarcoma cell line, 10,000 cells/well, 96 well plate). HT-1080 cells were treated with varying concentrations of MMP1-targeting sd-rxRNAs or non-targeting control (NTC) in serum-free media. Concentrations tested were 1, 0.5, 0.1, 0.05, 0.025 and 0.01 µM. The non-targeting control sd-rxRNA (NTC) is of similar structure to the MMP1-targeting sd-rxRNA and contains similar stabilizing modifications throughout both strands. Forty-eight hours post administration, cells were lysed and mRNA levels determined by the Quantigene branched DNA assay according to the manufacture's protocol using gene-specific probes (Affymetrix). FIGS. 2A-2B demonstrate dose response analysis of lead MMP1-targeting sd-rxRNAs in vitro in HT-1080 cells. Data were normalized to a house keeping gene (PPIB) and graphed with respect to the non-targeting control. Error bars represent the standard deviation from the mean of biological triplicates.

Example 3

Figure 3:
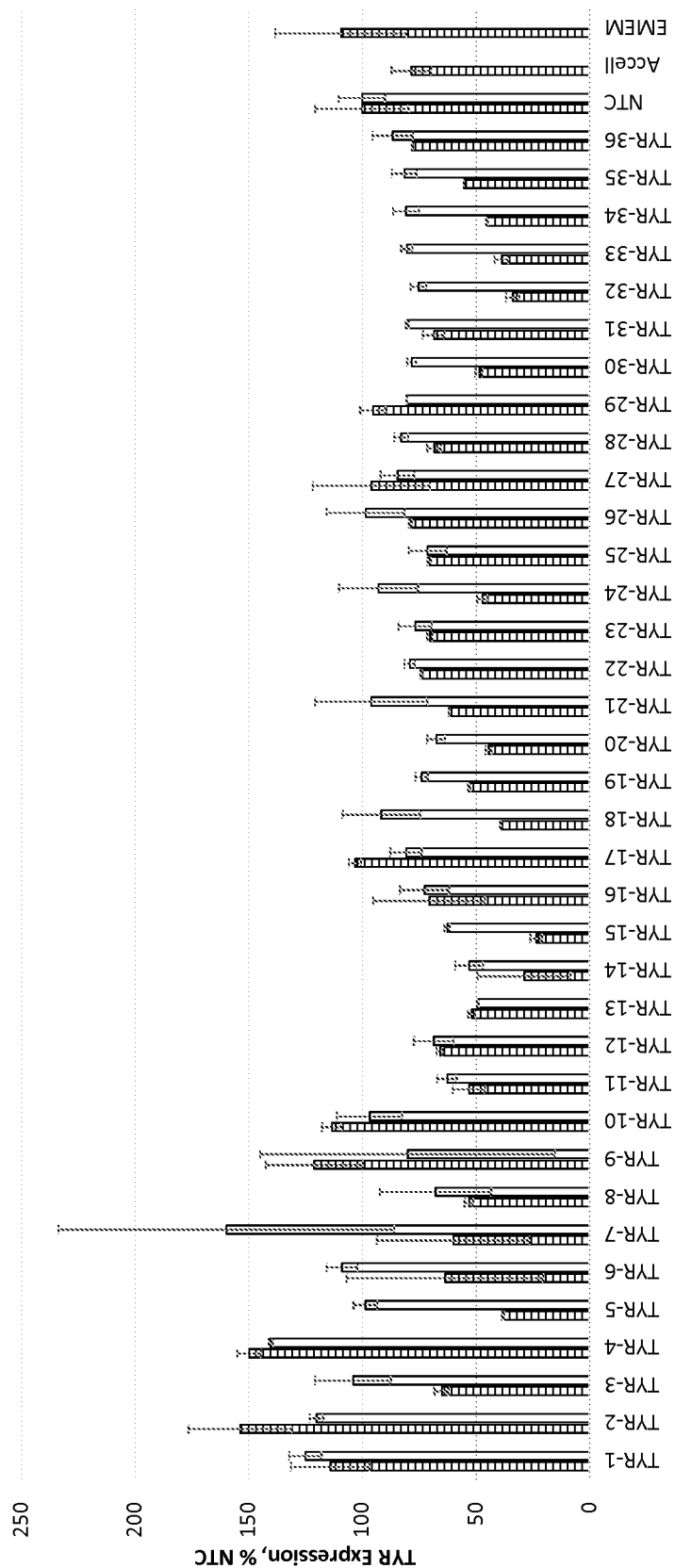
FIG. 3 shows identification of TYR-targeting sd-rxRNAs. TYR-targeting sd-rxRNAs within Tables 3 and 4 significantly reduce target gene mRNA levels in vitro in SK-MEL-5 cells.

Identification of TYR-Targeting sd-rxRNAs sd-rxRNAs targeting TYR were designed, synthesized and screened in vitro to determine the ability of the sd-rxRNAs to reduce target gene mRNA levels. The sd-rxRNAs were tested for activity in SK-MEL-5 cells (human melanoma cell line, 10,000 cells/well, 96 well plate). SK-MEL-5 cells were treated with varying concentrations of a panel of TYR-targeting sd-rxRNAs or non-targeting control (NTC) in serum-free media. Concentrations tested were 1 and 0.1 µM. The non-targeting control sd-rxRNA (NTC) is of similar structure to the TYR-targeting sd-rxRNA and contains similar stabilizing modifications throughout both strands. Forty-eight hours post administration, cells were lysed and mRNA levels determined by the qPCR according to the manufacture's protocol using gene-specific TaqMan probes (Applied Biosystems). FIG. 3 demonstrates that TYR-targeting sd-rxRNAs, found in Tables 3 and 4, significantly reduce target gene mRNA levels in vitro in SK-MEL-5 cells. Data were normalized to a house keeping gene (PPIB) and graphed with respect to the non-targeting control. Error bars represent the standard deviation from the mean of biological duplicates.

The human TYR sequence is represented by GenBank accession number NM_000372.4 listed below:

(SEQ ID NO: 84)
ATCACTGTAGTAGTAGCTGGAAAGAGAAATCTGTGACTCCAATTAGCCAG

TTCCTGCAGACCTTGTGAGGACTAGAGGAAGAATGCTCCTGGCTGTTTTG

TACTGCCTGCTGTGGAGTTTCCAGACCTCCGCTGGCCATTTCCCTAGAGC

CTGTGTCTCCTCTAAGAACCTGATGGAGAAGGAATGCTGTCCACCGTGGA

GCGGGGACAGGAGTCCCTGTGGCCAGCTTTCAGGCAGAGGTTCCTGTCAG

AATATCCTTCTGTCCAATGCACCACTTGGGCCTCAATTTCCCTTCACAGG

GGTGGATGACCGGGAGTCGTGGCCTTCCGTCTTTTATAATAGGACCTGCC

AGTGCTCTGGCAACTTCATGGGATTCAACTGTGGAAACTGCAAGTTTGGC

TTTTGGGGACCAAACTGCACAGAGAGACGACTCTTGGTGAGAAGAAACAT

CTTCGATTTGAGTGCCCCAGAGAAGGACAAATTTTTTGCCTACCTCACTT

TAGCAAAGCATACCATCAGCTCAGACTATGTCATCCCCATAGGGACCTAT

GGCCAAATGAAAAATGGATCAACACCCATGTTTAACGACATCAATATTTA

TGACCTCTTTGTCTGGATGCATTATTATGTGTCAATGGATGCACTGCTTG

GGGGATCTGAAATCTGGAGAGACATTGATTTTGCCCATGAAGCACCAGCT

TTTCTGCCTTGGCATAGACTCTTCTTGTTGCGGTGGGAACAAGAAATCCA

GAAGCTGACAGGAGATGAAAACTTCACTATTCCATATTGGGACTGGCGGG

ATGCAGAAAAGTGTGACATTTGCACAGATGAGTACATGGGAGGTCAGCAC

CCCACAAATCCTAACTTACTCAGCCCAGCATCATTCTTCTCCTCTTGGCA

GATTGTCTGTAGCCGATTGGAGGAGTACAACAGCCATCAGTCTTTATGCA

ATGGAACGCCCGAGGGACCTTTACGGCGTAATCCTGGAAACCATGACAAA

TCCAGAACCCCAAGGCTCCCCTCTTCAGCTGATGTAGAATTTTGCCTGAG

TTTGACCCAATATGAATCTGGTTCCATGGATAAAGCTGCCAATTTCAGCT

TTAGAAATACACTGGAAGGATTTGCTAGTCCACTTACTGGGATAGCGGAT

GCCTCTCAAAGCAGCATGCACAATGCCTTGCACATCTATATGAATGGAAC

AATGTCCCAGGTACAGGGATCTGCCAACGATCCTATCTTCCTTCTTCACC

ATGCATTTGTTGACAGTATTTTTGAGCAGTGGCTCCGAAGGCACCGTCCT

CTTCAAGAAGTTTATCCAGAAGCCAATGCACCCATTGGACATAACCGGGA

ATCCTACATGGTTCCTTTTATACCACTGTACAGAAATGGTGATTTCTTTA

```
TTTCATCCAAAGATCTGGGCTATGACTATAGCTATCTACAAGATTCAGAC
CCAGACTCTTTTCAAGACTACATTAAGTCCTATTTGGAACAAGCGAGTCG
GATCTGGTCATGGCTCCTTGGGCGGCGATGGTAGGGGCCGTCCTCACTG
CCCTGCTGGCAGGGCTTGTGAGCTTGCGTGTCGTCACAAGAGAAAGCAG
CTTCCTGAAGAAAGCAGCCACTCCTCATGGAGAAAGAGGATTACCACAG
CTTGTATCAGAGCCATTTATAAAAGGCTTAGGCAATAGAGTAGGGCCAAA
AAGCCTGACCTCACTCTAACTCAAAGTAATGTCCAGGTTCCCAGAGAATA
TCTGCTGGTATTTTTCTGTAAAGACCATTTGCAAAATTGTAACCTAATAC
AAAGTGTAGCCTTCTTCCAACTCAGGTAGAACACACCTGTCTTTGTCTTG
CTGTTTTCACTCAGCCCTTTTAACATTTTCCCCTAAGCCCATATGTCTAA
GGAAAGGATGCTATTTGGTAATGAGGAACTGTTATTTGTATGTGAATTAA
AGTGCTCTTATTTTAAAAAATTGAAATAATTTTGATTTTTGCCTTCTGAT
TATTTAAAGATCTATATATGTTTTATTGGCCCCTTCTTTATTTTAATAAA
ACAGTGAGAAATCTAAAAAAAAAAAAAAAAA
```

TABLE 3

TYR Sense Strand Oligonucleotides

| Oligo Number | Start Site | SEQ ID NO: | Sense sequence | Sense Chemistry | Sense Backbone |
|---|---|---|---|---|---|
| TYR-1 | 329 | 85 | UAUAAUAGGACCA | mmm0 0m0 0m0mmm-Chl | ooooooooooosso |
| TYR-2 | 330 | 86 | AUAAUAGGACCUA | mm00m00m0mmmm-Chl | ooooooooooosso |
| TYR-3 | 331 | 87 | UAAUAGGACCUGA | mm0m00m0mmmmm-Chl | ooooooooooosso |
| TYR-4 | 489 | 88 | UCACUUUAGCAAA | mm0mmmm00m0mm-Chl | ooooooooooosso |
| TYR-5 | 490 | 89 | CACUUUAGCAAAA | mmmmmm00m00mm-Chl | ooooooooooosso |
| TYR-6 | 544 | 90 | UGGCCAAAUGAAA | mm0m000m00mm-Chl | ooooooooooosso |
| TYR-7 | 662 | 91 | AGAGACAUUGAUA | mm000m0mm00mm-Chl | ooooooooooosso |
| TYR-8 | 663 | 92 | GAGACAUUGAUUA | mm00m0mmm00mm-Chl | ooooooooooosso |
| TYR-9 | 698 | 93 | CUGCCUUGGCAUA | mm0mmmm00m0mm-Chl | ooooooooooosso |
| TYR-10 | 809 | 94 | GACAUUUGCACAA | mmm0mmm0m0mm-Chl | ooooooooooosso |
| TYR-11 | 811 | 95 | CAUUUGCACAGAA | mmmmm0m0m00mm-Chl | ooooooooooosso |
| TYR-12 | 812 | 96 | AUUUGCACAGAUA | mmmm0m0m000mm-Chl | ooooooooooosso |
| TYR-13 | 813 | 97 | UUUGCACAGAUGA | mm0m0m0m000mm-Chl | ooooooooooosso |
| TYR-14 | 815 | 98 | UGCACAGAUGAGA | mmm0m000m00mm-Chl | ooooooooooosso |
| TYR-15 | 816 | 99 | GCACAGAUGAGUA | mm0m000m000mm-Chl | ooooooooooosso |
| TYR-16 | 817 | 100 | CACAGAUGAGUAA | mmm000m000mm-Chl | ooooooooooosso |
| TYR-37 | 818 | 101 | ACAGAUGAGUACA | mm000m000m0mm-Chl | ooooooooooosso |
| TYR-17 | 853 | 102 | UCCUAACUUACUA | mmmm00mmm0mm-Chl | ooooooooooosso |
| TYR-18 | 854 | 103 | CCUAACUUACUCA | mmm00mmm0mmmm-Chl | ooooooooooosso |
| TYR-38 | 855 | 104 | CUAACUUACUCAA | mm00mmm0mmmmm-Chl | ooooooooooosso |
| TYR-20 | 881 | 105 | UUCUCCUCUUGGA | mmmmmmmmmm0mm-Chl | ooooooooooosso |
| TYR-21 | 978 | 106 | CUGGAAACCAUGA | mm000m0mm0mm-Chl | ooooooooooosso |
| TYR-22 | 979 | 107 | UGGAAACCAUGAA | mm0m00m0mm0mm-Chl | ooooooooooosso |
| TYR-23 | 980 | 108 | GGAAACCAUGACA | mm000m0m00mm-Chl | ooooooooooosso |
| TYR-24 | 981 | 109 | GAAACCAUGACAA | mm00mm0m0 0mm-Chl | ooooooooooosso |
| TYR-25 | 982 | 110 | AAACCAUGACAAA | mm0mm0m0m0mm-Chl | ooooooooooosso |
| TYR-26 | 983 | 111 | AACCAUGACAAAA | mmmm0m00m00mm-Chl | ooooooooooosso |
| TYR-27 | 1083 | 112 | CCAUUUCAGCUA | mm0mmmm00mmm-Chl | ooooooooooosso |

TABLE 3-continued

TYR Sense Strand Oligonucleotides

| Oligo Number | Start Site | SEQ ID NO: | Sense sequence | Sense Chemistry | Sense Backbone |
|---|---|---|---|---|---|
| TYR-28 | 1094 | 113 | UUUAGAAAUACAA | mmm00m00m0mmm-Chl | ooooooooooosso |
| TYR-29 | 1101 | 114 | AUACACUGGAAGA | mm0m0mm00m0mm-Chl | ooooooooooosso |
| TYR-30 | 1103 | 115 | ACACUGGAAGGAA | mm0mm000m00mm-Chl | ooooooooooosso |
| TYR-31 | 1108 | 116 | GGAAGGAUUUGCA | mm00m00mmmm-Chl | ooooooooooosso |
| TYR-32 | 1111 | 117 | AGGAUUUGCUAGA | mm00mmm0m0mm-Chl | ooooooooooosso |
| TYR-39 | 1113 | 118 | GAUUUGCUAGUCA | mmmmm0mm00mmm-Chl | ooooooooooosso |
| TYR-33 | 1186 | 119 | GAAUGGAACAAUA | mm0m00m0m00mm-Chl | ooooooooooosso |
| TYR-34 | 1189 | 120 | UGGAACAAUGUCA | mm000m00mm-Chl | ooooooooooosso |
| TYR-35 | 1310 | 121 | CCAGAAGCCAAUA | mm0m000mm00mm-Chl | ooooooooooosso |
| TYR-36 | 1311 | 122 | CAGAAGCCAAUGA | mm00mm00mm-Chl | ooooooooooosso |
| TYR-19 | 1312 | 123 | AGAAGCCAAUGCA | mm000mm00m0mm-Chl | ooooooooooosso |
| TYR-40 | 1652 | 124 | CAGAGCCAUUUAA | mm000mm0mmmmm-Chl | ooooooooooosso |
| TYR-41 | 1653 | 125 | AGAGCCAUUUAUA | mm00mm0mmm0mm-Chl | ooooooooooosso | o: phosphodiester;
s: phosphorothioate;
P: 5' phosphorylation;
0: 2'-OH;
f: 2'-fluoro;
m: 2' O-methyl;
Chl: cholesterol.

TABLE 4

TYR Antisense Strand Oligonucleotides

| Oligo Number | SEQ ID NO: | Antisense sequence | AntiSense Chemistry | AntiSense Backbone |
|---|---|---|---|---|
| TYR-1 | 126 | UGGUCCUAUUAUAAAGAC | Pm00ffff0ff0f000m000 | Oooooooooooossssssso |
| TYR-2 | 127 | UAGGUCCUAUUAUAAAGA | Pm000ffff0ff0f00m0m0 | Oooooooooooossssssso |
| TYR-3 | 128 | UCAGGUCCUAUUAUAAAG | Pmf000ffff0ff0f00m00 | Oooooooooooossssssso |
| TYR-4 | 129 | UUUGCUAAAGUGAGGUAGG | Pmff0ff0m00f00m0f000 | Oooooooooooossssssso |
| TYR-5 | 130 | UUUUGCUAAAGUGAGGUAG | Pmfff0ff0m00f00m0f00 | ooooooooooossssssso |
| TYR-6 | 131 | UUUCAUUUGGCCAUAGGUC | Pmfff0fff00ff0f000f0 | ooooooooooossssssso |
| TYR-7 | 132 | UAUCAAUGUCUCUCCAGAU | Pm0ff00f0fffffff00m0 | ooooooooooossssssso |
| TYR-8 | 133 | UAAUCAAUGUCUCUCCAGA | Pm00ff00f0fffffff000 | ooooooooooossssssso |
| TYR-9 | 134 | UAUGCCAAGGCAGAAAAGC | Pm0f0ff0m00f00m0m00 | ooooooooooossssssso |
| TYR-10 | 135 | UUGUGCAAAUGUCACACUU | Pmf0f0f000f0ff0f0ff0 | ooooooooooossssssso |

TABLE 4-continued

TYR Antisense Strand Oligonucleotides

| Oligo Number | SEQ ID NO: | Antisense sequence | AntiSense Chemistry | AntiSense Backbone |
|---|---|---|---|---|
| TYR-11 | 136 | UUCUGUGCAAAUGUCACAC | PmfffOfOf000fOffOf00 | ooooooooooosssssso |
| TYR-12 | 137 | UAUCUGUGCAAAUGUCACA | Pm0fffOfOf000fOffOf0 | ooooooooooosssssso |
| TYR-13 | 138 | UCAUCUGUGCAAAUGUCAC | PmOfffOfOf000fOffO00 | ooooooooooosssssso |
| TYR-14 | 139 | UCUCAUCUGUGCAAAUGUC | PmfffOfffOfOf000fOf0 | ooooooooooosssssso |
| TYR-15 | 140 | UACUCAUCUGUGCAAAUGU | PmOfffOfffOfOf000f00 | ooooooooooosssssso |
| TYR-16 | 141 | UUACUCAUCUGUGCAAAUG | PmOfffOfffOfOf000f0 | ooooooooooosssssso |
| TYR-37 | 142 | UGUACUCAUCUGUGCAAAU | Pm0fOfffOfffOfOf00m0 | ooooooooooosssssso |
| TYR-17 | 143 | UAGUAAGUUAGGAUUUGUG | Pm00f000ff000mfffOf0 | ooooooooooosssssso |
| TYR-18 | 144 | UGAGUAAGUUAGGAUUUGU | Pm000f000ff00mOfff00 | Ooooooooooosssssso |
| TYR-38 | 145 | UUGAGUAAGUUAGGAUUUG | Pmf000f000ff00mOfffO | Ooooooooooosssssso |
| TYR-20 | 146 | UCCAAGAGGAGAAGAAUGA | Pmff00m00m000m000f00 | Ooooooooooosssssso |
| TYR-21 | 147 | UCAUGGUUUCCAGGAUUAC | PmfOf00fffff00mOff00 | Ooooooooooosssssso |
| TYR-22 | 148 | UUCAUGGUUUCCAGGAUUA | PmffOf00fffff0m00ff0 | Ooooooooooosssssso |
| TYR-23 | 149 | UGUCAUGGUUUCCAGGAUU | PmOffOf00fffff00mOf0 | Ooooooooooosssssso |
| TYR-24 | 150 | UUGUCAUGGUUUCCAGGAU | PmfOffOf00fffff000m0 | Ooooooooooosssssso |
| TYR-25 | 151 | UUUGUCAUGGUUUCCAGGA | PmffOffOf00fffff00m0 | Ooooooooooosssssso |
| TYR-26 | 152 | UUUUGUCAUGGUUUCCAGG | PmfffOffOf00fffff000 | Ooooooooooosssssso |
| TYR-27 | 153 | UAGCUGAAAUUGGCAGCUU | Pm00ffOm00ffOOf00ffO | Ooooooooooosssssso |
| TYR-28 | 154 | UUGUAUUUCUAAAGCUGAA | PmfOfOfffffOOmOff000 | Ooooooooooosssssso |
| TYR-29 | 155 | UCUUCCAGUGUAUUUCUAA | PmffffffOOfOfOfffffOO | Ooooooooooosssssso |
| TYR-30 | 156 | UUCCUUCCAGUGUAUUUCU | PmfffffffOOfOfOffffO | Ooooooooooosssssso |
| TYR-31 | 157 | UGCAAAUCCUUCCAGUGUA | PmOf000fffffffOOfOfO | Ooooooooooosssssso |
| TYR-32 | 158 | UCUAGCAAAUCCUUCCAGU | Pmff00f000fffffff000 | Ooooooooooosssssso |
| TYR-39 | 159 | UGACUAGCAAAUCCUUCCA | Pm00ff00f000fffffff0 | Ooooooooooosssssso |

TABLE 4-continued

TYR Antisense Strand Oligonucleotides

| Oligo Number | SEQ ID NO: | Antisense sequence | AntiSense Chemistry | AntiSense Backbone |
|---|---|---|---|---|
| TYR-33 | 160 | UAUUGUUCCAUUCAUAUAG | PmOffOffffOfffOfOfOO | OooooooooooossssssO |
| TYR-34 | 161 | UGACAUUGUUCCAUUCAUA | PmOOfOffOffffOfffOfO | OooooooooooossssssO |
| TYR-35 | 162 | UAUUGGCUUCUGGAUAAAC | PmOffOOfffffOOOfOOmO | OooooooooooossssssO |
| TYR-36 | 163 | UCAUUGGCUUCUGGAUAAA | PmfOffOOfffffOOOfOOO | OooooooooooossssssO |
| TYR-19 | 164 | UGCAUUGGCUUCUGGAUAA | PmOfOffOOfffffOOOfOO | OooooooooooossssssO |
| TYR-40 | 165 | UUAAAUGGCUCUGAUACAA | PmfOOOfOOffffOOfOfOO | OooooooooooossssssO |
| TYR-41 | 166 | UAUAAAUGGCUCUGAUACA | PmOfOOOfOOffffOOfOfO | OooooooooooossssssO | o: phosphodiester;
s: phosphorothioate;
P: 5' phosphorylation;
O: 2'-OH;
f: 2'-fluoro;
m: 2' O-methyl.

Example 4

Dose Response Analysis of MMP1 Targeting sd-rxRNAs in SK-MEL-5 Cells

Figure 4:
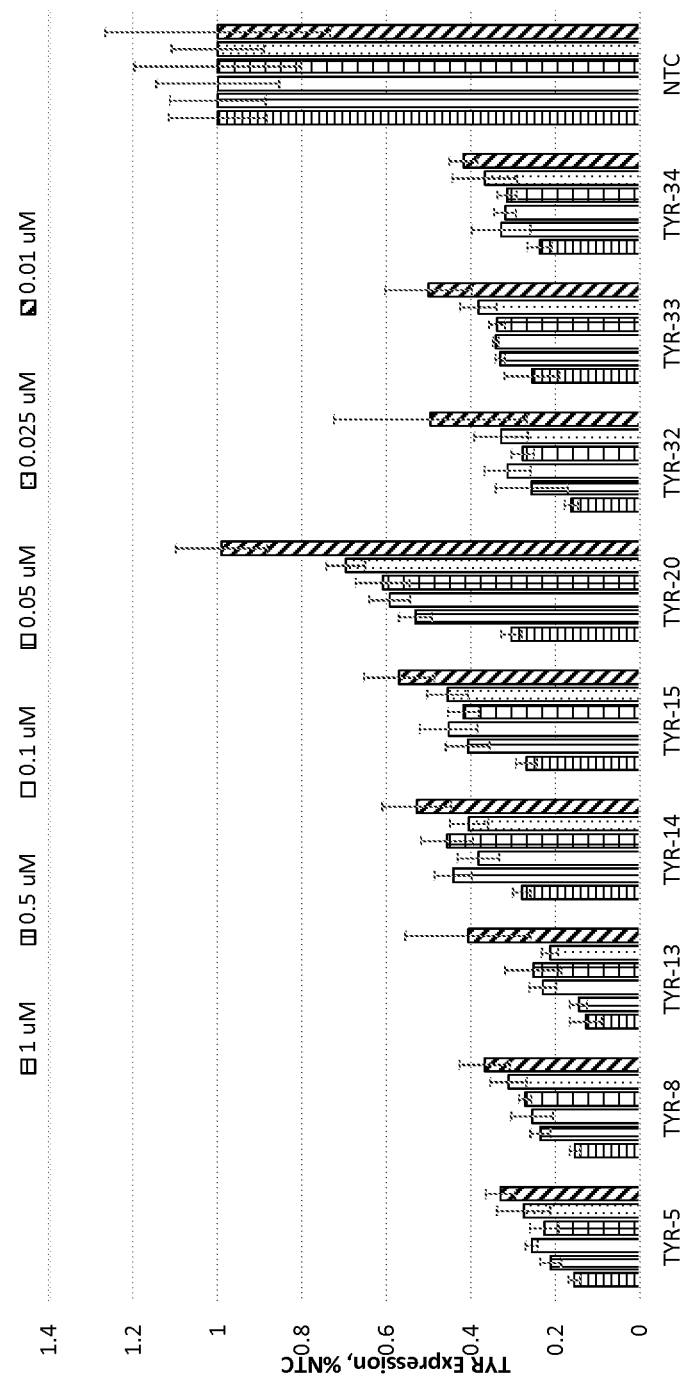
FIG. 4 shows TYR-targeting sd-rxRNA dose response in SK-MEL-5 cells. Treatment with concentrations ranging from 0.01 µM-1.0 µM are shown. For each sample, the order of bars on the graph corresponds to: 1 µM, 0.5 µM, 0.1 µM, 0.05 µM, 0.025 µM and 0.01 µM.

TYR-targeting sd-rxRNAs were tested in an in vitro dose response study. The sd-rxRNAs were tested for activity in SK-MEL-5 cells (human melanoma cell line, 10,000 cells/well, 96 well plate). SK-MEL-5 cells were treated with varying concentrations of a panel of TYR-targeting sd-rxRNAs or non-targeting control (NTC) in serum-free media. Concentrations tested were 1, 0.5, 0.1, 0.05, 0.05 and 0.01 µM. The non-targeting control sd-rxRNA (NTC) is of similar structure to the TYR-targeting sd-rxRNA and contains similar stabilizing modifications throughout both strands. Forty-eight hours post administration, cells were lysed and mRNA levels determined by the qPCR according to the manufacture's protocol using gene-specific TaqMan probes (Applied Biosystems). FIG. 4 demonstrates dose response analysis of lead TYR-targeting sd-rxRNAs in vitro in SK-MEL-5 cells. Data were normalized to a house keeping gene (PPIB) and graphed with respect to the non-targeting control. Error bars represent the standard deviation from the mean of biological triplicates.

Example 5

Dose Response Analysis of Optimized MMP1 and TYR Targeting sd-rxRNAs

Original and Optimized MMP1-targeting sd-rxRNAs (optimized sequences are shown in Tables 5 and 6) were tested in an in vitro dose response study. The sd-rxRNAs were tested for activity in HT-1080 cells (human fibrosarcoma cell line, 10,000 cells/well, 96 well plate). HT-1080 cells were treated with varying concentrations of MMP1-targeting sd-rxRNAs or non-targeting control (#21803) in serum-free media. Concentrations tested were 1, 0.5, 0.1, 0.05, 0.025 and 0.01 µM. The non-targeting control sd-rxRNA (#21803) is of similar structure to the MMP1-targeting sd-rxRNA and contains similar stabilizing modifications throughout both strands. Forty eight hours post administration, cells were lysed and mRNA levels determined by the Quantigene branched DNA assay according to the manufacture's protocol using gene-specific probes (Affymetrix, Santa Clara, Calif.). FIG. 5A demonstrates dose response analysis of lead MMP1-targeting sd-rxRNAs in vitro in HT-1080 cells. Data were normalized to a house keeping gene (TBP) and graphed with respect to the non-targeting control. Error bars represent the standard deviation from the mean of biological triplicates.

Original and Optimized TYR-targeting sd-rxRNAs (optimized sequences are shown in Tables 7 and 8) were tested in an in vitro dose response study. The sd-rxRNAs were tested for activity in SK-MEL-5 cells (human melanoma cell line, 10,000 cells/well, 96 well plate). SK-MEL-5 cells were treated with varying concentrations of a panel of TYR-targeting sd-rxRNAs or non-targeting control (#21803) in serum-free media. Concentrations tested were 1, 0.5, 0.1, 0.05, 0.05 and 0.01 µM. The non-targeting control sd-rxRNA (#21803) is of similar structure to the TYR-targeting sd-rxRNA and contains similar stabilizing modifications throughout both strands. Forty eight hours post administration, cells were lysed and mRNA levels determined by the qPCR according to the manufacturer's protocol using gene-specific TaqMan probes (Applied Biosystems, Carlsbad, Calif.). FIG. 5B demonstrates dose response analysis of lead TYR-targeting sd-rxRNAs in vitro in SK-MEL-5 cells. Data were normalized to a house keeping gene (PPIB) and graphed with respect to the non-targeting control. Error bars represent the standard deviation from the mean of biological triplicates.

TABLE 5

Optimized MMP-1 Sense Strand Oligonucleotides

| Oligo Number | Duplex ID | Oligo Number | Start Site | SEQ ID NO: | Sense sequence | Sense Chemistry | Sense backbone |
|---|---|---|---|---|---|---|---|
| MMP1-42 | 26166 | 25856 | 869 | 167 | UGAUGUUCAGCUA | mm0m0mmm00mmm-Ch1 | Ooooooooooosso |
| MMP1-43 | 26167 | 25856 | | 168 | UGAUGUUCAGCUA | mm0m0mmm00mmm-Ch1 | Ooooooooooosso |
| MMP1-44 | 26168 | 25856 | | 169 | UGAUGUUCAGCUA | mm0m0mmm00mmm-Ch1 | Ooooooooooosso |
| MMP1-45 | 26169 | 25856 | | 170 | UGAUGUUCAGCUA | mm0m0mmm00mmm-Ch1 | Ooooooooooosso |
| MMP1-46 | 26170 | 26102 | | 171 | YGAYGYYXAGXYA | mm0m0mmm00mmm-Ch1 | Ooooooooooosso |
| MMP1-47 | 26171 | 26103 | | 172 | UGAUGUUCAGCUA | mmmmmmmmmmmmm-Ch1 | Ooooooooooosso |
| MMP1-48 | 26172 | 25858 | 984 | 173 | ACCUUUGAUGCUA | mmmmmm00m0mmm-Ch1 | Ooooooooooosso |
| MMP1-49 | 26173 | 25858 | | 174 | ACCUUUGAUGCUA | mmmmmm00m0mmm-Ch1 | Ooooooooooosso |
| MMP1-50 | 26174 | 25858 | | 175 | ACCUUUGAUGCUA | mmmmmm00m0mmm-Ch1 | Ooooooooooosso |
| MMP1-51 | 26175 | 25858 | | 176 | ACCUUUGAUGCUA | mmmmmm00m0mmm-Ch1 | ooooooooooosso |
| MMP1-52 | 26176 | 25858 | | 177 | ACCUUUGAUGCUA | mmmmmm00m0mmm-Ch1 | Ooooooooooosso |
| MMP1-53 | 26177 | 25858 | | 178 | ACCUUUGAUGCUA | mmmmmm00m0mmm-Ch1 | Ooooooooooosso |
| MMP1-54 | 26178 | 26110 | | 179 | AXXYYYGAYGXYA | mmmmmm00m0mmm-Ch1 | Ooooooooooosso |
| MMP1-55 | 26179 | 25888 | 1332 | 180 | AGGUAUGAUGAAA | mm0m0m00m00mmm-Ch1 | Ooooooooooosso |
| MMP1-56 | 26180 | 25888 | | 181 | AGGUAUGAUGAAA | mm0m0m0m00mmm-Ch1 | Ooooooooooosso |
| MMP1-57 | 26181 | 25888 | | 182 | AGGUAUGAUGAAA | mm0m0m0m00mmm-Ch1 | Ooooooooooosso |
| MMP1-58 | 26182 | 25888 | | 183 | AGGUAUGAUGAAA | mm0m0m00m00mmm-Ch1 | Ooooooooooosso |
| MMP1-59 | 26183 | 26115 | | 184 | AGGYAYGAYGAAA | mm0m0m00m00mmm-Ch1 | Ooooooooooosso |
| MMP1-60 | 26184 | 26116 | | 185 | AGGYAYGAYGAAA | mm0m0mm0mmm-Ch1 | Ooooooooooosso |
| MMP1-61 | 26185 | 25914 | 1520 | 186 | UAGCUGGUUCAAA | mm0mm00mmm0mm-Ch1 | Ooooooooooosso |
| MMP1-62 | 26186 | 25914 | | 187 | UAGCUGGUUCAAA | mm0mm00mmm0mm-Ch1 | Ooooooooooosso |
| MMP1-63 | 26187 | 25914 | | 188 | UAGCUGGUUCAAA | mm0mm00mmm0mm-Ch1 | Ooooooooooosso |
| MMP1-64 | 26188 | 25914 | | 189 | UAGCUGGUUCAAA | mm0mm00mmm0mm-Ch1 | Ooooooooooosso |
| MMP1-65 | 26189 | 26121 | | 190 | YAGXYGGYYXAAA | mm0mm00mmm0mm-Ch1 | Ooooooooooosso |
| MMP1-66 | 26190 | 25916 | 1521 | 191 | AGCUGGUUCAACA | mmmm00mmm0mm-Ch1 | Ooooooooooosso |
| MMP1-67 | 26191 | 25916 | 1521 | 192 | AGCUGGUUCAACA | mmmm00mmm00mm-Ch1 | Ooooooooooosso |
| MMP1-68 | 26192 | 25916 | 1521 | 193 | AGCUGGUUCAACA | mmmm0mmm00mm-Ch1 | Ooooooooooosso |

TABLE 5-continued

Optimized MMP-1 Sense Strand Oligonucleotides

| Oligo Number | Duplex ID | Oligo Number | Start Site | SEQ ID NO: | Sense sequence | Sense Chemistry | Sense backbone |
| --- | --- | --- | --- | --- | --- | --- | --- |
| MMP1-69 | 26193 | 25916 | 1521 | 194 | AGCUGGUUCAACA | mmmmOOmmmOOmm-Chl | ooooooooooosso |
| MMP1-70 | 26194 | 26126 | 1521 | 195 | AGXYGGYYXAAXA | mmmmOOmmmOOmm-Chl | Ooooooooooosso | o: phosphodiester;
s: phosphorothioate;
P: 5' phosphorylation;
O: 2'-OH;
f: 2'-fluoro;
m: 2' O-methyl.
X = 5 methyl C
and
Y = 5 methyl U

TABLE 6

Optimized MMP-1 Antisense Strand Oligonucleotides

| Oligo Number | Duplex ID | Start Site | Oligo Number | SEQ ID NO: | Antisense sequence | AntiSense Chemistry | AntiSense Backbone |
| --- | --- | --- | --- | --- | --- | --- | --- |
| MMP1-42 | 26166 | 869 | 26098 | 196 | UAGCUGAACAUCACCACUG | PmOOff000f0ff0fmOfmO | ooooooooooossssssso |
| MMP1-43 | 26167 | | 26099 | 197 | YAGXYGAAXAYXAXXAXYG | PmOOff000f0ff0ffOffO | ooooooooooossssssso |
| MMP1-44 | 26168 | | 26100 | 198 | YAGXYGAAXAYXAXXAXYG | PmOOff000f0ff0fmOmmO | ooooooooooossssssso |
| MMP1-45 | 26169 | | 26101 | 199 | UAGCUGAACAUCACCACUG | PmOOff000f0ff0fmOmmO | ooooooooooossssssso |
| MMP1-46 | 26170 | | 25855 | 200 | UAGCUGAACAUCACCACUG | PmOOff000f0ff0ffOffO | ooooooooooossssssso |
| MMP1-47 | 26171 | | 25855 | 201 | UAGCUGAACAUCACCACUG | PmOOff000f0ff0ffOffO | ooooooooooossssssso |
| MMP1-48 | 26172 | 984 | 26104 | 202 | UAGCAUCAAAGGUUAGCUU | PmOOf0ff00m00mf00mmO | ooooooooooossssssso |
| MMP1-49 | 26173 | | 26105 | 203 | UAGCAUCAAAGGUUAGCUU | PmOOf0ff00m00mfffmmO | ooooooooooossssssso |
| MMP1-50 | 26174 | | 26106 | 204 | UAGCAUCAAAGGUUAGCUU | PmOOf0ff00m00fffffO | ooooooooooossssssso |
| MMP1-51 | 26175 | | 26107 | 205 | YAGXAYXAAAGGYYAGXYU | PmOOf0ff00m00mf00mmO | ooooooooooossssssso |
| MMP1-52 | 26176 | | 26108 | 206 | YAGXAYXAAAGGYUAGXYU | PmOOf0ff00m00mfffmmO | ooooooooooossssssso |
| MMP1-53 | 26177 | | 26109 | 207 | UAGXAYXAAAGGYYAGXYU | PmOOf0ff00m00fffffO | ooooooooooossssssso |
| MMP1-54 | 26178 | | 25857 | 208 | UAGCAUCAAAGGUUAGCUU | PmOOf0ff00m00ff00ffO | ooooooooooossssssso |
| MMP1-55 | 26179 | 1332 | 26111 | 209 | UUUCAUCAUACCUCCAGUA | Pmfff0ff0f0ffmfmffmO | ooooooooooossssssso |
| MMP1-56 | 26180 | | 26112 | 210 | UUUCAUCAUACCUCCAGUA | Pmfff0ff0f0ffmfmOmmO | ooooooooooossssssso |
| MMP1-57 | 26181 | | 26113 | 211 | YYYXAYXAYAXXYXXAGYA | Pmfff0ff0f0ffmfmffmO | ooooooooooossssssso |
| MMP1-58 | 26182 | | 26114 | 212 | YYYXAYXAYAXXYXXAGYA | Pmfff0ff0f0ffmfmOfmO | ooooooooooossssssso |
| MMP1-59 | 26183 | | 25887 | 213 | UUUCAUCAUACCUCCAGUA | Pmfff0ff0f0ffffff0Of0 | ooooooooooossssssso |
| MMP1-60 | 26184 | | 25887 | 214 | UUUCAUCAUACCUCCAGUA | Pmfff0ff0f0ffffff0Of0 | ooooooooooossssssso |
| MMP1-61 | 26185 | 1520 | 26117 | 215 | UUUGAACCAGCUAUUAGCU | Pmff0f0ff00ff0fmOfmO | ooooooooooossssssso |
| MMP1-62 | 26186 | | 26118 | 216 | UUUGAACCAGCUAUUAGCU | Pmff0m0ff00ff0fmOmmO | ooooooooooossssssso |
| MMP1-63 | 26187 | | 26119 | 217 | YYYGAAXXAGXYAYYAGXU | Pmff0f0ff00ff0fmOfmO | ooooooooooossssssso |

TABLE 6-continued

Optimized MMP-1 Antisense Strand Oligonucleotides

| Oligo Number | Duplex ID | Start Site | Oligo Number | SEQ ID NO: | Antisense sequence | AntiSense Chemistry | AntiSense Backbone |
|---|---|---|---|---|---|---|---|
| MMP1-64 | 26188 |  | 26120 | 218 | YYYGAAXXAGXY AYYAGXU | Pmff0m0ff00ff0f m0mm0 | oooooooooo ossssssso |
| MMP1-65 | 26189 |  | 25913 | 219 | UUUGAACCAGCUA UUAGCU | Pmff000ff00ff0ff 00f0 | oooooooooo ossssssso |
| MMP1-66 | 26190 | 1521 | 26122 | 220 | UGUUGAACCAGCU AUUAGC | Pm0ff0f0ff00ff0f fmm0 | oooooooooo ossssssso |
| MMP1-67 | 26191 | 1521 | 26123 | 221 | UGUUGAACCAGCU AUUAGC | Pm0ff0f0ff00ff0 mmmm0 | oooooooooo ossssssso |
| MMP1-68 | 26192 | 1521 | 26124 | 222 | YGYYGAAXXAGX YAYYAGC | Pm0ff0f0ff00ff0f fmm0 | oooooooooo ossssssso |
| MMP1-69 | 26193 | 1521 | 26125 | 223 | YGYYGAAXXAGX YAYYAGC | Pm0ff0f0ff00ff0 mmmm0 | oooooooooo ossssssso |
| MMP1-70 | 26194 | 1521 | 25915 | 224 | UGUUGAACCAGCU AUUAGC | Pm0ff000ff00ff0f f000 | oooooooooo ossssssso | o: phosphodiester;
s: phosphorothioate;
P: 5' phosphorylation;
O: 2'-OH;
f: 2'-fluoro;
m: 2' O-methyl.
X = 5 methyl C
and
Y = 5 methyl U

TABLE 7

Optimized TYR Sense Strand Oligonucleotides

| Oligo Number | RXi Duplex ID | Oligo Number | Start Site | SEQ ID NO: | Sense sequence | Sense Chemsitry | Sense Backbone |
|---|---|---|---|---|---|---|---|
| TYR-42 | 26195 | 25934 | 490 | 225 | CACUUUAGC AAAA | mmmmmm00m00mm-Chl | ooooooooo osso |
| TYR-43 | 26196 | 25934 | 490 | 226 | CACUUUAGC AAAA | mmmmmm00m00mm-Chl | ooooooooo osso |
| TYR-44 | 26197 | 25934 | 490 | 227 | CACUUUAGC AAAA | mmmmmm00m00mm-Chl | ooooooooo osso |
| TYR-45 | 26198 | 25934 | 490 | 228 | CACUUUAGC AAAA | mmmmmm00m00mm-Chl | ooooooooo osso |
| TYR-46 | 26199 | 26131 | 490 | 229 | XAXYYYAGX AAAA | mmmmmm00m00mm-Chl | ooooooooo osso |
| TYR-47 | 26200 | 26132 | 490 | 230 | XAXYYYAGX AAAA | mmmmmm0mmm0mm-Chl | ooooooooo osso |
| TYR-48 | 26201 | 25940 | 663 | 231 | GAGACAUUG AUUA | mm00m0mm00mm-Chl | ooooooooo osso |
| TYR-49 | 26202 | 25940 | 663 | 232 | GAGACAUUG AUUA | mm00m0mm00mm-Chl | ooooooooo osso |
| TYR-50 | 26203 | 25940 | 663 | 233 | GAGACAUUG AUUA | mm00m0mm00mm-Chl | ooooooooo osso |
| TYR-51 | 26204 | 25940 | 663 | 234 | GAGACAUUG AUUA | mm00m0mm00mm-Chl | ooooooooo osso |
| TYR-52 | 26205 | 26137 | 663 | 235 | GAGAXAYYG AYYA | mm00m0mm00mm-Chl | ooooooooo osso |

TABLE 7-continued

Optimized TYR Sense Strand Oligonucleotides

| Oligo Number | RXi Duplex ID | Oligo Number | Start Site | SEQ ID NO: | Sense sequence | Sense Chemsitry | Sense Backbone |
|---|---|---|---|---|---|---|---|
| TYR-53 | 26206 | 25950 | 813 | 236 | UUUGCACAGAUGA | mmm0m0m000mmm-Chl | ooooooooosso |
| TYR-54 | 26207 | 25950 | 813 | 237 | UUUGCACAGAUGA | mmm0m0m000mmm-Chl | ooooooooosso |
| TYR-55 | 26208 | 25950 | 813 | 238 | UUUGCACAGAUGA | mmm0m0m000mmm-Chl | ooooooooosso |
| TYR-56 | 26209 | 25950 | 813 | 239 | UUUGCACAGAUGA | mmm0m0m000mmm-Chl | ooooooooosso |
| TYR-57 | 26210 | 26142 | 813 | 240 | YYYGXAXAGAYGA | mmm0m0m000mmm-Chl | ooooooooosso |
| TYR-58 | 26211 | 26143 | 813 | 241 | YYYGXAXAGAYGA | mmm0m0m0m0mmm-Chl | ooooooooosso |
| TYR-59 | 26212 | 25954 | 816 | 242 | GCACAGAUGAGUA | mm0m000m000mmm-Chl | ooooooooosso |
| TYR-60 | 26213 | 25954 | 816 | 243 | GCACAGAUGAGUA | mm0m000m000mmm-Chl | ooooooooosso |
| TYR-61 | 26214 | 25954 | 816 | 244 | GCACAGAUGAGUA | mm0m000m000mmm-Chl | ooooooooosso |
| TYR-62 | 26215 | 25954 | 816 | 245 | GCACAGAUGAGUA | mm0m000m000mmm-Chl | ooooooooosso |
| TYR-63 | 26216 | 26148 | 816 | 246 | GCACAGAUGAGUA | mm0m0m0m0m0mmm-Chl | ooooooooosso |
| TYR-64 | 26217 | 26149 | 816 | 247 | GXAXAGAYGAGYA | mm0m0m0m0m0mmm-Chl | ooooooooosso |
| TYR-65 | 26218 | 25966 | 881 | 248 | UUCUCCUCUUGGA | mmmmmmmmmm0mm-Chl | ooooooooosso |
| TYR-66 | 26219 | 25966 | 881 | 249 | UUCUCCUCUUGGA | mmmmmmmmmm0mm-Chl | ooooooooosso |
| TYR-67 | 26220 | 25966 | 881 | 250 | UUCUCCUCUUGGA | mmmmmmmmmm0mm-Chl | ooooooooosso |
| TYR-68 | 26221 | 25966 | 881 | 251 | UUCUCCUCUUGGA | mmmmmmmmmm0mm-Chl | ooooooooosso |
| TYR-69 | 26222 | 26154 | 881 | 252 | YYXYXXYXYYGGA | mmmmmmmmmm0mm-Chl | ooooooooosso |
| TYR-70 | 26223 | 25990 | 1111 | 253 | AGGAUUUGCUAGA | mm00mmm0mm0mm-Chl | ooooooooosso |
| TYR-71 | 26224 | 25990 | 1111 | 254 | AGGAUUUGCUAGA | mm00mmm0mm0mm-Chl | ooooooooosso |
| TYR-72 | 26226 | 25990 | 1111 | 255 | AGGAUUUGCUAGA | mm00mmm0mm0mm-Chl | ooooooooosso |
| TYR-73 | 26227 | 25990 | 1111 | 256 | AGGAUUUGCUAGA | mm00mmm0mm0mm-Chl | ooooooooosso |
| TYR-74 | 26228 | 26159 | 1111 | 257 | AGGAYYYGXYAGA | mm00mmm0mm0mm-Chl | ooooooooosso |
| TYR-75 | 26229 | 25994 | 1186 | 258 | GAAUGGAACAAUA | mm0m0m0m0mmm-Chl | ooooooooosso |
| TYR-76 | 26230 | 25994 | 1186 | 259 | GAAUGGAACAAUA | mm0m00m0m000mm-Chl | ooooooooosso |

TABLE 7-continued

Optimized TYR Sense Strand Oligonucleotides

| Oligo Number | RXi Duplex ID | Oligo Number | Start Site | SEQ ID NO: | Sense sequence | Sense Chemsitry | Sense Backbone |
|---|---|---|---|---|---|---|---|
| TYR-77 | 26231 | 25994 | 1186 | 260 | GAAUGGAACAAUA | mm0m00m0m00mm-Chl | ooooooooosso |
| TYR-78 | 26232 | 25994 | 1186 | 261 | GAAUGGAACAAUA | mm0m00m0m00mm-Chl | ooooooooosso |
| TYR-79 | 26233 | 26164 | 1186 | 262 | GAAYGGAAXAAYA | mm0m00m0m00mm-Chl | ooooooooosso |
| TYR-80 | 26234 | 26165 | 1186 | 263 | GAAYGGAAXAAYA | mm0m0mm0mm0mm-Chl | ooooooooosso | o: phosphodiester;
s: phosphorothioate;
P: 5' phosphorylation;
0: 2'-OH;
f: 2'-fluoro;
m: 2' O-methyl.
X = 5 methyl C
and
Y = 5 methyl U

TABLE 8

Optimized TYR Antisense Strand Oligonucleotides

| Oligo Number | RXi Duplex ID | Start Site | Oligo Number | SEQ ID NO: | Antisense sequence | AntiSense Chemistry | AntiSense Backbone |
|---|---|---|---|---|---|---|---|
| TYR-42 | 26195 | 490 | 26127 | 264 | UUUUGCUAAAGUGAGGUAG | Pmfff0ff0f00f00m0mm0 | ooooooooooossssso |
| TYR-43 | 26196 | 490 | 26128 | 265 | UUUUGCUAAAGUGAGGUAG | Pmfff0ff0f00f00m0m10 | ooooooooooossssso |
| TYR-44 | 26197 | 490 | 26129 | 266 | YYYYGXYAAAGYGAGGYAG | Pmfff0ff0f00f00m0mm0 | ooooooooooossssso |
| TYR-45 | 26198 | 490 | 26130 | 267 | YYYYGXYAAAGYGAGGYAG | Pmfff0ff0f00f00m0mf0 | ooooooooooossssso |
| TYR-46 | 26199 | 490 | 25933 | 268 | UUUUGCUAAAGUGAGGUAG | Pmfff0ff0f0m00f00m0f00 | ooooooooooossssso |
| TYR-47 | 26200 | 490 | 25933 | 269 | UUUUGCUAAAGUGAGGUAG | Pmfff0ff0f0m00f00m0f00 | ooooooooooossssso |
| TYR-48 | 26201 | 663 | 26133 | 270 | UAAUCAAUGUCUCUCCAGA | Pmf0ff00f0fffmffmmm0 | ooooooooooossssso |
| TYR-49 | 26202 | 663 | 26134 | 271 | UAAUCAAUGUCUCUCCAGA | Pmf0ff00f0ffmmffmmm0 | ooooooooooossssso |
| TYR-50 | 26203 | 663 | 26135 | 272 | YAAYXAAYGYXYXYXXAGA | Pmf0ff00f0fffmffmmm0 | ooooooooooossssso |
| TYR-51 | 26204 | 663 | 26136 | 273 | YAAYXAAYGYXYXYXXAGA | Pmf0ff00f0ffmmffmmm0 | ooooooooooossssso |
| TYR-52 | 26205 | 663 | 25939 | 274 | UAAUCAAUGUCUCUCCAGA | Pm00ff00f0ffffffff000 | ooooooooooossssso |
| TYR-53 | 26206 | 813 | 26138 | 275 | UCAUCUGUGCAAAUGUCAC | Pmf0fff0f0f0f0fmfmm0 | ooooooooooossssso |
| TYR-54 | 26207 | 813 | 26139 | 276 | UCAUCUGUGCAAAUGUCAC | Pmf0fff0f0f0f0m0fmm0 | ooooooooooossssso |
| TYR-55 | 26208 | 813 | 26140 | 277 | YXAYXYGYGXAAAYGYXAC | Pmf0fff0f0f0f0fmfmm0 | ooooooooooossssso |

TABLE 8-continued

Optimized TYR Antisense Strand Oligonucleotides

| Oligo Number | RXi Duplex ID | Start Site | Oligo Number | SEQ ID NO: | Antisense sequence | AntiSense Chemistry | AntiSense Backbone |
|---|---|---|---|---|---|---|---|
| TYR-56 | 26209 | 813 | 26141 | 278 | YXAYXYGYGXAAAYGYXAC | Pmf0fff0f0f0f0m0fmm0 | oooooooooooosssssso |
| TYR-57 | 26210 | 813 | 25949 | 279 | UCAUCUGUGCAAAUGUCAC | Pmf0fff0f0f000f0ff00 | oooooooooooosssssso |
| TYR-58 | 26211 | 813 | 25949 | 280 | UCAUCUGUGCAAAUGUCAC | Pmf0fff0f0f000f0ff00 | oooooooooooosssssso |
| TYR-59 | 26212 | 816 | 26144 | 281 | UACUCAUCUGUGCAAAUGU | Pm0fff0fff0f0m0m0mm0 | oooooooooooosssssso |
| TYR-60 | 26213 | 816 | 26145 | 282 | UACUCAUCUGUGCAAAUGU | Pm0fff0fff0f0f0m0fm0 | oooooooooooosssssso |
| TYR-61 | 26214 | 816 | 26146 | 283 | YAXYXAYXYGYGXAAAYGU | Pm0fff0fff0f0m0m0mm0 | oooooooooooosssssso |
| TYR-62 | 26215 | 816 | 26147 | 284 | YAXYXAYXYGYGXAAAYGU | Pm0fff0fff0f0f0m0fm0 | oooooooooooosssssso |
| TYR-63 | 26216 | 816 | 25953 | 285 | UACUCAUCUGUGCAAAUGU | Pm0fff0fff0f0f000f00 | oooooooooooosssssso |
| TYR-64 | 26217 | 816 | 25953 | 286 | UACUCAUCUGUGCAAAUGU | Pm0fff0fff0f0f000f00 | oooooooooooosssssso |
| TYR-65 | 26218 | 881 | 26150 | 287 | UCCAAGAGGAGAAGAAUGA | Pmff00m00m00fm0m0fm0 | oooooooooooosssssso |
| TYR-66 | 26219 | 881 | 26151 | 288 | UCCAAGAGGAGAAGAAUGA | Pmff00f00f00fm0m0fm0 | oooooooooooosssssso |
| TYR-67 | 26220 | 881 | 26152 | 289 | YXXAAGAGGAGAAGAAYGA | Pmff00m00m00fm0m0fm0 | oooooooooooosssssso |
| TYR-68 | 26221 | 881 | 26153 | 290 | YXXAAGAGGAGAAGAAYGA | Pmff00f00f00fm0m0fm0 | oooooooooooosssssso |
| TYR-69 | 26222 | 881 | 25965 | 291 | UCCAAGAGGAGAAGAAUGA | Pmff00m00m000m000f00 | oooooooooooosssssso |
| TYR-70 | 26223 | 1111 | 26155 | 292 | UCUAGCAAAUCCUUCCAGU | Pmff00f000fffmfmfmm0 | oooooooooooosssssso |
| TYR-71 | 26224 | 1111 | 26156 | 293 | UCUAGCAAAUCCUUCCAGU | Pmff00f0f0fffmfmf0m0 | oooooooooooosssssso |
| TYR-72 | 26226 | 1111 | 26157 | 294 | YXYAGXAAAYXXYYXXAGU | Pmff00f000fffmfmfmm0 | oooooooooooosssssso |
| TYR-73 | 26227 | 1111 | 26158 | 295 | YXYAGXAAAYXXYYXXAGU | Pmff00f0f0fffmfmf0m0 | oooooooooooosssssso |
| TYR-74 | 26228 | 1111 | 25989 | 296 | UCUAGCAAAUCCUUCCAGU | Pmff00f000fffffff000 | oooooooooooosssssso |
| TYR-75 | 26229 | 1186 | 26160 | 297 | UAUUGUUCCAUUCAUAUAG | Pm0ff0mffm0fff0m0fm0 | oooooooooooosssssso |
| TYR-76 | 26230 | 1186 | 26161 | 298 | UAUUGUUCCAUUCAUAUAG | Pm0ff0ffff0fff0mmm0 | oooooooooooosssssso |
| TYR-77 | 26231 | 1186 | 26162 | 299 | YAYYGYYXXAYYXAYAYAG | Pm0ff0mffm0fff0m0fm0 | oooooooooooosssssso |
| TYR-78 | 26232 | 1186 | 26163 | 300 | YAYYGYYXXAYYXAYAYAG | Pm0ff0ffff0fff0mmm0 | oooooooooooosssssso |

TABLE 8-continued

Optimized TYR Antisense Strand Oligonucleotides

| Oligo Number | RXi Duplex ID | Start Site | Oligo Number | SEQ ID NO: | Antisense sequence | AntiSense Chemistry | AntiSense Backbone |
|---|---|---|---|---|---|---|---|
| TYR-79 | 26233 | 1186 | 25993 | 301 | UAUUGUUCCAUUCAUAUAG | PmOffOffffOfffOfOfOO | ooooooooooosssssso |
| TYR-80 | 26234 | 1186 | 25993 | 302 | UAUUGUUCCAUUCAUAUAG | PmOffOffffOfffOfOfOO | ooooooooooosssssso | o: phosphodiester;
s: phosphorothioate;
P: 5' phosphorylation;
O: 2'-OH;
f: 2'-fluoro;
m: 2' O-methyl.
X = 5 methyl C
and
Y = 5 methyl U

Example 6

Figure 6A:
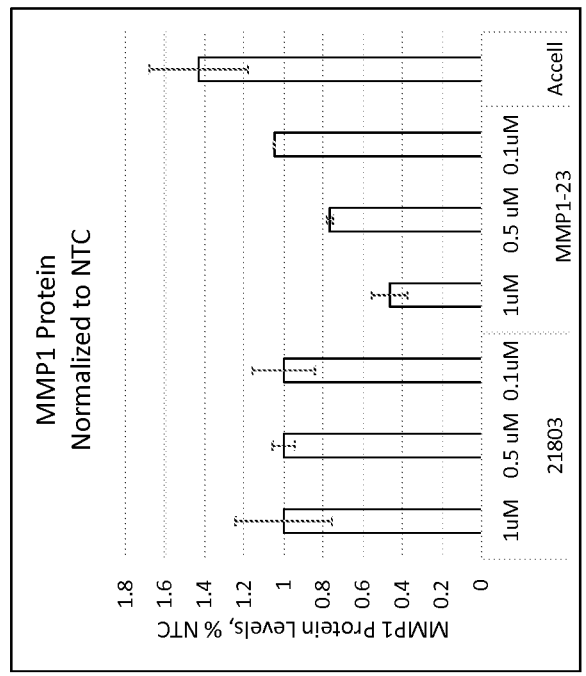
FIG. 6A and FIG. 6B show that reduction of MMP1 mRNA results in dose-dependent reduction of MMP1 enzyme activity.
Figure 6B:
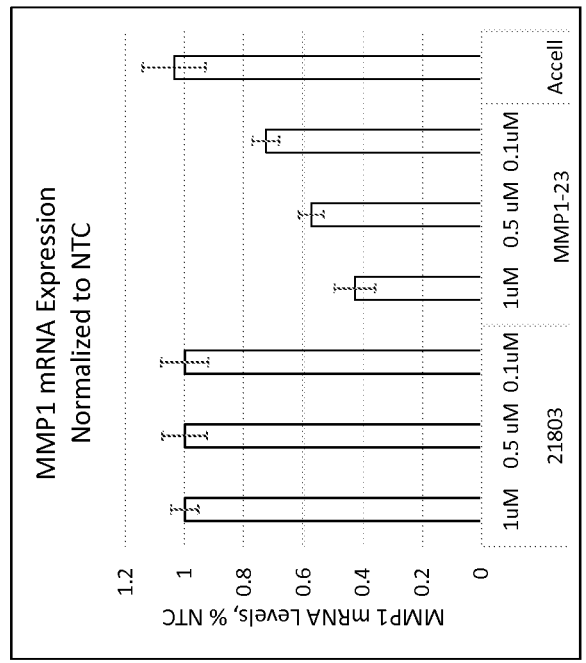

Dose Response Effect of MMP1 Targeting sd-rxRNAs on Tyrosinase Concentrations in HT-1080 Cells The effect of MMP1-targeting sd-rxRNAs on Tyrosinase protein expression was tested in an in vitro dose response study. The sd-rxRNAs were tested for activity in HT-1080 cells (human fibrosarcoma cell line, 100,000 cells/well, 96 well plate). HT-1080 cells were treated with varying concentrations of MMP1-targeting sd-rxRNAs or non-targeting control (#21803) in serum-free media. Concentrations tested were 1, 0.5, and 0.1 µM. The non-targeting control sd-rxRNA (#21803) is of similar structure to the MMP1-targeting sd-rxRNA and contains similar stabilizing modifications throughout both strands. Seventy-two hours post administration, the conditioned media was collected from the cells, pooled, concentrated and protein levels were determined using the SensoLyte® Plus 520 MMP-1 Assay Kit, a fluorimetric enzyme assay which was run according to the manufacturer's protocol (AnaSpec, Fremont, Calif.). FIG. 6 demonstrates a dose response reduction in MMP-1 concentrations after treatment with MMP1-targeting sd-rxRNAs in vitro in HT-1080 cells. Concentrations were calculated based on a standard curve, and were normalized and graphed with respect to the non-targeting control. Error bars represent the standard deviation from the mean of technical duplicates.

Example 7

Figures 7A, 7B:
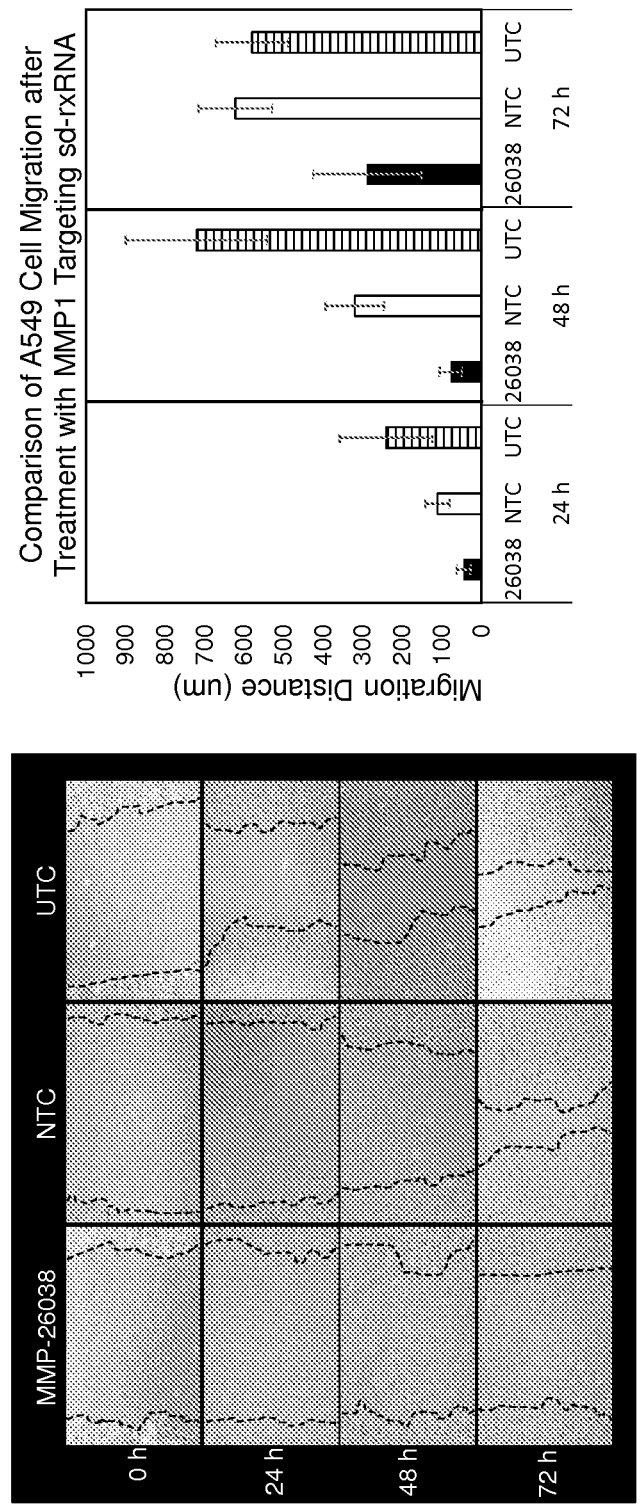
FIG. 7A and FIG. 7B show that MMP1-targeting sd-rxRNA compounds lead to reduced migration rate of A549 lung carcinoma cells in vitro.

Cells Treated with the MMP1 Targeting sd-rxRNA Migrated at a Slower Rate Compared to Untreated or NTC Treated Cells The distance A549 (non-small cell lung cancer) cells migrated in a scratch wound healing assay was measured (FIGS. 7A and 7B). The scratch wounds were generated 48 hours after A549 cells were transfected with a MMP1-targeting sd-rxRNA (100,000 cells/well, 24 well PLL coated plate). Forty-eight hours post transfection of the A549 cells (100,000 cells/well, 24 well PLL coated plate) with either a MMP1-targeting or non-targeting control sd-rxRNA, a scratch wound was made through the monolayer, across the center of the well, using a 200 uL pipet tip. Cells were observed and imaged after the initial scratch was made and at 24 hours and 48 hours post scratch. The width of the scratch was calculated using Spot Advanced imaging software (Spot Imaging Solutions, Sterling Heights, Mich.). The distance of cell migration was calculated by subtracting the average width of the scratch at a given time point from the average width of the scratch at time zero. Error bars in FIG. 7B represent the standard deviation from the mean of biological triplicates (3 measurements per image, 3 images per scratch, 3 wells per treatment).

Example 8

Figure 8:
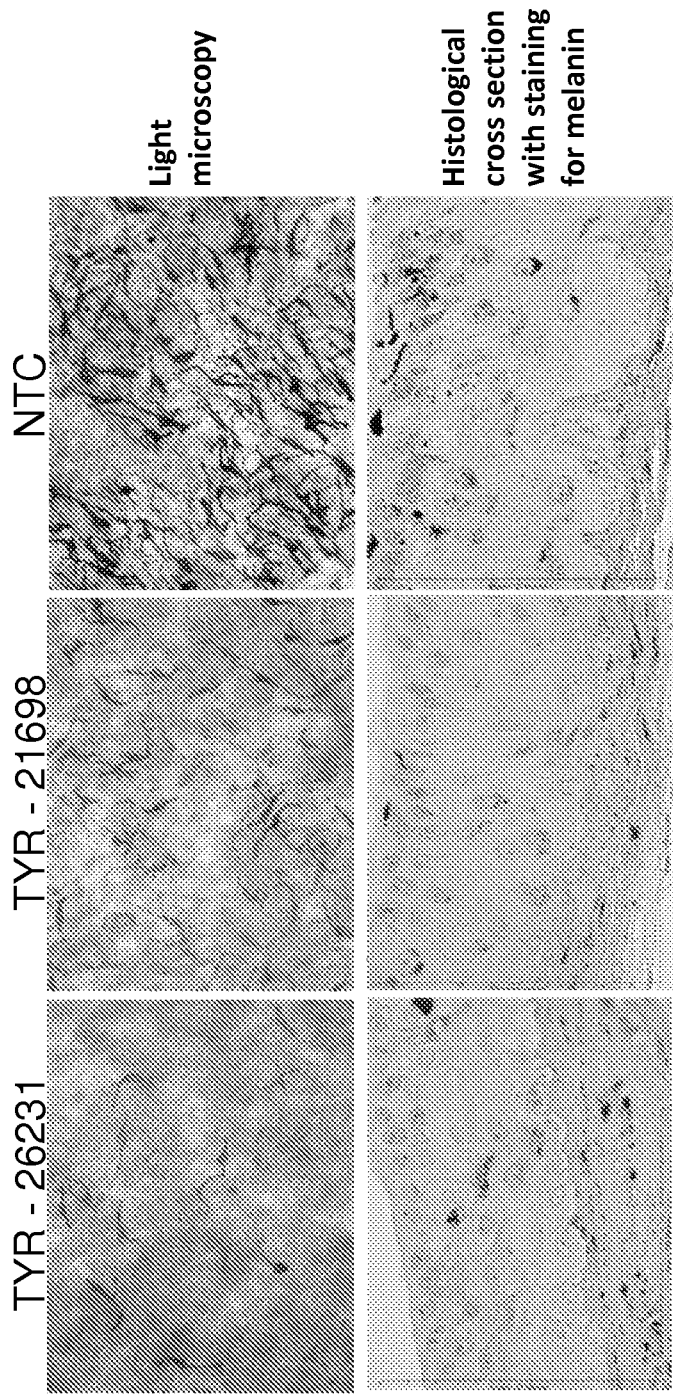
FIG. 8 shows that TYR-targeting sd-rxRNA compounds lead to a visible reduction of pigmentation in vitro. MelanoDerm™ 3-dimensional epidermal culture model containing melanocytes was used. A fourteen day culture was used with TYR-targeting sd-rxRNA added to culture media.

TYR-Targeting sd-rxRNA Compounds in 3-Dimensional Epidermal Model Lead to a Visible Reduction in Pigmentation MelanoDerm™ (MatTek) tissues were treated with optimized sd-rxRNA compounds at 5 uM in culture media for 14 days with media changes every other day, as per manufacturer's protocol. After 14 days, tissues were visualized using light microscopy then formalin fixed and paraffin embedded (FIG. 8). Transverse sections were cut and Fontana-Masson staining was performed to identify melanin (FIG. 8). Tissues treated with TYR targeting sd-rxRNA have fewer melanocytes and less melanin in the tissues while maintaining the structure of the epidermis.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of PCT Publication No. WO2010/033247 (Application No. PCT/US2009/005247), filed on Sep. 22, 2009, and entitled "REDUCED SIZE SELF-DELIVERING RNAI COMPOUNDS," U.S. Pat. No. 8,796,443, issued on Aug. 5, 2014, published as US 2012/0040459 on Feb. 16, 2012, entitled "REDUCED SIZE SELF-DELIVERING RNAI COMPOUNDS," PCT Publication No. WO2009/102427 (Application No. PCT/US2009/000852), filed on Feb. 11, 2009, and entitled, "MODIFIED RNAI POLYNUCLE-OTIDES AND USES THEREOF," and US Patent Publication No. 2011/0039914, published on Feb. 17, 2011 and entitled "MODIFIED RNAI POLYNUCLEOTIDES AND USES THEREOF," PCT Publication No. WO 2011/119887 (Application No. PCT/US2011/029867), filed on Mar. 24, 2011, and entitled RNA INTERFERENCE IN DERMAL AND FIBROTIC INDICATIONS, and U.S. Pat. No. 8,664,189, issued on Mar. 4, 2014, published as US 2011/0237648 on Sep. 29, 2011, entitled "RNA INTERFERENCE IN DERMAL AND FIBROTIC INDICATIONS."

What is claimed is:

1. A chemically modified double stranded nucleic acid molecule, wherein the chemically modified double stranded nucleic acid molecule comprises an antisense strand and a sense strand, wherein the region of the molecule that is double stranded is from 8-15 nucleotides long, wherein the antisense strand contains a single stranded region that is 4-12 nucleotides long, wherein the single stranded region of the antisense strand contains 3, 4, 5, 6, 7, 8, 9, 10, 11 or 12 phosphorothioate modifications, wherein at least 40% of the nucleotides of the double stranded nucleic acid are modified, and wherein the sense strand comprises at least 12 contiguous nucleotides of a sequence selected from SEQ ID NOs 258, 260, 262 and 263 and/or the antisense strand comprises at least 12 contiguous nucleotides of a sequence selected from SEQ ID NOs 297, 298, 299, 300 and 301.

2. The chemically modified double stranded nucleic acid molecule of claim 1, wherein:
the sense strand sequence is selected from the group consisting of SEQ ID NOs 258, 260, 262 and 263, including the modification indicated in Table 7, and the antisense strand sequence is selected from the group consisting of SEQ ID NOs 297, 298, 299, 300 and 301, including the modifications indicated in Table 8.

3. A method for treating retinitis pigmentosa, Addison's disease, neuroblastoma, glioblastoma or Parkinson's disease comprising administering to a subject in need thereof a therapeutically effective amount of a chemically modified double stranded nucleic acid molecule of claim 1.

4. A composition comprising a chemically modified double stranded nucleic acid molecule of claim 1.

* * * * *